US007452701B2

(12) United States Patent
Frey et al.

(10) Patent No.: US 7,452,701 B2
(45) Date of Patent: Nov. 18, 2008

(54) METHODS FOR THE PREPARATION OF β-AMINO ACIDS

(75) Inventors: Perry A. Frey, Madison, WI (US); Frank J. Ruzicka, Lodi, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 286 days.

(21) Appl. No.: 10/235,939

(22) Filed: Sep. 5, 2002

(65) Prior Publication Data
US 2003/0113882 A1 Jun. 19, 2003

Related U.S. Application Data

(60) Continuation-in-part of application No. 09/847,010, filed on May 1, 2001, which is a division of application No. 09/330,611, filed on Jun. 11, 1999, now Pat. No. 6,248,874, which is a continuation-in-part of application No. 09/198,942, filed on Nov. 24, 1998, now abandoned.

(51) Int. Cl.
*C12P 13/08* (2006.01)
*C12N 9/00* (2006.01)
*C12N 9/52* (2006.01)
*C12N 9/90* (2006.01)

(52) U.S. Cl. .................. 435/115; 435/183; 435/220; 435/233; 435/252.3; 435/320.1

(58) Field of Classification Search ................ 435/106, 435/6, 183, 233
See application file for complete search history.

(56) References Cited

U.S. PATENT DOCUMENTS 4,880,738 A 11/1989 Rozzell

OTHER PUBLICATIONS

Hourdou et al., Journal of Antibiotics, vol. 41, No. 2, pp. 207-211, Feb. 1988.*
Costilow, R.N. et al., "Isolation and Identification of β-Lysine as an Intermediate in Lysine Fermentation," Journal of Biological Chemistry, vol. 241, No. 7, pp. 1573-1580 (1966).
Chirpich, T.P. et al., "Purification and Properties of a Pyridoxal Phosphate and S-Adenosylmethionine Activated Enzyme," Journal of Biological Chemistry, vol. 245, pp. 1778-1789 (1970).
Zappia, V. and Barker, H.A., "Studies on Lysine 2,3-Aminomutase Subunit Structure and Sulfhydryl Groups," Biochim. Biophys. Acta, vol. 207, pp. 505-513 (1970).
Aberhart, D.J. et al., "Stereochemistry of Lysine 2,3-Aminomutase," Journal of the American Chemical Society, vol. 103, 6750-6752. (1981).
Aberhart, D.J. et al., "Stereochemistry of Lysine 2,3-Aminomutase Isolated from *Clostridium subterminate* Strain SB4," Journal of the American Chemical Society, vol. 105, pp. 5461-5470 (1983).

Frey, P.A., and Moss, M.L., "S-Adenosylmethionine and the Mechanism of Hydrogen Transfer in the Lysine 2,3-Aminomutase Reaction," Cold Spring Harbor Symposia on Quantitative Biology, vol. LII, pp. 571-577 (1987).
Moss, M. and Frey, P.A., "The Role of S-Adenosylmethionine in the Lysine 2,3-Aminomutase Reaction," The Journal of Biological Chemistry, vol. 262, No. 31, pp. 14859-14862 (1987).
Aberhart, D.J., "Studies on the Mechanism of Lysine 2,3-Aminomutase," J. Chem. Soc. Perkin Trans. 1, pp. 343-350 (1988).
Aberhart, D.J. and Cotting, J., "Mechanistic Studies on Lysine 2,3-Aminomutase: Carbon-13-Deuterium Crossover Experiments," J. Chem. Soc. Perkin Trans 1, pp. 2119-2122 (1988).
Baraniak, J. et al., "Lysine 2,3-Aminomutase," The Journal of Biological Chemistry, vol. 264, No. 3, pp. 1357-1360 (1989).
Frey, P.A. et al., "The Roles of S-Adenosylmethionine and Pyridoxal Phosphate in the Lysine 2,3-Aminomutase Reaction," Annals of the New York Academy of Sciences, vol. 585, pp. 368-378 (1990).
Moss, M.L. and Frey, P.A., "Activation of Lysine 2,3-Aminomutase by S-Adenosylmethionine," The Journal of Biological Chemistry, vol. 265, No. 30, pp. 18112-18115 (1990).
Song, K.B. and Frey, P.A., "Molecular Properties of Lysine-2,3-Aminomutase," The Journal of Biological Chemistry, vol. 266, No. 12, pp. 7651-7655 (1991).
Petrovich, R. M. et al., "Metal Cofactors of Lysine-2,3-Aminomutase," The Journal of Biological Chemistry, vol. 266, No. 12, 7656-7660 (1991).
Kilgore, J.L. and Aberhart, D.J., "Lysine 2,3-Aminomutase: Role of S-Adenosyl-L-Methionine in the Mechanism. Demonstration of Tritium Transfer from (2RS, 3RS)-[3-$^3$H]Lysine to S-Adenosyl-L-Methionine," J. Chem. Soc. Perkin Trans 1, pp. 79-84 (1991).
Ballinger, M.D. et al., "Structure of a Substrate Radical Intermediate in the Reaction of Lysine 2,3-Aminomutase," Biochemistry, vol. 31, No. 44, pp. 10782-10789 (1992).
Ballinger, M.D. et al., "An Organic Radical in the Lysine 2,3-Aminomutase Reaction," Biochemistry, vol. 31, No. 4, pp. 949-953 (1992).
Petrovich, R.M. et al., "Characterization of Iron-Sulfur Clusters in Lysine 2,3-Aminomutase by Electron Paramagnetic Resonance Spectroscopy," Biochemistry, vol. 31, No. 44, pp. 10774-10781 (1992).
Frey, P.A. and Reed, G.H., "Lysine 2,3-Aminomutase and the Mechanism of the Interconversion of Lysine and β-Lysine," Advances in Enzymology, vol. 66, pp. 1-39 (1993).

(Continued)

*Primary Examiner*—Richard G Hutson
(74) *Attorney, Agent, or Firm*—Foley & Lardner LLP

(57) ABSTRACT

Purified β-amino acids are of considerable interest in the preparation of pharmacologically active compounds and industrial precursors. Although enantiomerically pure β-amino acids can be produced by standard chemical synthesis, this traditional approach is time consuming, requires expensive starting materials, and results in a racemic mixture which must be purified further. However, DNA molecules encoding lysine 2,3-aminomutase can be used to prepare β-amino acids by methods that avoid the pitfalls of chemical synthesis. The present invention provides a method of producing enantiomerically pure β-amino acids from α-amino acids comprising catalyzing the conversion of an α-amino acid to a corresponding β-amino acid by utilizing a lysine 2,3-aminomutase as the catalyst.

11 Claims, 8 Drawing Sheets

OTHER PUBLICATIONS

Ballinger, M.D. et al., "Pulsed Electron Paramagnetic Resonance Studies of the Lysine 2,3-Aminomutase Substrate Radical: Evidence for Participation of Pyridoxal 5'-Phosphate in a Radical Rearrangement," Biochemistry, vol. 34, No. 31, pp. 10086-10093 (1995).

Fleischmann, Robert D., et al., "Whole-Genome Random Sequencing and Assembly of *Haemophilus influenzae* Rd," Science, vol. 269, pp. 496-512 (1995).

Koskinen, A.M.P., "Asymmetry: To Make a Distinction," Pure & Appl. Chem., vol. 67, No. 7, pp. 1031-1036 (1995).

Wu, W. et al., "Observation of a Second Substrate Radical Intermediate in the Reaction of Lysine 2,3-Aminomutase: A Radical Centered on the β-Carbon of the Alternative Substrate, 4-Thia-L-lysine," Biochemistry, vol. 34, No. 33, pp. 10532-10537 (1995).

Chang, C.H. et al., "Lysine 2,3-Aminomutase Rapid Mix-Freeze-Quench Electron Paramagnetic Resonance Studies Establishing the Kinetic Competence of a Substrate-Based Radical Intermediate," Biochemistry, vol. 35, No. 34, p. 11081-11084 (1996).

Cardillo, G. and Tomasini, C., "Asymmetric Synthesis of β-Amino Acids and α-Substituted β-Amino Acids," Chemical Society Reviews vol. 25, No. 2, pp. 117-128 (1996).

Sewald, N., "Stereoselective Synthesis of β-Amino Acids via Conjugate Addition of Nitrogen Nucleophiles to α,β-Unsaturated Esters—Recent Advances," Amino Acids, vol. 11, pp. 397-408 (1996).

Stadtman, T., "Lysine Metabolism by Clostridia," Advances in Enzymology and Related Areas of Molecular Biology, vol. 38, pp. 413-448, (1973).

Baker, J. J. and Stadtman, T.C., "Amino Mutases," $B_{12}$ vol. 2, Biochemistry and Medicine, pp. 203-232.

Blattner, Fredrick R., et al., "The Complete Genome Sequence of *Escherichia coli* K-12," Science, vol. 277, pp. 1453-1462, (1997).

Deckert, et al., "The complete genome of the hyperthermophilic bacterium *Aquifex aeolicus*," Nature, vol. 392, pp. 353-358, (1998).

Fraser, et al., "Complete Genome Sequence of Treponema pallidum, the Syphilis Spirochete," Science, vol. 281, pp. 375-388, (1998).

Deckert, et al., "The Complete Genome of the Hyperthermopnilic Bacgterium *Aquifex aeolicus*," Genbank Accession No. E70341.

Fraser, et al., "Complete Genome Sequence of Treponema pallidum, the Syphilis Spirochete," Genbank Accession No. AE001197.

T. P. Chirpich et al., "Enzymic Preparation of L-β-Lysine," *Preparative Biochemistry*, vol. 3, No. 1, pp. 47-52, 1973.

S. Kusumoto et al., "Total Synthesis of Antibiotic Streptothricin F," *Tetrahedron Letters*, vol. 23, No. 29, pp. 2961-2964, 1982; published by Pergamon Press Ltd.

\* cited by examiner $R = CH_2CH_2CH_2NH_3^+$

1. ——— Lysine
2. ·········· Aspartate
3. - - - - - - Glutamate
4. ---------- No Substrate 1. ——— No Substrate
2. ·········· L-Alanine
3. ·········· L-Alanine + Ethylamine
4. ---------- L-Alanine + Propylamine
5. ——— L-Lysine

METHODS FOR THE PREPARATION OF β-AMINO ACIDS

CROSS-REFERENCES TO RELATED APPLICATIONS

This application claims priority to U.S. application Ser. No. 09/847,010, filed May 1, 2001; which claims priority to U.S. application Ser. No. 09/330,611, filed Jun. 11, 1999 (now U.S. Pat. No. 6,248,874); which claims priority to U.S. application Ser. No. 09/198,942, filed Nov. 24, 1998 (now abandoned). The entire contents of all of these documents are hereby incorporated by reference.

GOVERNMENT RIGHTS

This invention was made with United States government support awarded by the following agency: NIH DK 28607. The United States has certain rights in this invention.

STATEMENT AS TO RIGHTS TO INVENTIONS MADE UNDER FEDERALLY-SPONSORED RESEARCH AND DEVELOPMENT

Part of the work performed during development of this invention utilized U.S. Government Funds, specifically NIH Grant Nos. DK28607; DK09306; GM31343; GM30480; GM10816; GM14401; GM15395; GM51806, and GM18282. Therefore, the U.S. Government has certain rights in this invention.

BACKGROUND OF THE INVENTION

1. Field of the Invention

The present invention relates to methods for preparing enantiomerically pure β-amino acids. More particularly, this invention relates to the use lysine 2,3-aminomutase to produce enantiomerically pure β-amino acids.

2. Related Art

Although less abundant than the corresponding (α-amino acids, β-amino acids occur in nature in both free forms and in peptides. Cardillo and Tomasini, *Chem. Soc. Rev.* 25:77 (1996); Sewald, *Amino Acids* 11:397 (1996). Since β-amino acids are stronger bases and weaker acids than α-amino acid counterparts, peptides that contain a β-amino acid in place of an α-amino acid, have a different skeleton atom pattern, resulting in new properties. For example, various peptides are protease inhibitors because the presence of the β-amino-α-hydroxy acid motif acts as a transition state mimic of peptide hydrolysis.

β-amino acids are of particular interest in the preparation of medicaments, such as β-lactams. Well-known β-lactam antimicrobial agents include penicillins, cephalosporins, carbapenems, and monobactams. Other examples of medically useful molecules that contain β-amino-α-hydroxy acids include the anti-tumor agent taxol, the anti-bacterial agent, dideoxykanamicin A, bestatin, an immunological response modifier, the kynostatins, which are highly potent human immunodeficiency virus-1 protease inhibitors, and microginin, a tetrapeptide which has anti-hypertensive properties. Accordingly, enantiomerically pure β-amino-α-hydroxy acids are of considerable importance as crucial components of pharmacologically active compounds. Additionally, enantiomerically pure β-amino acids are useful as precursors for preparing various industrial chemicals.

Therefore, a need exists for an improved method of preparing enantiomerically pure β-amino acids.

SUMMARY OF THE INVENTION

The present invention provides a method of producing enantiomerically pure β-amino acids from α-amino acids comprising catalyzing the conversion of an α-amino acid to a corresponding β-amino acid by utilizing a lysine 2,3-aminomutase as the catalyst. A wide variety of β-amino acids may be produced.

BRIEF DESCRIPTION OF THE DRAWINGS

FIG. 4B. 4.6×enlargement of (2), (3), and (4) of FIG. 4A.

DETAILED DESCRIPTION OF THE INVENTION

1. Definitions

Figure 1A:
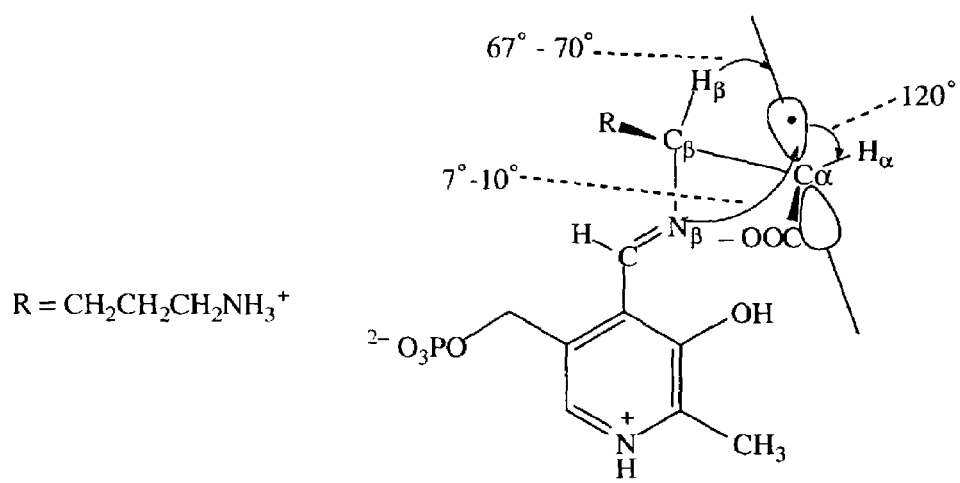
FIG. 1A is the structure of the radical produced during the interconversion of L-lysine to L-β-lysine.

In the description that follows, a number of terms are utilized extensively. Definitions are herein provided to facilitate understanding of the invention.

Cloning vector. A DNA molecule, such as a plasmid, cosmid, phagemid, or bacteriophage, which has the capability of replicating autonomously in a host cell and which is used to transform cells for gene manipulation. Cloning vectors typically contain one or a small number of restriction endonuclease recognition sites at which foreign DNA sequences may be inserted in a determinable fashion without loss of an essential biological function of the vector, as well as a marker gene which is suitable for use in the identification and selection of cells transformed with the cloning vector. Marker genes typically include genes that provide tetracycline resistance or ampicillin resistance.

Complementary DNA (cDNA). Complementary DNA is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule derived from a single mRNA molecule.

Enhancer. A promoter element. An enhancer can increase the efficiency with which a particular gene is transcribed into mRNA irrespective of the distance or orientation of the enhancer relative to the start site of transcription.

Expression. Expression is the process by which a polypeptide is produced from a structural gene. The process involves transcription of the gene into mRNA and the translation of such mRNA into polypeptide(s).

Expression vector. A DNA molecule comprising a cloned structural gene encoding a foreign protein which provides the expression of the foreign protein in a recombinant host. Typically, the expression of the cloned gene is placed under the control of (i.e., operably linked to) certain regulatory sequences such as promoter and enhancer sequences. Promoter sequences may be either constitutive or inducible.

Lysine 2,3-aminomutase. An enzyme that catalyzes the interconversion of L-lysine and L-β-lysine.

Promoter. A DNA sequence which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent if the promoter is a constitutive promoter.

Recombinant host. A recombinant host may be any prokaryotic or eukaryotic cell which contains either a cloning vector or expression vector. This term is also meant to include those prokaryotic or eukaryotic cells that have been genetically engineered to contain the cloned gene(s) in the chromosome or genome of the host cell. For examples of suitable hosts, see Sambrook et al., MOLECULAR CLONING: A LABORATORY MANUAL, Second Edition, Cold Spring Harbor Laboratory, Cold Spring Harbor, N.Y. (1989) ["Sambrook"].

Structural gene. A DNA sequence that is transcribed into messenger RNA (mRNA) which is then translated into a sequence of amino acids characteristic of a specific polypeptide (protein).

As used herein, a substantially pure protein means that the desired purified protein is essentially free from contaminating cellular components, as evidenced by a single band following polyacrylamide-sodium dodecyl sulfate gel electrophoresis (SDS-PAGE). The term "substantially pure" is further meant to describe a molecule which is homogeneous by one or more purity or homogeneity characteristics used by those of skill in the art. For example, a substantially pure lysine 2,3-aminomutase will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of lysine 2,3-aminomutase with other compounds. In addition, the term is not meant to exclude lysine 2,3-aminomutase fusion proteins isolated from a recombinant host.

Lysine 2,3-aminomutase may be used to produce a wide variety of β-amino acids. Although lysine 2,3-aminomutase is selective for L-lysine as its substrate, it also catalyzes the 2,3-aminomutation of other L-α-amino acids. Although any appropriate L-α-amino acid may be utilized, appropriate L-α-amino acids include, but are not limited to, L-lysine, L-aspartic acid, L-glutamic acid, L-alanine, L-methionine, L-arginine, L-phenylalanine, L-tyrosine, L-histidine, L-leucine, L-isoleucine, L-valine, L-asparagine, L-glutamine, L-tryptophan, L-ornithine, ε-N-methyl-L-lysine, N-acetyl-L-ornithine, α-aminobutyric acid, α-aminoisobutyric acid, L-Citrulline, β-alanine, L-norleucine, L-norvaline, L-homoserine, L-homocysteine, L-homoarginine, L-homoglutamine, L-homophenylalanine, L-homocitrulline, L-ethionine, and L-homomethionine. Other appropriate α-amino acids include, but are not limited to, α-aminoheptanoic acid, 2-amino-4-hexenoic acid, 2-amino-4-methylhexanoic acid, 2-amino-4-methylhex-4-enoic acid, 2-amino-5-methylhex-4-enoic acid, α-aminooctanoic acid, α-amino-β-(2-methylenecyclopropyl)-propionic acid, α-aminoadipic acid, α-aminopimelic acid, ethylasparagine, N(5)-isopropylglutamine, N(4)-methylasparagine, γ-methylglutamic acid, γ-methyleneglutamic acid, γ-methyleneglutamine, α-amino-γ-N-acetylaminobutyric acid, β-N-(γ-glutamyl)aminopropionitrile, α-∈-diaminopimelic acid, O-acetylhomoserine, 2-amino-6-hydroxy-aminohexanoic acid, α-amino-δ-hydroxyvaleric acid, O-butylhomoserine, γ,δ-dihydroxyleucine, O-ethylhomoserine, N(5)-(2-hydroxyethyl)asparagine, γ-hydroxyglutamic acid, γ-hydroxyglutamine, ∈-hydroxyaminonorleucine, δ-hydroxyleucine, δ-hydroxylysine, γ-hydroxynorvaline, γ-hydroxyornithine, γ-hydroxyvaline, γ-methyl-γ-hydroxy-glutamic acid, α-amino-β,β-dimethyl-γ-hydroxybutyric acid, O-propylhomoserine, O-succinylhomoserine, m-carboxytyrosine, m-carboxyphenylalanine, 2,4-dihydroxy-6-methylphenylalanine, 3,4-dihydroxyphenylalanine, O-methyltyrosine, m-tyrosine, canavanine, α-amino-γ(guanylureido)valeric acid, γ-hydroxyarginine, γ-hydroxyhomoarginine, (α-amino-∈-amidinocaproic acid, 2-hydroxytryptophan, 5-hydroxytryptophan, 1-methylhistidine, 3-methylhistidine, alliin, 3-amino-(3-carboxy-propyldimethylsulfonium), homolanthionine, S-methylmethionine, thiolhistidine, tyrosine-O-sulfate, 2-amino-4,4-dichlorobutyric acid, 3,5-dibromotyrosine, 3,3'-diiodothyronine, 3,5-diiodotyrosine, 3-monobromotyrosine, 2-monoiodohistidine, monoiodotyrosine, thyroxine, 3,5,3'-triiodothyronine, and O-phosphohomoserine.

2. Isolation of a DNA Molecule that Encodes the Clostridium Lysine 2,3-Aminomutase Lysine 2,3-aminomutase catalyzes the reversible isomerization of L-lysine into L-β-lysine. The enzyme isolated from *Clostridium subterminale* strain SB4 is a hexameric protein of apparently identical subunits, which has a molecular weight of 259,000, as determined from diffusion and sedimentation coefficients. Chirpich et al., *J. Biol. Chem.* 245: 1778 (1970); Aberhart et al., *J. Am. Chem. Soc.* 105:5461 (1983); Chang et al., *Biochemistry* 35:11081 (1996). The clostridial enzyme contains iron-sulfur clusters, cobalt and zinc, and pyridoxal 5'-phosphate, and it is activated by S-adenosylmethionine. Unlike typical adenosylcobalamin-dependent aminomutases, the clostridial enzyme does not contain or require any species of vitamin $B_{12}$ coenzyme.

Although the existence of the clostridial lysine 2,3-aminomutase has been known for over 25 years, there is no report in the scientific literature on the isolation of the gene encoding the enzyme. As described herein, however, DNA molecules encoding the clostridial lysine 2,3-aminomutase gene now have been isolated from a genomic library made from the DNA of *Clostridium subterminale* strain SB4. The nucleotide and predicted amino acid sequences of clostridial lysine 2,3-aminomutase (SEQ ID NOs: 1 and 2) are:

```
  1 ATGATAAATA GAAGATATGA ATTATTTAAA GATGTTAGCG ATGCAGACTG
 51 GAATGACTGG AGATGGCAAG TAAGAAACAG AATAGAAACT GTTGAAGAAC
101 TAAAGAAATA CATACCATTA ACAAAAGAAG AAGAAGAAGG AGTAGCTCAA
151 TGTGTAAAAT CATTAAGAAT GGCTATTACT CCATATTATC TATCATTAAT
201 CGATCCTAAC GATCCTAATG ATCCAGTAAG AAAACAAGCT ATTCCAACAG
251 CATTAGAGCT TAACAAAGCT GCTGCAGATC TTGAAGACCC ATTACATGAA
301 GATACAGATT CACCAGTACC TGGATTAACT CACAGATATC CAGATAGAGT
351 ATTATTATTA ATAACTGATA TGTGCTCAAT GTACTGCAGA CACTGTACAA
401 GAAGAAGATT TGCAGGACAA AGCGATGACT CTATGCCAAT GGAAAGAATA
451 GATAAAGCTA TAGATTATAT CAGAAATACT CCTCAAGTTA GAGACGTATT
501 ATTATCAGGT GGAGACGCTC TTTTAGTATC TGATGAAACA TTAGAATACA
551 TCATAGCTAA ATTAAGAGAA ATACCACACG TTGAAATAGT AAGAATAGGT
601 TCAAGAACTC CAGTTGTTCT TCCACAAAGA ATAACTCCAG AACTTGTAAA
651 TATGCTTAAA AAATATCATC CAGTATGGTT AAACACTCAC TTTAACCATC
701 CAAATGAAAT AACAGAAGAA TCAACTAGAG CTTGTCAATT ACTTGCTGAC
```

```
-continued
 751 GCAGGAGTAC CTCTAGGAAA CCAATCAGTT TTATTAAGAG GAGTTAACGA

801 TTGCGTACAC GTAATGAAAG AATTAGTTAA CAAATTAGTA AAAATAAGAG

851 TAAGACCTTA CTACATCTAT CAATGTGACT TATCATTAGG ACTTGAGCAC

901 TTCAGAACTC CAGTTTCTAA AGGTATCGAA ATCATTGAAG GATTAAGAGG

951 ACATACTTCA GGATACTGCG TACCAACATT CGTTGTTGAC GCTCCAGGTG

1001 GTGGTGGAAA AACACCAGTT ATGCCAAACT ACGTTATTTC ACAAAGTCAT

1051 GACAAAGTAA TATTAAGAAA CTTTGAAGGT GTTATAACAA CTTATTCAGA

1101 ACCAATAAAC TATACTCCAG GATGCAACTG TGATGTTTGC ACTGGCAAGA

1151 AAAAAGTTCA TAAGGTTGGA GTTGCTGGAT TATTAAACGG AGAAGGAATG

1201 GCTCTAGAAC CAGTAGGATT AGAGAGAAAT AAGAGACACG TTCAAGAATA

1251 A

1 MINRRYELFK DVSDADWNDW RWQVRNRIET VEELKKYIPL TKEEEEGVAQ

51 CVKSLRMAIT PYYLSLIDPN DPNDPVRKQA IPTALELNKA AADLEDPLHE

101 DTDSPVPGLT HRYPDRVLLL ITDMCSMYCR HCTRRRFAGQ SDDSMPMERI

151 DKAIDYIRNT PQVRDVLLSG GDALLVSDET LEYIIAKLRE IPHVEIVRIG

201 SRTPVVLPQR ITPELVNMLK KYHPVWLNTH FNHPNEITEE STRACQLLAD

251 AGVPLGNQSV LLRGVNDCVH VMKELVNKLV KIRVRPYYIY QCDLSLGLEH

301 FRTPVSKGIE IIEGLRGHTS GYCVPTFVVD APGGGGKTPV MPNYVISQSH

351 DKVILRNFEG VITTYSEPIN YTPGCNCDVC TGKKKVHKVG VAGLLNGEGM

401 ALEPVGLERN KRHVQE
```

DNA molecules encoding the clostridial lysine 2,3-aminomutase gene can be obtained by screening cDNA or genomic libraries with polynucleotide probes having nucleotide sequences based upon SEQ ID NO: 1. For example, a suitable library can be prepared by obtaining genomic DNA from *Clostridium subterminale* strain SB4 (ATCC No. 29748) and constructing a library according to standard methods. See, for example, Ausubel et al. (eds.), SHORT PROTOCOLS IN MOLECULAR BIOLOGY, 3rd Edition, pages 2-1 to 2-13 and 5-1 to 5-6 (John Wiley & Sons, Inc. 1995).

Alternatively, the clostridial lysine 2,3-aminomutase gene can be obtained by synthesizing DNA molecules using mutually priming long oligonucleotides. See, for example, Ausubel et al., (eds.), CURRENT PROTOCOLS IN MOLECULAR BIOLOGY, pages 8.2.8 to 8.2.13 (1990) ["Ausubel"]. Also, see Wosnick et al., *Gene* 60:115 (1987); and Ausubel et al. (eds.), SHORT PROTOCOLS IN MOLECULAR BIOLOGY, 3rd Edition, pages 8-8 to 8-9 (John Wiley & Sons, Inc. 1995). Established techniques using the polymerase chain reaction provide the ability to synthesize DNA molecules at least 2 kilobases in length. Adang et al., *Plant Molec. Biol.* 21:1131 (1993); Bambot et al., *PCR Methods and Applications* 2:266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993); Holowachuk et al., *PCR Methods Appl.* 4:299 (1995).

Variants of clostridial lysine 2,3-aminomutase can be produced that contain conservative amino acid changes, compared with the parent enzyme. That is, variants can be obtained that contain one or more amino acid substitutions of SEQ ID NO: 2, in which an alkyl amino acid is substituted for an alkyl amino acid in the clostridial lysine 2,3-aminomutase amino acid sequence, an aromatic amino acid is substituted for an aromatic amino acid in the clostridial lysine 2,3-aminomutase amino acid sequence, a sulfur-containing amino acid is substituted for a sulfur-containing amino acid in the clostridial lysine 2,3-aminomutase amino acid sequence, a hydroxy-containing amino acid is substituted for a hydroxy-containing amino acid in the clostridial lysine 2,3-aminomutase amino acid sequence, an acidic amino acid is substituted for an acidic amino acid in the clostridial lysine 2,3-aminomutase amino acid sequence, a basic amino acid is substituted for a basic amino acid in the clostridial lysine 2,3-aminomutase amino acid sequence, or a dibasic monocarboxylic amino acid is substituted for a dibasic monocarboxylic amino acid in the clostridial lysine 2,3-aminomutase amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) cysteine and methionine, (4) serine and threonine, (5) aspartate and glutamate, (6) glutamine and asparagine, and (7) lysine, arginine and histidine.

Conservative amino acid changes in the clostridial lysine 2,3-aminomutase can be introduced by substituting nucleotides for the nucleotides recited in SEQ ID NO: 1. Such "conservative amino acid" variants can be obtained, for example, by oligonucleotide-directed mutagenesis, linker-scanning mutagenesis, mutagenesis using the polymerase chain reaction, and the like. Ausubel et al., supra, at pages 8.0.3-8.5.9; Ausubel et al. (eds.), SHORT PROTOCOLS IN MOLECULAR BIOLOGY, 3rd Edition, pages 8-10 to 8-22 (John Wiley & Sons, Inc. 1995). Also see generally, McPherson (ed.), DIRECTED MUTAGENESIS: A PRACTICAL APPROACH, IRL Press (1991). The ability of such variants to convert L-lysine to L-β-lysine can be determined using a standard enzyme activity assay, such as the assay described herein.

Lysine 2, 3-aminomutase variants that contain one or more non-conservative amino acid substitutions, such as those based on clostridial lysine 2,3-aminomutase, and retain the ability to produce β-amino acids from (α-amino acids can also be produced and use in the present methods. Non-conservative amino acid substitutions are known in the art and include, without limitation, leucine for aspartate or valine for threonine.

In addition, routine deletion analyses of DNA molecules can be performed to obtain "functional fragments" of the clostridial lysine 2,3-aminomutase. As an illustration, DNA molecules having the nucleotide sequence of SEQ ID NO: 1 can be digested with Bal31 nuclease to obtain a series of nested deletions. The fragments are then inserted into expression vectors in proper reading frame, and the expressed polypeptides are isolated and tested for lysine 2,3-aminomutase enzyme activity. One alternative to exonuclease digestion is to use oligonucleotide-directed mutagenesis to introduce deletions or stop codons to specify production of a desired fragment. Alternatively, particular fragments of the clostridial lysine 2,3-aminomutase gene can be synthesized using the polymerase chain reaction. Standard techniques for functional analysis of proteins are described by, for example, Treuter et al., *Molec. Gen. Genet.* 240:113 (1993); Content et al., "Expression and preliminary deletion analysis of the 42 kDa 2-5A synthetase induced by human interferon," in BIOLOGICAL INTERFERON SYSTEMS, PROCEEDINGS OF ISIR-TNO MEETING ON INTERFERON SYSTEMS, Cantell (ed.), pages 65-72 (Nijhoff 1987); Herschman, "The EGF Receptor," in CONTROL OF ANIMAL CELL PROLIFERATION, Vol. 1, Boynton et al., (eds.) pages 169-199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

The present invention also contemplates functional fragments of clostridial lysine 2,3-aminomutases that have conservative and non-conservative amino acid changes.

3. Expression of Cloned Lysine 2,3-Aminomutase

To express the polypeptide encoded by a lysine 2,3-aminomutase gene, the DNA sequence encoding the enzyme must be operably linked to regulatory sequences that control transcriptional expression in an expression vector and then, introduced into either a prokaryotic or eukaryotic host cell. In addition to transcriptional regulatory sequences, such as promoters and enhancers, expression vectors can include translational regulatory sequences and a marker gene which is suitable for selection of cells that carry the expression vector.

Suitable promoters for expression in a prokaryotic host can be repressible, constitutive, or inducible. Suitable promoters are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacλpr, phoA, gal, trc and lacZ promoters of *E. coli*, the α-amylase and the $\sigma^{28}$-specific promoters of *B. subtilis*, the promoters of the bacteriophages of *Bacillus*, *Streptomyces* promoters, the int promoter of bacteriophage lambda, the bla promoter of the β-lactamase gene of pBR322, and the CAT promoter of the chloramphenicol acetyl transferase gene. Prokaryotic promoters are reviewed by Glick, *J. Ind. Microbiol.* 1:277 (1987); Watson et al., MOLECULAR BIOLOGY OF THE GENE, 4th Ed., Benjamin Cummins (1987); Ausubel et al., supra, and Sambrook et al., supra.

Preferred prokaryotic hosts include *E. coli*, Clostridium, and Haemophilus. Suitable strains of *E. coli* include DH1, DH4α, DH5, DH5α, DH5αF', DH5αMCR, DH10B, DH10B/p3, DH11S, C600, HB101, JM101, JM105, JM109, JM110, K38, RR1, Y1088, Y1089, CSH18, ER1451, BL21 (DE3), BL21(DE3)plysS, BLR(DE3), BLR(DE3)plysS, and ER1647 (see, for example, Brown (Ed.), MOLECULAR BIOLOGY LABFAX, Academic Press (1991)). Suitable Clostridia include *Clostridium subterminale* SB4 (ATCC No. 29748) and *Clostridium acetobutylicum* (ATCC No. 824), while a suitable Haemophilus host is *Haemophilus influenza* (ATCC No. 33391).

An alternative host is *Bacillus subtilus,* including such strains as BR151, YB886, MI119, MI120, and B170. See, for example, Hardy, "Bacillus Cloning Methods," in DNA CLONING: A PRACTICAL APPROACH, Glover (Ed.), IRL Press (1985).

Methods for expressing proteins in prokaryotic hosts are well-known to those of skill in the art. See, for example, Williams et al., "Expression of foreign proteins in *E. coli* using plasmid vectors and purification of specific polyclonal antibodies," in DNA CLONING 2: EXPRESSION SYSTEMS, 2nd Edition, Glover et al. (eds.), pages 15-58 (Oxford University Press 1995). Also see, Ward et al., "Genetic Manipulation and Expression of Antibodies," in MONOCLONAL ANTIBODIES: PRINCIPLES AND APPLICATIONS, pages 137-185 (Wiley-Liss, Inc. 1995); and Georgiou, "Expression of Proteins in Bacteria," in PROTEIN ENGINEERING: PRINCIPLES AND PRACTICE, Cleland et al. (eds.), pages 101-127 (John Wiley & Sons, Inc. 1996).

An expression vector can be introduced into bacterial host cells using a variety of techniques including calcium chloride transformation, electroporation, and the like. See, for example, Ausubel et al. (eds.), SHORT PROTOCOLS IN MOLECULAR BIOLOGY, 3rd Edition, pages 1-1 to 1-24 (John Wiley & Sons, Inc. 1995).

To maximize recovery of functional lysine 2,3-aminomutase from recombinant hosts, transformed cells should be cultured under anaerobic conditions or under air without oxygen enrichment. Methods for culturing recombinant clostridia are well-known to those of skill in the art. See, for example, Mermelstein et al., *Ann. N. Y. Acad. Sci.* 721:54 (1994); Walter et al, *Ann. N.Y Acad. Sci.* 721:69. (1994). Additionally, anaerobic culturing of bacteria is well known in the art. See, for example, Smith and Neidhardt, *J. Bacteriol.* 154:336 (1983).

4. Isolation of Cloned Lysine 2,3-Aminomutase and Production of Anti-Lysine 2,3-Aminomutase Antibodies A. Isolation of Recombinant Lysine 2,3-Aminomutase General methods for recovering protein produced by a bacterial system are provided by, for example, Grisshammer et al., "Purification of over-produced proteins from *E. coli* cells," in DNA CLONING 2: EXPRESSION SYSTEMS, 2nd Edition, Glover et al. (eds.), pages 59-92 (Oxford University Press 1995); Georgiou, "Expression of Proteins in Bacteria," in PROTEIN ENGINEERING: PRINCIPLES AND PRACTICE, Cleland et al. (eds.), pages 101-127 (Wiley-Liss, Inc. 1996).

Recombinant lysine 2,3-aminomutases can be purified from bacteria using standard methods that have been used to purify *Clostridium subterminale* SB4 lysine 2,3-aminomutase. In general, several precautions can be taken to ensure high enzyme activity of the purified protein. As discussed above, for example, enzyme activity will generally be maximal when host cells are cultured under anaerobic conditions or conditions which restrict the presence of oxygen, Frey and Reed, *Adv. Enzymol.* 66:1 (1993), although rigid anaeorobic conditions are not required in culturing host cells and culture conditions in air have been successful. Oxygen should also be excluded during all purification steps. Purification under anaerobic conditions protects metal cofactors from being irreversibly degraded and allows maximal activity to be attained upon activation with S-adenosylmethionine. However, variants of lysine 2,3-aminomutase may be stable in air and even function under aerobic conditions.

Enzyme activity of isolated lysine 2,3-aminomutase can also be maximized by including cobalt in culture media and purification buffers. Suitable culture media, for example, contain 10-100 μM $CoCl_2$, while purification buffers may contain 5 μM $CoCl_2$. Culture media may also contain 10-100 μM $Fe^{2+}$. In addition, the inclusion of pyridoxal 5'-phosphate and lysine in purification buffers will aid in the stabilization of enzyme activity. For example, purification buffers may contain 10-100 μM pyridoxal 5'-phosphate and 100 μM lysine.

As an illustration, recombinant bacterial host cells that over-produce lysine 2,3-aminomutase can be cultured under anaerobic conditions in medium described by Chirpich et al., *J. Biol. Chem.* 245:1778 (1970), which also contains 100 μM ferric ammonium sulfate and 100 μM cobalt chloride. Typically, cells are harvested at $A_{660}$ values of 0.5 to 0.7.

The enzyme can be purified according to the procedure of Moss and Frey, *J. Biol. Chem.* 265:18112 (1990), as modified by Petrovich et al., *J. Biol. Chem.* 226:7656 (1991). In this procedure, all steps are performed in standard buffer, which consists of 30 mM Tris-HCl (pH 8.0), 0.1 mM dithiothreitol, 0.1 mM pyridoxal phosphate, 0.1 mM lysine, and 4.0 ml of a saturated solution of phenylmethanesulfonylflouride (in 95% ethanol) per liter of buffer. All steps are carried out at 0-4° C. Centrifugations can be performed in a Sorvall RC-5 centrifuge with a GSA rotor. Sonication and streptomycin sulfate precipitation steps are performed in a glove box under nitrogen. During all other steps, a stream of nitrogen or argon is maintained over the protein at all times, and all containers are flushed with argon before use. Alternatively, all steps, from cell disruption through chromatographic separations, can be performed in a nitrogen atmosphere in a Coy anaerobic chamber.

According to this method, fifty grams of bacterial cells are thawed and washed in 100 ml of standard buffer. The washed pellet is resuspended in 65 ml of standard buffer and sonicated using a Sonifier (Ultrasonics, Model W255R) at 72% of maximum power for a total of four minutes in one minute bursts. The solution should be cooled to 4° C. between bursts. After adding an additional 10 ml of buffer, the solution is centrifuged at 13,000 rpm for 30 minutes.

The supernatant fluid, including the viscous layer above the pellet, is decanted, and 25 ml of a 14% solution of streptomycin sulfate in standard buffer is added dropwise over a period of 30 minutes. The suspension is then centrifuged at 13,000 rpm for 45 minutes.

After measuring the volume of supernatant fluid, sufficient solid ammonium sulfate is added during 10 minutes to give a solution 42% saturated in ammonium sulfate, which is then stirred for an additional 40 minutes. The suspension is centrifuged for 30 minutes at 13,000 rpm, the pellet is discarded, the volume of the liquid layer is measured, and sufficient ammonium sulfate is added to give a solution 52% saturated in ammonium sulfate. After centrifugation at 13,000 rpm for 45 minutes, the resulting pellet is resuspended in 4-5 ml of standard buffer (final volume: 12-15 ml).

The isolated protein is then applied to a 100 ml column of Phenyl Sepharose equilibrated with standard buffer that also contains 2 M ammonium sulfate. The column is eluted with a linear gradient, decreasing from 2 M to 0 M ammonium sulfate in the same buffer, using a total volume of one liter, at a flow rate of 1.5-2 ml per minute. Ten milliliter fractions are collected. The column is then washed with an additional 250 ml of the same buffer less ammonium sulfate. The fractions containing lysine 2,3-aminomutase are located by $A_{410}$ measurements and activity assays. The enzyme typically elutes from the column just before the end of the gradient. Active fractions are combined and the protein is concentrated by the addition of ammonium sulfate to 75% saturation, followed by stirring for 45 minutes. After centrifugation at 9,000 rpm for 40 minutes, the pellet is frozen with liquid nitrogen and stored at −70° C.

The enzyme can be purified further by ion exchange chromatography through a 50 ml column of QAE Sepharose, followed by gel permeation through a column (2.7×37 cm, 210 ml) of Sephacryl S-300 superfine. Petrovich et al., *J. Biol. Chem.* 226:7656 (1991).

The above procedure can be used to obtain enzyme preparations that are typically homogenous and that migrate as a single prominent band ($M_r$=47,000) on SDS-PAGE gels. Isolated lysine 2,3-aminomutase appears to be about 90% pure, although a very few faint additional bands may appear on heavily loaded SDS-PAGE gels.

Additional variations in purification are described by Petrovich et al., *J. Biol. Chem.* 226:7656 (1991), and can be devised by those of skill in the art. For example, anti-lysine 2,3-aminomutase antibodies, obtained as described below, can be used to isolate large quantities of lysine 2,3-aminomutase by immunoaffinity purification. Alternatively, recombinant lysine 2,3-aminomutase can be His-tagged an purified on a nickel column.

Lysine 2,3-aminomutase activity can be determined by measuring the conversion of radiolabeled L-lysine to radiolabeled L-β-lysine. For example, Chirpich et al., *J. Biol. Chem.* 245:1778 (1970), describe a radioenzyme assay using $^{14}C$-labeled L-lysine. Briefly, an enzyme activation solution is prepared by mixing the following components in the following order: sufficient distilled water to give a final volume of 120 μl, 5.0 μl of 1.0 M Tris-HCl (pH 8.2), 5.0 μl of 1.2 mM pyridoxal phosphate, test enzyme, 5.0 μl of 0.3 M glutathione (pH 8.3), 5.0 μl of 24 mM ferrous ammonium sulfate, and 5.0 μl of 24 mM sodium dithionite. During mixing, a flow of argon should be maintained to the bottom of tubes to protect auto-oxidizable components.

Immediately after addition of dithionite, tubes are mixed gently to avoid exposure of the solution to air. An acid-washed glass capillary (14 cm long×0.8 mm inner diameter) is filled with the activation solution until about one centimeter of free space remains at each end. After sealing both ends with a gas-oxygen torch, capillary tubes are incubated in a 37° C. water bath for 60 minutes. After incubation, capillary tubes are broken at one end, and a 5 μl aliquot of activated enzyme solution is removed from the center using a 10 μl Hamilton syringe and assayed.

Components for the assay solution are added to tubes in the following order: 35 μl of distilled water, 5 μl of 0.3 M Tris-HCl (pH 7.8), 5.0 μl of 0.12 M $^{14}C$-labeled L-lysine (0.033 μCi per μmole, uniformly labeled), 5.0 μl of 46 μM S-adenosylmethionine (in 10 mM HCl), 5 μl of 12 mM sodium dithionite, and 5 µl of activated enzyme. Just before addition of dithionite, a flow of argon is started to avoid oxidation. Each sample is sealed in a capillary tube and incubated for 15 minutes in a 30° C. water bath. The reaction is stopped by adding the reaction mixture to 30 µl of 0.4 N formic acid.

Lysine and β-lysine in the acidified reaction mixture are separated by paper ionophoresis. For each determination, 5 µl of carrier β-lysine (10 mM) and two 5 µl aliquots of the acidified reaction mixture are applied along a line near the middle of a sheet of filter paper (56×46 cm). After ionophoresis, the amino acids are located by dipping the dried paper in 0.01% ninhydrin in acetone. The spots are cut out and counted in a scintillation counter.

The basic assay protocol of Chirpich et al. can be varied. For example, the activation solution can be modified by replacing glutathione with dihydrolipoate, and ferrous ammonium sulfate can be replaced with ferric ammonium sulfate. Moss and Perry, *J. Biol. Chem.* 262:14859 (1987). In another variation, the test enzyme can be activated by incubation at 30° C. for six hours. Petrovich et al., *J. Biol. Chem.* 266:7656 (1991). Moreover, Ballinger et al., Biochemistry 31:949 (1992), describe several modifications of the basic method including the use of an anaerobic chamber to perform the entire procedure. In another variation, lysine and β-lysine can be derivatized as phenylisothiocyanates (PITC) and separated by HPLC, as described in Example 5. Those of skill in the art can devise further modifications of the assay protocol.

B. Preparation of Anti-Lysine 2,3-Aminomutase Antibodies and Fragments Thereof

Antibodies to lysine 2,3-aminomutase can be obtained, for example, using the product of an expression vector as an antigen. Polyclonal antibodies to recombinant enzyme can be prepared using methods well-known to those of skill in the art. See, for example, Green et al., "Production of Polyclonal Antisera," in IMMUNOCHEMICAL PROTOCOLS (Manson, ed.), pages 1-5 (Humana Press 1992). Also see, Williams et al., "Expression of foreign proteins in *E. coli* using plasmid vectors and purification of specific polyclonal antibodies," in DNA CLONING 2: EXPRESSION SYSTEMS, 2nd Edition, Glover et al. (eds.), pages 15-58 (Oxford University Press 1995).

Alternatively, an anti-lysine 2,3-aminomutase antibody can be derived from a rodent monoclonal antibody (MAb). Rodent monoclonal antibodies to specific antigens may be obtained by methods known to those skilled in the art. See, for example, Kohler et al., *Nature* 256:495 (1975), and Coligan et al. (eds.), CURRENT PROTOCOLS IN IMMUNOLOGY, VOL. 1, pages 2.5.1-2.6.7 (John Wiley & Sons 1991) ["Coligan"]. Also see, Picksley et al., "Production of monoclonal antibodies against proteins expressed in *E. coli*," in DNA CLONING 2: EXPRESSION SYSTEMS, 2nd Edition, Glover et al. (eds.), pages 93-122 (Oxford University Press 1995).

Briefly, monoclonal antibodies (MAbs) can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

For particular uses, it may be desirable to prepare fragments of anti-lysine 2,3-aminomutase antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. Nos. 4,036,945 and 4,331,647 and references contained therein. Also, see Nisonoff et al., *Arch Biochem. Biophys.* 89:230 (1960); Porter, *Biochem. J.* 73:119 (1959), Edelman et al., in METHODS IN ENZYMOLOGY VOL. 1, page 422 (Academic Press 1967), and Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde. See, for example, Sandhu, *Crit. Rev. Biotech.* 12:437 (1992).

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2:97 (1991). Also see Bird et al., *Science* 242:423 (1988), Ladner et al., U.S. Pat. No. 4,946,778, Pack et al., *Bio/Technology* 11:1271 (1993), and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in

5. Isolation of Additional Lysine 2,3-Aminomutase Genes

The nucleotide sequences of the clostridial lysine 2,3-aminomutase gene and antibodies to the enzyme provide a means to isolate additional lysine 2,3-aminomutase genes. Such genes can encode enzymes from various organisms, including but not limited to *Porphyromonas, Bacillus, Deinococcus, Aquifex, Treponema, Haemophilus, Escherichia,* and *Streptomyces*. Other organisms having gene products with the appropriate homology include *Thermoanaerobacter tengcongensis, Fusobacterium nucleatum, Bacillus anthracis, Bacillus halodurans, Dehalococcoides ethenogenes 1, Methanosarcina acetivorans, Methanosarcina mazei* Goel, *Dehalococcoides ethenogenes 2, Clostridium difficile, Thermoanerobacter tengcongenesis, Caulobacter crescentus, Rhodopseudomonas palustris, Rhodobacter spharoides, Rhodosphaerillium rubrum, Mesorhizobium loti, Agrobacterium tumefaciens, Treponema pallidum, Sinorhizobium meliloti, Salmonella typhimurium,* Magnetococcus sp. MC-1, *Treponema denticola, Salmonella enterica, Haemophilus influenzae, Actinobacillus actinomycetecem, Pasteurella multicoda, Yersinia pestus, Vibrio cholerae, Legionella pneumophila, Xanthomonas campestris, Escherichia coli, Xylella fastidiosa, Myzus persicae, Xanthomonas axonopodis, porphyromonas gingivalis, Bacillus subtilus, Deinococcus radiodurans, Aquifex aeolicus* and *Haemophilus influenzae*.

For example, the amino acid sequence of the clostridial lysine 2,3-aminomutase was used to identify related enzymes in various bacteria. Sequence analyses revealed a sequence identity of about 72%, 64%, 54%, 48%, 39%, 33% and 31% between the amino acid sequence of the clostridial enzyme and unknown gene products of *Porphyromonas gingivalis* (incomplete genome, The Institute for Genomic Research "TIGR" hypothetical protein), *Bacillus subtilis* (AF015775), *Deinococcus radiodurans* (incomplete genome, TIGR hypothetical protein), *Aquifex aeolicus* (AE000690), *Treponema pallidum* (AE001197), *Haemophilus influenza* (P44641), and *Escherichia coli* (P39280) respectively.

The nucleotide and amino acid sequences (SEQ ID NOs: 3 and 4) of the *E. coli* polypeptide are:

```
   1 ATGGCGCATATTGTAACCCTAAATACCCCATCCAGAGAAGATTGGTTAACGCAACTTGCC
  61 GATGTTGTGACCGATCCTGATGAACTTCTGCGTCTTTTGAATATAGACGCGGAGGAAAAA
 121 CTGTTAGCCGGACGCAGCGCCAAAAAGCTTTTTGCCCTGCGTGTGCCCCGCTCATTTATC
 181 GATCGCATGGAGAAAGGCAATCCGGACGATCCTCTTTTGCGTCAGGTACTTACCTCGCAA
 241 GATGAGTTTGTCATCGCGCCCGGATTCTCCACCGACCCACTGGAAGAACAGCACAGCGTA
 301 GTGCCTGGTTTGTTGCATAAATACCACAACCGGGCGCTTTTGCTGGTCAAAGGCGGCTGC
 361 GCGGTAAATTGCCGCTATTGCTTCCGTCGTCACTTCCCCTATGCCGAAAATCAGGGCAAC
 421 AAGCGTAACTGGCAAACTGCACTTGAGTATGTTGCTGCGCATCCGGAACTGGACGAGATG
 481 ATTTTCTCCGGCGGCGATCCGCTGATGGCGAAAGATCACGAGCTGGACTGGTTGCTCACA
 541 CAACTGGAAGCCATCCCGCATATAAAACGTCTGCGGATTCACGCCGTCTGCCGATTGTG
 601 ATCCCGGCACGTATCACCGAGGCGCTGGTTGAATGCTTTGCCCGTTCTACGCTGCAAATC
 661 TTGCTGGTGAATCACATCAACCATGCCAATGAGGTAGATGAAACATTCCGTCAGGCGATG
 721 GCTAAGTTGCGCCGGGTAGGCGTTACTTTGCTGAACCAGAGCGTTCTGTTACGTGATGTG
 781 AACGATAACGCACAAACGCTGGCAAACCTGAGTAATGCGTTGTTCGATGCCGGCGTAATG
 841 CCGTATTACCTGCATGTGCTCGATAAAGTACAGGGCGCGGCGCATTTTATGGTGAGTGAT
 901 GACGAAGCACGGCAGATTATGCGTGAGTTGCTGACACTGGTGTCGGGATATCTGGTGCCG
 961 AAACTGGCGCGAGAAATTGGCGGCGAACCCAGCAAAACGCCGCTGGATCTCCAGCTACGC
1021 CAGCAGTAA
```

```
  1 MAHIVTLNTPSREDWLTQLADVVTDPDELLRLLNIDAEEKLLAGRSAKKL
 51 FALRVPRSFIDRMEKGNPDDPLLRQVLTSQDEFVIAPGFSTDPLEEQHSV
101 VPGLLHKYHNRALLLVKGGCAVNCRYCFRRHFPYAENQGNKRNWQTALEY
151 VAAHPELDEMIFSGGDPLMAKDHELDWLLTQLEAIPHIKRLRIHSRLPIV
201 IPARITEALVECFARSTLQILLVNHINHANEVDETFRQAMAKLRRVGVTL
251 LNQSVLLRDVNDNAQTLANLSNALFDAGVMPYYLHVLDKVQGAAHFMVSD
301 DEARQIMRELLTLVSGYLVPKLAREIGGEPSKTPLDLQLRQQ
```

The nucleotide and amino acid sequences (SEQ ID NOs: 5 and 6) of the *H. influenza* polypeptideare:

```
  1 ATGCGTATTTTACCCCAAGAACCCGTCATTAGAGAAGAACAAAATTGGCTCACAATTCTA
 61 AAAAATGCCATTTCAGATCCTAAATTATTACTAAAAGCCTTAAATTTACCAGAAGATGAT
121 TTTGAGCAATCCATTGCTGCGCGGAAACTTTTTTCGCTCCGCGTGCCACAACCTTTCATT
181 GATAAAATAGAAAAGGTAATCCGCAAGATCCCCTTTTCTTGCAAGTGATGTGTTCTGAT
241 TTAGAGTTTGTGCAAGCGGAGGGATTTAGTACGGATCCCTTAGAAGAAAAAAATGCCAAT
301 GCGGTGCCAAATATTCTTCATAAATATAGAAATCGCTTGCTCTTTATGGCAAAAGGCGGT
361 TGTGCGGTGAATTGTCGTTATTGCTTTCGCCGACATTTTCCTTACGATGAAAACCCAGGA
421 AATAAAAAAAGCTGGCAACTGGCGTTAGATTACATTGCGGCACATTCTGAAATAGAAGAA
481 GTGATTTTTTCAGGTGGCGATCCTTTAATGGCGAAAGATCACGAATTAGCGTGGTTAATA
541 AAACATTTGGAAAATATACCGCACTTACAACGTTTGCGTATTCACACCCGTTTGCCTGTT
601 GTGATTCCGCAACGGATTACTGATGAATTTTGCACTTTATTAGCAGAAACTCGTTTGCAA
661 ACAGTTATGGTGACACACATTAATCACCCGAATGAAATTGATCAAATTTTTGCTCATGCG
721 ATGCAAAAATTAAACGCCGTGAATGTCACGCTTTTGAATCAATCTGTTTTGCTAAAAGGC
781 GTGAATGATGATGCGCAAATTCTAAAAATATTGAGCGATAAACTTTTTCAAACAGGCATT
841 TTGCCTTATTACTTGCATTTGCTGGATAAAGTTCAAGGGGCGAGCCATTTTTTGATTAGC
901 GATATTGAAGCTATGCAAATCTATAAAACCTTGCAATCTCTGACTTCTGGCTATCTTGTT
961 CCTAAACTTGCACGAGAAATTGCGGGCGAGCCAAATAAGACTTTATACGCAGAATAA

1 MRILPQEPVIREEQNWLTILKNAISDPKLLLKALNLPEDDFEQSIAARKL
 51 FSLRVPQPFIDKIEKGNPQDPLFLQVMCSDLEFVQAEGFSTDPLEEKNAN
101 AVPNILHKYRNRLLFMAKGGCAVNCRYCFRRHFPYDENPGNKKSWQLALD
151 YIAAHSEIEEVIFSGGDPLMAKDHELAWLIKHLENIPHLQRLRIHTRLPV
201 VIPQRITDEFCTLLAETRLQTVMVTHINHPNEIDQIFAHAMQKLNAVNVT
251 LLNQSVLLKGVNDDAQILKILSDKLFQTGILPYYLHLLDKVQGASHFLIS
301 DIEAMQIYKTLQSLTSGYLVPKLAREIAGEPNKTLYAE
```

The nucleotide and amino acid sequences (SEQ ID NOs: 7 and 8) of the *P. gingivalis* polypeptide are:

```
  1 ATGGCAGAAA GTCGTAGAAA GTATTATTTC CCTGATGTCA CCGATGAGCA
 51 ATGGAACGAC TGGCATTGGC AGGTCCTCAA TCGAATTGAG ACGCTCGACC
101 AGCTGAAAAA GTACGTTACA CTCACCGCTG AAGAAGAAGA GGGAGTAAAA
151 GAATCGCTCA AAGTACTCCG AATGGCTATC ACACCTTATT ATTTGAGTTT
151 GAATCGCTCA AAGTACTCCG AATGGCTATC ACACCTTATT ATTTGAGTTT
201 GATAGACCCC GAGAATCCTA ATTGTCCGAT TCGTAAACAA GCCATTCCTA
251 CTCATCAGGA ACTGGTACGT GCTCCTGAAG ATCAGGTAGA CCCACTTAGT
301 GAAGATGAAG ATTCGCCCGT ACCCGGACTG ACTCATCGTT ATCCGGATCG
351 TGTATTGTTC CTTATCACGG ACAAATGTTC GATGTACTGT CGTCATTGTA
401 CTCGCCGTCG CTTCGCAGGA CAGAAAGATG CTTCTTCTCC TTCTGAGCGC
451 ATCGATCGAT GCATTGACTA TATAGCCAAT ACACCGACAG TCCGCGATGT
```

```
-continued
 501 TTTGCTATCG GGAGGCGATG CCCTCCTTGT CAGCGACGAA CGCTTGGAAT

551 ACATATTGAA GCGTCTGCGC GAAATACCTC ATGTGGAGAT TGTTCGTATA

601 GGAAGCCGTA CGCCGGTAGT CCTTCCTCAG CGTATAACGC CTCAATTGGT

651 GGATATGCTC AAAAAATATC ATCCGGTGTG GCTGAACACT CACTTCAACC

701 ACCCGAATGA AGTTACCGAA GAAGCAGTAG AGGCTTGTGA AAGAATGGCC

751 AATGCCGGTA TTCCGTTGGG TAACCAAACG GTTTTATTGC GTGGAATCAA

801 TGATTGTACA CATGTGATGA AGAGATTGGT ACATTTGCTG GTAAAGATGC

851 GTGTGCGTCC TTACTATATA TATGTATGCG ATCTTTCGCT TGGAATAGGT

901 CATTTCCGCA CGCCGGTATC TAAAGGAATC GAAATTATCG AAAATTTGCG

951 CGGACACACC TCGGGCTATG CTGTTCCTAC CTTTGTGGTA GATGCTCCGG

1001 GGGGTGGTGG TAAGATACCT GTAATGCCGA ACTATGTTGT ATCTCAGTCC

1051 CCACGACATG TGGTTCTTCG CAATTATGAA GGTGTTATCA CAACCTATAC

1101 GGAGCCGGAG AATTATCATG AGGAGTGTGA TTGTGAGGAC TGTCGAGCCG

1151 GTAAGCATAA AGAGGGTGTA GCTGCACTTT CCGGAGGTCA GCAGTTGGCT

1201 ATCGAGCCTT CCGACTTAGC TCGCAAAAAA CGCAAGTTTG ATAAGAACTG

1251 A

1 MAESRRKYYF PDVTDEQWND WHWQVLNRIE TLDQLKKYVT LTAEEEEGVK

51 ESLKVLRMAI TPYYLSLIDP ENPNCPIRKQ AIPTHQELVR APEDQVDPLS

101 EDEDSPVPGL THRYPDRVLF LITDKCSMYC RHCTRRRFAG QKDASSPSER

151 IDRCIDYIAN TPTVRDVLLS GGDALLVSDE RLEYILKRLR EIPHVEIVRI

201 GSRTPVVLPQ RITPQLVDML KKYHPVWLNT HFNHPNEVTE EAVEACERMA

251 NAGIPLGNQT VLLRGINDCT HVMKRLVHLL VKMRVRPYYI YVCDLSLGIG

301 HFRTPVSKGI EIIENLRGHT SGYAVPTFVV DAPGGGGKIP VMPNYVVSQS

351 PRHVVLRNYE GVITTYTEPE NYHEECDCED CRAGKHKEGV AALSGGQQLA

401 IEPSDLARKK RKFDKN
```

The nucleotide and amino acid sequences (SEQ ID NOs: 9 and 10) of the *B. subtilus* polypeptide are:

```
   1 TTGAAAAACA AATGGTATAA ACCGAAACGG CATTGGAAGG AGATCGAGTT

51 ATGGAAGGAC GTTCCGGAAG AGAAATGGAA CGATTGGCTT TGGCAGCTGA

101 CACACACTGT AAGAACGTTA GATGATTTAA AGAAAGTCAT TAATCTGACC

151 GAGGATGAAG AGGAAGGCGT CAGAATTTCT ACCAAAACGA TCCCCTTAAA

201 TATTACACCT TACTATGCTT CTTTAATGGA CCCCGACAAT CCGAGATGCC

251 CGGTACGCAT GCAGTCTGTG CCGCTTTCTG AAGAAATGCA CAAAACAAAA

301 TACGATCTGG AAGACCCGCT TCATGAGGAT GAAGATTCAC CGGTACCCGG

351 TCTGACACAC CGCTATCCCG ACCGTGTGCT GTTTCTTGTC ACGAATCAAT

401 GTTCCATGTA CTGCCGCTAC TGCACAAGAA GGCGCTTTTC CGGACAAATC

451 GGAATGGGCG TCCCCAAAAA ACAGCTTGAT GCTGCAATTG CTTATATCCG

501 GGAAACACCC GAAATCCGCG ATTGTTTAAT TTCAGGCGGT GATGGGCTGC

551 TCATCAACGA CCAAATTTTA GAATATATTT TAAAAGAGCT GCGCAGCATT
```

```
 601 CCGCATCTGG AAGTCATCAG AATCGGAACA AGAGCTCCCG TCGTCTTTCC
 651 GCAGCGCATT ACCGATCATC TGTGCGAGAT ATTGAAAAAA TATCATCCGG
 701 TCTGGCTGAA CACCCATTTT AACACAAGCA TCGAAATGAC AGAAGAATCC
 751 GTTGAGGCAT GTGAAAAGCT GGTGAACGCG GGAGTGCCGG TCGGAAATCA
 801 GGCTGTCGTA TTAGCAGGTA TTAATGATTC GGTTCCAATT ATGAAAAAGC
 851 TCATGCATGA CTTGGTAAAA ATCAGAGTCC GTCCTTATTA TATTTACCAA
 901 TGTGATCTGT CAGAAGGAAT AGGGCATTTC AGAGCTCCTG TTTCCAAAGG
 951 TTTGGAGATC ATTGAAGGGC TGAGAGGTCA TACCTCAGGC TATGCGGTTC
1001 CTACCTTTGT CGTTGACGCA CCAGGCGGAG GAGGTAAAAT CGCCCTGCAG
1051 CCAAACTATG TCCTGTCACA AAGTCCTGAC AAAGTGATCT TAAGAAATTT
1101 TGAAGGTGTG ATTACGTCAT ATCCGGAACC AGAGAATTAT ATCCCCAATC
1151 AGGCAGACGC CTATTTTGAG TCCGTTTTCC CTGAAACCGC TGACAAAAAG
1201 GAGCCGATCG GGCTGAGTGC CATTTTTGCT GACAAAGAAG TTTCGTTTAC
1251 ACCTGAAAAT GTAGACAGAA TCAAAAGGAG AGAGGCATAC ATCGCAAATC
1301 CGGAGCATGA AACATTAAAA GATCGGCGTG AGAAAAGAGA TCAGCTCAAA
1351 GAAAAGAAAT TTTTGGCGCA GCAGAAAAAA CAGAAAGAGA CTGAATGCGG
1401 AGGGGATTCT TCATGA

1 LKNKWYKPKR HWKEIELWKD VPEEKWNDWL WQLTHTVRTL DDLKKVINLT
  51 EDEEEGVRIS TKTIPLNITP YYASLMDPDN PRCPVRMQSV PLSEEMHKTK
 101 YDLEDPLHED EDSPVPGLTH RYPDRVLFLV TNQCSMYCRY CTRRRFSGQI
 151 GMGVPKKQLD AAIAYIRETP EIRCDLISGG DGLLINDQIL EYILKELRSI
 201 PHLEVIRIGT RAPVVFPQRI TDHLCEILKK YHPVWLNTHF NTSIEMTEES
 251 VEACEKLVNA GVPVGNQAVV LAGINDSVPI MKKLMHDLVK IRVRPYYIYQ
 301 CDLSEGIGHF RAPVSKGLEI IEGLRGHTSG YAVPTFVVDA PGGGGKIALQ
 351 PNYVLSQSPD KVILRNFEGV ITSYPEPENY IPNQADAYFE SVFPETADKK
 401 EPIGLSAIFA DKEVSFTPEN VDRIKRREAY IANPEHETLK DRREKRDQLK
 451 EKKFLAQQKK QKETECGGDS S
```

The nucleotide and amino acid sequences (SEQ ID NOs: 11 and 12) of the *D. radiodurans* polypeptide are:

```
   1 TGGCAAGGCG TACCCGACGA GCAGTGGTAC GACTGGAAAT GGCAGCTCAA
  51 GAACCGCATC AACAGTGTGG AGGAGTTGCA GGAAGTCCTG ACCCTCACCG
 101 AGTCCGAGTA CCGGGGTGCG TCCGCCGAGG GCATTTTCCG CCTCGACATC
 151 ACGCCGTATT TCGCGTCCCT CATGGACCCC GAAGACCCCA CCTGCCCGGT
 201 GCGCCGTCAG GTGATTCCCA CCGAGGAGGA GCTCCAGCCG TTCACCTCCA
 251 TGATGGAAGA CTCTCTCGCG GAGGATAAGC ACTCGCCCGT GCCGGGGCTG
 301 GTGCACCGCT ACCCCGACCG CGTGCTGATG CTGGTCACGA CCCAGTGCGC
 351 GAGCTACTGC CGCTACTGCA CCCGAAGCCG CATCGTGGGC GACCCCACCG
 401 AGACGTTCAA TCCCGCCGAG TATGAGGCGC AGCTCAACTA CCTGCGCAAC
```

-continued

```
 451 ACCCCGCAGG TGCGCGACGT GCTGCTTTCC GGCGGCGACC CGCTCACACT
 501 CGCGCCGAAG GTGCTGGGGC GCCTGCTTTC CGAACTTCGT AAAATCGAGC
 551 ACATCGAAAT CATCCGCATC GGCACCCGCG TGCCCGTGTT CATGCCCATG
 601 CGCGTGACCC AGGAACTGTG CGACACGCTC GCCAACACC ATCCGCTGTG
 651 GATGAACATT CACGTCAACC ACCCCAAGGA AATCACCCCC GAAGTGGCCG
 701 AGGCGTGTGA CCGTCTGACC CGCGCGGGCG TGCCGCTCGG CAACCAGAGC
 751 GTGCTGCTGC GCGGCGTGAA CGACCACCCG GTCATCATGC AAAAGCTGCT
 801 GCGCGAGCTC GTCAAAATTC GGGTGCGCCC CTACTACATC TACCAGTGCG
 851 ACCTCGTGCA CGGCGCTGGG CACCTGCGCA CCACGGTCAG TAAGGGTCTG
 901 GAAATCATGG AATCGCTGCG CGGCCACACC TCCGGCTACA GCGTGCCGAC
 951 CTACGTGGTG GACGCGCCCG GCGGCGGCGG CAAGATTCCG GTGGCGCCCA
1001 ACTACGTGCT CTCGCACAGC CCTGAGAAGC TGATTCTGCG CAACTTCGAG
1051 GGCTACATCG CCGCCTACTC GGAGCCCACC GATTACACCG GCCCCGACAT
1101 GGCGATTCCT GACGACTGGA TTCGCAAGGA ACCCGGCCAG ACCGGCATCT
1151 TCGGCCTGAT GGAAGGCGAG CGCATTTCCA TCGAGCCA

1 WQGVPDEQWY DWKWQLKNRI NSVEELQEVL TLTESEYRGA SAEGIFRLDI
  51 TPYFASLMDP EDPTCPVRRQ VIPTEEELQP FTSMMEDSLA EDKHSPVPGL
 101 VHRYPDRVLM LVTTQCASYC RYCTRSRIVG DPTETFNPAE YEAQLNYLRN
 151 TPQVRDVLLS GGDPLTLAPK VLGRLLSELR KIEHIEIIRI GTRVPVFMPM
 201 RVTQELCDTL AEHHPLWMNI HVNHPKEITP EVAEACDRLT RAGVPLGNQS
 251 VLLRGVNDHP VIMQKLLREL VKIRVRPYYI YQCDLVHGAG HLRTTVSKGL
 301 EIMESLRGHT SGYSVPTYVV DAPGGGGKIP VAPNYVLSHS PEKLILRNFE
 351 GYIAAYSEPT DYTGPDMAIP DDWIRKEPGQ TGIFGLMEGE RISIEP
```

The nucleotide and amino acid sequences (SEQ ID NOs: 13 and 14) of the *A. aeolicus* polypeptide are:

```
   1 ATGCGTCGCT TTTTTGAGAA TGTACCGGAA AACCTCTGGA GGAGCTACGA
  51 GTGGCAGATA CAAAACAGGA TAAAAACTCT TAAGGAGATA AAAAAGTACT
 101 TAAAACTCCT TCCCGAGGAG GAAGAAGGAA TTAAAAGAAC TCAAGGGCTT
 151 TATCCCTTTG CGATAACACC TTACTACCTC TCTTTAATAA ATCCAGAGGA
 201 CCCGAAGGAT CCTATAAGAC TTCAGGCAAT CCCCCGCGTT GTAGAAGTTG
 251 ATGAAAAGGT TCAGTCTGCG GGAGAACCAG ACGCTCTGAA AGAAGAAGGA
 301 GATATTCCGG TCTTACACA CAGGTATCCC GACAGGGTTC TTTTAAACGT
 351 CACTACCTTT TGTGCGGTTT ACTGCAGGCA CTGTATGAGA AAGAGGATAT
 401 TCTCTCAGGG TGAGAGGGCA AGGACTAAAG AGGAAATAGA CACGATGATT
 451 GATTACATAA AGAGACACGA AGAGATAAGG GATGTCTTAA TTTCAGGTGG
 501 TGAGCCACTT TCCCTTTCCT TGGAAAAACT TGAATACTTA CTCTCAAGGT
 551 TAAGGGAAAT AAAACACGTG GAAATTATAC GCTTTGGGAC GAGGCTTCCC
 601 GTTCTTGCAC CCCAGAGGTT CTTTAACGAT AAACTTCTGG ACATACTGGA
 651 AAAATACTCC CCCATATGGA TAAACACTCA CTTCAACCAT CCGAATGAGA
```

-continued

```
 701 TAACCGAGTA CGCGGAAGAA GCGGTGGACA GGCTCCTGAG AAGGGGCATT
 751 CCCGTGAACA ACCAGACAGT CCTACTTAAA GGCGTAAACG ACGACCCTGA
 801 AGTTATGCTA AAACTCTTTA GAAAACTTTT AAGGATAAAG GTAAAGCCCC
 851 AGTACCTCTT TCACTGCGAC CCGATAAAGG GAGCGGTTCA CTTTAGGACT
 901 ACGATAGACA AAGGACTTGA AATAATGAGA TATTTGAGGG GAAGGCTGAG
 951 CGGTTTCGGG ATACCCACTT ACGCGGTGGA CCTCCCGGGA GGGAAAGGTA
1001 AGGTTCCTCT TCTTCCCAAC TACGTAAAGA AAAGGAAAGG TAATAAGTTC
1051 TGGTTTGAAA GTTTCACGGG TGAGGTCGTA GAATACGAAG TAACGGAAGT
1101 ATGGGAACCT TGA

1 MRRFFENVPE NLWRSYEWWQI QNRIKTLKEI KKYLKLLPEE EEGIKRTQGL
  51 YPFAITPYYL SLINPEDPKD PIRLQAIPRV VEVDEKVQSA GEPDALKEEG
 101 DIPGLTHRYP DRVLLNVTTF CAVYCRHCMR KRIFSQGERA RTKEEIDTMI
 151 DYIKRHEEIR DVLISGGEPL SLSLEKLEYL LSRLREIKHV EIIRFGTRLP
 201 VLAPQRFFND KLLDILEKYS PIWINTHFNH PNEITEYAEE AVDRLLRRGI
 251 PVNNQTVLLK GVNDDPEVML KLFRKLLRIK VKPQYLFHCD PIKGAVHFRT
 301 TIDKGLEIMR YLRGRLSGFG IPTYAVDLPG GKGKVPLLPN YVKKRKGNKF
 351 WFESFTGEVV EYEVTEVWEP
```

The nucleotide and amino acid sequences (SEQ ID NOs: 15 and 16) of the *T. pallidum* polypeptide are:

```
   1 GTGTCTATGG CTGAGTGTAC CCGGGAACAG AGAAAGAGAC GAGGTGCAGG
  51 GCGTGCTGAT GAGCATTGGC GGACGTTGAG TCCTGCCTGT TGCGCGGCAG
 101 ATGCGCTGAC GGAGCATATT TCTCCAGCGT ATGCGCATTT AATTGCACAA
 151 GCGCAGGGCG CGGACGCGCA GGCGCTGAAA CGTCAGGTGT GCTTTGCGCC
 201 ACAGGAGCGT GTGGTGCATG CTTGCGAGTG TGCCGACCCA TTGGGTGAGG
 251 ACCGGTACTG CGTGACACCC TTTTTGGTGC ATCAGTATGC GAATCGTGTG
 301 TTGATGTTGG CAACAGGACG TTGCTTTTCA CACTGTCGCT ATTGTTTTCG
 351 CCGCGGTTTC ATCGCCCAAC GTGCAGGGTG GATCCCCAAC GAAGAGCGCG
 401 AGAAGATTAT TACGTATCTT CGTGCTACCC CTTCGGTGAA GGAAATCCTG
 451 GTTTCAGGTG GTGATCCACT CACTGGTTCT TTTGCACAGG TCACATCGCT
 501 TTTCCGCGCA CTGCGCAGTG TAGCGCCGGA TTTGATTATT CGTCTGTGCA
 551 CTCGCGCAGT CACCTTTGCT CCGCAGGCCT TTACTCCCGA GCTGATTGCG
 601 TTTCTGCAGG AGATGAAGCC GGTGTGGATA ATTCCGCATA TTAATCACCC
 651 GGCAGAGCTC GGTTCTACGC AGCGCGCGGT GCTCGAGGCC TGCGTAGGCG
 701 CAGGCCTCCC TGTGCAATCG CAGTCGGTAC TGTTGCGCGG GGTGAACGAT
 751 TCGGTAGAGA CGCTGTGCAC ACTGTTTCAC GCGCTCACTT GTCTGGGGGT
 801 TAAGCCGGGG TATCTATTTC AGTTGGATTT GGCGCCTGGA ACTGGGGATT
 851 TTCGTGTGCC ACTTTCTGAC ACGCTAGCTC TGTGGCGCAC ATTGAAGGAG
 901 CGCCTCTCAG GGTTGTCGCT TCCCACGCTT GCGGTGGACT TGCCAGGGGG
```

```
-continued
 951 TGGAGGAAAG TTTCCGCTTG TGGCATTGGC CTTGCAGCAA GATGTCACGT

1001 GGCATCAGGA ACGCGAGGCG TTCTCCGCAC GCGGCATCGA TGGCGCGTGG

1051 TACACGTACC CGTTC

1 VSMAECTREQ RKRRGAGRAD EHWRTLSPAS CAADALTEHI SPAYAHLIAQ

51 AQGADAQALK RQVCFAPQER VVHACECADP LGEDRYCVTP FLVHQYANRV

101 LMLATGRCFS HCRYCFRRGF IAQRAGWIPN EEREKIITYL RATPSVKEIL

151 VSGGDPLTGS FAQVTSLFRA LRSVAPDLII RLCTRAVTFA PQAFTPELIA

201 FLQEMKPVWI IPHINHPAEL GSTQRAVLEA CVGAGLPVQS QSVLLRGVND

251 SVETLCTLFH ALTCLGVKPG YLFQLDLAPG TGDREVPLSD TLALWRTLKE

301 RLSGLSLPTL AVDLPGGGGK FPLVALALQQ DVTWHQEREA FSARGIDGAW

351 YTYPF
```

Thus, the present invention contemplates the use of clostridial enzyme sequences to identify lysine 2,3-aminomutase from other species. The present invention further contemplates variants of such lysine 2,3-aminomutases, and the use of such enzymes to prepare β-amino acids.

In one screening approach, polynucleotide molecules having nucleotide sequences disclosed herein can be used to screen genomic or cDNA libraries. Screening can be performed with clostridial lysine 2,3-aminomutase polynucleotides that are either DNA or RNA molecules, using standard techniques. See, for example, Ausubel et al. (eds.), SHORT PROTOCOLS IN MOLECULAR BIOLOGY, pages 6-1 to 6-11 (John Wiley & Sons, Inc. 1995). Genomic and cDNA libraries can be prepared using well-known methods. See, for example, Ausubel et al. (eds.), SHORT PROTOCOLS IN MOLECULAR BIOLOGY, pages 5-1 to 5-6 (John Wiley & Sons, Inc. 1995).

Additional lysine 2,3-aminomutase genes can also be obtained using the polymerase chain reaction (PCR) with oligonucleotide primers having nucleotide sequences that are based upon the nucleotide sequences of the lysine 2,3-aminomutase genes of Clostridium, Porphyromonas, Bacillus, Deinococcus, Aquifex, Teponema, Haemophilus or Escherichia, as described herein. General methods for screening libraries with PCR are provided by, for example, Yu et al, "Use of the Polymerase Chain Reaction to Screen Phage Libraries," in METHODS IN MOLECULAR BIOLOGY, Vol. 15: PCR PROTOCOLS: CURRENT METHODS AND APPLICATIONS, White (ed.), pages 211-215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in METHODS IN MOLECULAR BIOLOGY, Vol. 15: PCR PROTOCOLS: CURRENT METHODS AND APPLICATIONS, White (ed.), pages 317-337 (Humana Press, Inc. 1993).

In one instance, the gene from Bacillus subtilus (SEQ ID NO:9) was isolated from chromosomal DNA by PCR generating an oligonucleotide insert which after the appropriate restriction digestion was cloned into the NdeI and XhoI site of pET23a(+) expression vector (Novagen, Inc., Madison, Wis.). This plasmid construct when placed into E. coli BL21 (DE3) cells (Novagen, Inc., Madison, Wis.) and expressed by induction with 1 mM isopropyl-β-thiogalactopyranoside (IPTG) produced cell extracts exhibiting lysine 2,3-aminomutase activity. Cell extracts from control BL21 (DE3) cells which contained the pET23a(+) vector without the B. subtilus gene and cultured as above demonstrated no measurable lysine 2,3-aminomutase activity.

Anti-lysine 2,3-aminomutase antibodies can also be used to isolate DNA sequences that encode enzymes from cDNA libraries. For example, the antibodies can be used to screen λgt11 expression libraries, or the antibodies can be used for immunoscreening following hybrid selection and translation. See, for example, Ausubel et al. (eds.), SHORT PROTOCOLS IN MOLECULAR BIOLOGY, 3rd Edition, pages 6-12 to 6-16 (John Wiley & Sons, Inc. 1995); and Margolis et al., "Screening λ expression libraries with antibody and protein probes," in DNA CLONING 2: EXPRESSION SYSTEMS, 2nd Edition, Glover et al. (eds.), pages 1-14 (Oxford University Press 1995).

Furthermore, the identification of lysine 2,3-aminomutases is simplified by using known conserved regions in the DNA sequences of genes encoding the enzymes. By matching the conserved sequences with potential lysine 2,3-aminomutases, positive identification can be achieved. These conserved sequences include CXXXCRXCXR (SEQ ID NO:33)-the iron sulfur center residues; S(T)GGD(E) (SEQ ID NO:34)-S-adenosyl-L-methionine binding domain, and P(A,G)G(S)XXXKT(I,V,F) (SEQ ID NO:35)-pyridoxal 5'-phosphate binding domain.

6. The Use of Lysine 2,3-Aminomutase to Produce β-Amino Acids

A. Production of L-β-Lysine Using Purified Enzyme

Recombinant lysine 2,3-aminomutase can be purified from host cells as described above, and used to prepare enantiomerically pure β-amino acids. An "enantiomerically pure" β-amino acid comprises at least 87% β-amino acid. Enantiomerically pure β-amino acid can be prepared in batchwise reactors using soluble lysine 2,3-aminomutase. The lysine 2,3-aminomutase can then be mixed with the required cofactors: (1) ferrous sulfate or ferric ammonium sulfate; (2) pyridoxal phosphate; (3) dehydrolipoic acid, glutathione, or dithiothreitol; (4) S-adenosylmethionine; and (5) sodium dithionite, and the appropriate α-amino acid at pH 8 or other appropriate pH at a temperature between 25° C. to 37° C., until the production of the β-amino acid is at equilibrium.

Alternatively, enatiomerically pure β-amino acid can be obtained by continuous processing using immobilized lysine 2,3-aminomutase. Lysine 2,3-aminomutase can be packed in a column and activated by the addition of cofactors and a solution containing α-amino acid at pH 8 or other appropriate pH can be passed through the column at a rate that allows completion of the reaction during contact with the enzyme. The effluent from the column will contain the β-amino acid.

Both of the above methods will produce an equilibrium mixture of α-amino acid and β-amino acid in which the predominant species is β-amino acid. The ratio of β-amino acid to α-amino acid after processing is 7:1 when performed at pH 8 at 37° C., producing enantiomerically pure β-amino acid. Chirpich et al., *J. Biol. Chem.* 245:1778 (1970). If higher purity of β-amino acid is desired, the α-amino acid can be separated from the β-amino acid by any number of means well known in the art, including high performance chromatography procedures, such as ion exchange chromatography at an appropriate pH to take advantage of the differences in acidities of the carboxylic acid groups and the α- and β-ammonium groups.

B. Production of β-Amino Acid Using Recombinant Host Cells

In an alternative approach, β-amino acid is produced by fermentation using recombinant host cells that over-express cloned lysine 2,3-aminomutase. General methods for high level production of amino acids from cultured bacteria are well-known to those of skill in the art. See, for example, Daugulis, *Curr. Opin. Biotechnol.* 5:192 (1994); Lee, *TIBTECH* 14:98 (1996).

The gene for lysine 2,3-aminomutase can be incorporated into an *E. coli* plasmid that carries necessary markers and *E. coli* regulatory elements for overexpression of genes. When codon usage for the lysine 2,3-aminomutase gene cloned from *Clostridia* is inappropriate for expression in *E. coli*, the host cells can be cotransformed with vectors that encode species of tRNA that are rare in *E. coli* but are frequently used by *Clostridia*. For example, cotransfection of the gene dnaY, encoding tRNA$^{ArgAGA/AGG}$, a rare species of tRNA in *E. coli*, can lead to high-level expression of heterologous genes in *E. coli*. Brinkmann et al., *Gene* 85:109 (1989) and Kane, *Curr. Opin. Biotechnol.* 6:494 (1995). Heterologous host cells expressing lysine 2,3-aminomutase can be cultured with favorable energy, carbon and nitrogen sources under conditions in which α-amino acid in the medium is absorbed by the cells and converted intracellularly into β-amino acid by lysine 2,3-aminomutase. Unused β-amino acid will be excreted into the growth medium. β-amino acid can then be purified from the medium by any methods well known in the art, including high performance chromatography procedures previously described.

The present invention, thus generally described, will be understood more readily by reference to the following examples, which are provided by way of illustration and are not intended to be limiting of the present invention.

EXAMPLE 1

Isolation of Clostridial Lysine 2,3-Aminomutase Gene

Lysine 2,3-aminomutase was purified from *Clostridia subterminale* SB4 cells (American Type Culture Collection, Rockville, Md.) according to the procedure of Moss and Frey, J. Biol. Chem. 265:18112 (1990), as modified by Petrovich et al., J. Biol. Chem. 226:7656 (1991). The purified protein (200 μM - subunit concentration) was dialyzed overnight (1 vol. protein to 1000 vol. 1 mM NaCl) and lyophilized to dryness under vacuum.

The dried lysine 2,3-aminomutase was resuspended to the original volume in 6M guanidine hydrochloride+0.25 M tris (hydroxymethyl)aminomethane (Tris-HCl) pH 8.5+1 mM ethylenediaminetetraacetic acid (EDTA). The protein was then reduced with dithiothreitol (DTT) (5 fold molar excess of DTT over cysteine residues) for 3 hours at 25° C. under argon atmosphere and alkylated with 4-vinylpyridine (Aldrich Chemical Co., Milwaukee, Wis.) (20 fold molar excess over DTT) for 90 minutes at 25° C. The protein sample was dialyzed against distilled water (1 vol. protein to 1000 vol. water) overnight at 4° C., then lyophilized to dryness. The dried protein was dissolved in 0.1 N hydrochloric acid (HCl) and subjected to cyanogen bromide (Aldrich Chemical Co., Milwaukee, Wis.) cleavage by the addition of 100 fold molar excess of cyanogen bromide to methionine residues under argon gas for 24 hours at 25° C. The sample was dried by Speed-Vac (Savant Instruments, Inc., Hicksville, N.Y.) under vacuum and redissolved in 6M guanidine hydrochloride.

Cyanogen bromide treatment of proteins produces peptide bond cleavage at the C-terminus side of methionine residues. In the process, cyanogen bromide reacts with the sulfur atom of the thioether side chain of methionine to produce homoserine (Practical Protein Chemistry, Wiley, N.Y., (1986) pp. 83-88). Cyanogen bromide treatment of lysine 2,3-aminomutase produced 8 major polypeptides. These polypeptides were separated from each other using high pressure liquid chromatography (HPLC) and a Vydac $C_4$ reverse phase column (Vydac 214TP54, 5 M, 4.6×250 mm, The Separations Group, Hesperia, Calif.). The polypeptides were first separated into five main groups using a linear gradient of 0-80% acetonitrile in 0.1% trifluoroacetic acid (TFA) in water over 60 minutes at a flow rate of 1 ml/min. at room temperature. The individual fractions were collected, dried by Speed-Vac under vacuum, reinjected into the same column and eluted with a narrow linear gradient of acetonitrile in 0.1% TFA. Five individual gradients were used to separate 8 polypeptides.

The following linear gradients of acetonitrile in 0.1% trifluoroacetic acid in water at 1 ml/min were used: peptide 1—(5-20% 1 hr.); peptide 2—(5-25% 1 hr.); peptide 3a—(30-42% 6 hr.); peptide 3b—(30-42% 6 hr.); peptide 4a—(33-50% 6 hr.); peptide 4b—(33-42% 6 hr.); peptide 4c—(33-42% 6 hr.); peptide 5 (45-55% 6 hr.). All peptides except peptide 3a were represented as single peaks on the chromatogram when detected at 210 nm. Peptide 3a represented approximately five unresolved peaks on the chromatogram even when the narrow elution gradient was applied. Subsequent analysis of peptide 3a by electrospray mass spectrometry (UW Biotechnology Department, Madison, Wis.) indicated only one peptide species of molecular weight of 6664 Da. Thus the multiple peaks observed by HPLC were the result of chromatographic artifact.

Each polypeptide fraction was analyzed for homoserine by acid (HCl) hydrolysis of the peptide, derivatization of the amino acids produced by reaction with phenylisothiocyanate, and separation and quantification of individual amino acids. Samples collected from HPLC were dried by Speed-Vac. Each peptide was dissolved in 6N HCl, placed in a vacuum hydrolysis tube (1 ml, 8×60 mm, Pierce Chemical, Rockford, Ill.), placed under vacuum, and incubated at 110° C. for 24 hours. Following hydrolysis, the samples were dried by Speed-Vac. Derivatization, separation, and quantification of amino acids were conducted according to Heinrikson et al., Anal. Biochem. 136:65 (1984). One peptide fraction containing a low level of homoserine (peptide 3a) was tentatively identified as the C-terminus peptide.

The complete protein and peptide 3a were each sequenced 12-16 amino acids downstream from the N-terminus (Michigan State University, Department of Biochemistry, Macromolecular Facility, East Lansing, Mich.). The amino acid sequence information was used to design degenerate oligonucleotides at the N-terminus region of the whole protein and the N-terminus region of peptide 3a which served as primers for polymerase chain reaction (PCR). The N-terminus amino acid sequence of the complete protein used for primer design was: (SEQ ID NO: 17) KDVSDA corresponding to the (+) DNA strand (SEQ ID NO: 18) 5'-AARGAYGTIWSI-GAYGC-3' where I=INOSINE, S=G+C, W=A+T, Y=C+T, D=G+A+T, R=A+G. The N-terminus amino acid sequence of peptide 3a used for primer design was: (SEQ ID NO: 19) QSHDKV corresponding to the opposite (−) strand (SEQ ID NO: 20) 5'-ATIACYTTRTCRTGISWYTG-3' where I=INOSINE, Y=C+T, R=A+G, S=G+C, W=A+T.

PCR was subsequently used to generate an oligonucleotide of 1029 bases which when cloned and sequenced represented approximately 82 per cent of the entire gene of 1251 bases for lysine 2,3-aminomutase. PCR was conducted in the following manner. Chromosomal DNA from *Clostridium subterminale* SB4 was prepared and purified utilizing a commercially available kit: Qiagen Genomic Tip 500/G #13343 (Qiagen, Inc., Santa Clarita, Calif.). After ethanol precipitation, the genomic DNA was resuspended in TE (pH 8.0) buffer (10 mM Tris-HCl pH 8.0+1 mM EDTA). The PCR reaction mixture (100 μl total volume) contained: *Clostridium subterminale* SB4 chromosomal DNA—2 μg; low salt PCR buffer (Stratagene, La Jolla, Calif.); dNTPs—0.2 mM; oligonucleotide primers—10 μM each; Taq Plus Long DNA Polymerase (Stratagene)—5 units. All samples were overlayered with 100 μl mineral oil and subjected to 35 cycles of 1 min. at 94° C., 30 sec. at 37° C., 15 sec. at 50° C., and 3 min. at 72° C. After thermocycling, DNA formed during the PCR process was purified by agarose electrophoresis (2% agarose, Promega Corp., Madison, Wis.) in TAE buffer (0.04 M Tris-acetate pH 8.0+1 mM EDTA). Following identification and excision of appropriately sized (1 kbase) ethidium bromide stained band, DNA was extracted from the agarose using Genelute Minus EtBr spin column (Supelco, Bellefonte, Pa.), concentrated by precipitation with ethanol and resuspended in TE pH 8.0 buffer.

DNA obtained from PCR was cloned directly into the pCR2.1 vector (TA Cloning Kit #K2000-01, Invitrogen Corp., San Diego, Calif.) according to manufacturer's procedure. Either 12.8 ng or 38.4 ng of PCR insert was ligated to 50 ng pCR2.1 vector overnight at 14° C. Competent *E. coli* cells (Top10F' One Shot cells—Invitrogen Corp.) were transformed with ligation mix (either 12 or 36 ng DNA per 50 μl of cells) and white colonies chosen after cells were plated on Luria broth (LB) 10 cm plates (10 gm Difco Bactotryptone, 5 gm Difco Bacto yeast extract, 10 gm NaCl, 15 gm Bactoagar per liter water; Difco Laboratories, Detroit, Mich.) containing carbenicillin (100 μg/ml) (Sigma Chemical Co., St. Louis, Mo.) and overlayered with 40 μl isopropyl-β-thiogalactopyranoside (IPTG) (100 mM) (Promega Corp., Madison, Wis.) and 40 μl 5-bromo-4-chloro-3-indoyl-β-D-galactoside (X-Gal) (40 mg/ml) (Promega Corp.). Selected colonies were cultured in LB (10 gm Difco Bactotryptone, 5 gm Difco Bacto yeast extract, 10 gm NaCl per liter water; Difco Laboratories) with carbenicillin (100 μg/ml) for plasmid DNA purification. Plasmid DNA was isolated by either the Qiagen Plasmid mini or midi kits (Qiagen, Inc.).

The PCR insert was sequenced in both strands beginning at the ligation sites by the radiolabeled dideoxynucleotide Sanger method (Sanger, F. et al., Proc. Natl. Acad. Sci. USA 74:5463 (1977) using T7 Sequenase version 2.0 Sequencing Kit (Amersham Life Science, Arlington Heights, Ill.). The procedure produced a sequence of 1029 base pairs which represented 82 per cent of the entire gene. The remaining unknown sequence of the gene was obtained by preparing a genomic library of *Clostridium subterminale* SB4 chromosomal DNA. Prior to the preparation of the genomic library, additional information was obtained regarding the composition of the peptides obtained from cyanogen bromide treatment of the reduced and alkylated lysine 2,3-aminomutase protein. The molecular weight of the intact protein and the individual peptides (both alkylated) were obtained by electrospray mass spectrometry (UW Biotechnology Dept, Madison, Wis.). The molecular weights obtained were: peptide 1—2352; peptide 2—1875; peptide 3a—6664; peptide 3b—6229; peptide 4a—7768; peptide 4b—7403; peptide 4c—6972; peptide 5—8003. Summation of these molecular weights plus the molecular weights of two small peptides not observed by HPLC but seen from the translated base sequence (MW=216 and 415) and the N-terminus methionine (MW=149) plus the additional mass of replacement of 9 homoserines with 9 methionines (ΔMW=270) and minus ten water molecules (ΔMW=180) gives a calculated molecular weight of 48,136. Within experimental error, the summation of the molecular weights of individual peptides compares with the molecular weight of the reduced and alkylated lysine 2,3-aminomutase protein of 48, 281 obtained by electrospray mass spectrometry.

Comparison of the molecular weights of the peptides from mass spectrometry with the molecular weights of the peptides produced by translation of the known incomplete base sequence (1029 base pairs) of the protein identified all but two of the peptides. These peptides were peptide 3a and peptide 2. Since the N-terminus sequence of peptide 3a had been used for PCR to produce the sequence of 1029 base pairs and all other peptides except peptide 2 had been identified in this known sequence, peptide 2 must be the C-terminus peptide. Both peptides 2 and 3a were subjected to extensive N-terminus amino acid sequence analysis (Michigan State University, Department of Biochemistry, Macromolecular Facility, East Lansing, Mich.). Furthermore, C-terminus amino acid sequence analysis was conducted on the whole protein. For peptide 3a, the N-terminal amino acid sequence reported was: (SEQ ID NO: 21) PNYVISQSHDKVILRNFEGVITTY-SEPINYTPGCNCDVCTGKKKVHKV. For peptide 2, the N-terminal amino acid sequence reported was: (SEQ ID NO: 22) ALEPVGLERNKRHVQ. For the whole protein, the N-terminus amino acid sequence reported was: (SEQ ID NO: 23) MINRRYELFKDVSDAD and the C-terminus amino acid sequence reported was: EQV.

A nondegenerate, nonradioactive probe (500 bases) containing digoxygenin dUMP residues randomly incorporated was prepared by PCR (The PCR DIG PROBE Synthesis kit—#1636-090 Boehringer-Mannheim, Indianapolis, Ind.). The digoxygenin dUMP groups replace thymidine in some of the positions of the DNA. The following primers were used for the PCR Probe Synthesis kit: Primer 1 (+) strand (SEQ ID NO: 24)—5'-ATCCTAACGATCCTAATGATCC; Primer 2 (−) strand (SEQ ID NO: 25)—5'-TGGATGGTTAAAGT-GAGTG. Using as template a plasmid containing the incomplete lysine 2,3-aminomutase gene, the following probe labeled with digoxygenin groups was prepared: (SEQ ID NO: 26) 5'—

(SEQ ID NO:26)
```
5'ATCCTAACGATCCTAATGATCCAGTAAGAAAACAAGCTATTCCAACAGCATTAGAGCTTAACAAAGCTGCTGCA

GATCTTGAAGACCCATTACATGAAGATACAGATTCACCAGTACCTGGATTAACTCACAGATATCCAGATAGAGTAT

TATTATTAATAACTGATATGTGCTCAATGTACTGCAGACACTGTACAAGAAGAAGATTTGCAGGACAAAGCGATGA

CTCTATGCCAATGGAAAGAATAGATAAAGCTATAGATTATATCAGAAATACTCCTCAAGTTAGAGACGTATTATTA

TCAGGTGGAGACGCTCTTTTAGTATCTGATGAAACATTAGAATACATCATAGCTAAATTAAGAGAAATACCACACG

TTGAAATAGTAAGAATAGGTTCAAGAACTCCAGTTGTTCTTCCACAAAGAATAACTCCAGAACTTGTAAATATGCT

TAAAAAATATCATCCAGTATGGTTAAACACTCACTTTAACCATCCA-3'.
```

Primers (1 μM) were used with plasmid template (1 ng) for PCR according to manufacturer's specifications (Boehringer-Mannheim, Indianapolis, Ind.). The PCR product, checked by agarose gel electrophoresis, was used directly in probe analysis.

*Clostridium subterminale* SB4 chromosomal DNA was isolated as described previously and subjected to restriction digestion using several restriction endonucleases. These enzymes did not cut in the region of the known lysine 2,3-aminomutase gene sequence. However, these sites were present in the multicloning region of pUC19 vector. The enzymes used were EcoRI (New England Biolabs, Beverly, Mass.), XbaI (Promega Corp., Madison, Wis.), AccI (New England Biolabs, Beverly, Mass.), and NdeI (Promega Corp., Madison, Wis.). Restriction enzyme (100 units) was reacted with chromosomal DNA (10 μg) and appropriate buffer (manufacturers specification)+0.01% bovine serum albumin for 90 min. at 37° C. in eight replicates. After restriction digestion, each fraction was applied to a preparative agarose gel (14×14 cm) in multiple lanes in TAE buffer (0.04 M Tris-acetate pH 8.0+1 mM EDTA) and subjected to electrophoresis at 150 volts. After electrophoresis, several lanes were separated from the remaining gel for probe analysis, treated with NaOH (0.5 N) solution to denature DNA, neutralized with 0.5 M Tris-HCl buffer pH 7.5, in preparation for blotting by diffusion. To the surface of this gel, nylon membrane (#1209-299 Boehringer-Mannheim, Indianapolis, Ind.) was applied followed by filter paper and a stack of paper towel. After 24 hr., the paper towel was removed and the nylon membrane treated for digoxygenin dUMP labeled probe analysis according to manufacturer's procedure (Boehringer Mannheim, Indianapolis, Ind.). Positive probe-template interaction was identified by chemiluminescence from an anti-digoxygenin antibody conjugate containing alkaline phosphatase and reacting with CDP-Star (disodium 2-chloro-5-(4-methoxyspiro{1,2-dioxetane-3,2'-(5'-chloro) tricyclo [3.3.1.1.]decan}-4-yl)-1-phenyl phosphate), a chemiluminescent substrate (both obtained from Boehringer-Mannheim, Indianapolis, Ind.). The restriction digestion produced fragments of chromosomal DNA showing positive chemiluminescent probe-template interaction of the following sizes: XbaI—4.3 kb, EcoRI—4.5 kb, AccI—5.9 kb, and NdeI—6.1 kb. From this information, the appropriate sized fragments of DNA were cut out of zones of the remaining agarose gel. DNA was extracted from these agarose bands by use of spin columns (GenElute Agarose spin column #5-6500, Supelco, Bellefonte, Pa.) by centrifugation at 12,000×g for 10 min. and concentrated by ethanol precipitation.

Chromosomal DNA fragments were ligated to pUC19 plasmid vector (New England Biolabs, Beverly, Mass.) cut with the same restriction endonuclease and dephosphorylated, transformed into competent *E. coli* XL-2 Blue Ultracompetent cells (#200151, Stratagene, La Jolla, Calif.), and plated on LB agar+carbenicillin+X-Gal+IPTG (as previously described). PUC19 plasmid vector (10 μg) was incubated with respective restriction enzymes (2 units) in appropriate buffer (manufacturer's specification)+0.01% bovine serum albumin for 1 hour at 37° C. Restriction enzyme activity was removed from the medium either by passage through a Micropure EZ Enzyme Spin column (Amicon, Inc., Beverly, Mass.) or by heat inactivation at 65° C. for 20 min. Each restriction digested pUC19 plasmid was dephosphorylated by treatment with 1 unit of calf intestine alkaline phosphatase (Pharmacia Biotech., Piscataway, N.J.) in appropriate buffer (manufacturer's specification) for 30 min. at 37° C. Alkaline phosphatase was removed by using a Micropure EZ Spin column. Plasmid DNA was purified by agarose electrophoresis in TAE buffer (as previously described). After ethidium bromide staining, appropriate size fragments of DNA (approximately 2600 base pairs) were cut out of the agarose. DNA was extracted from the agarose bands with spin columns (GenElute Minus EtBr Spin column, #5-6501, Supelco, Bellefonte, Pa.) by centrifugation at 14,000×g for 20 min. and concentrated by ethanol precipitation.

For ligation, 10 ng of restriction endonuclease cut and alkaline phosphatase dephosphorylated vector was ligated to the following chromosomal DNA inserts to produce a 1:1 or 1:3 ratio of vector DNA to insert DNA: XbaI—16 and 48 ng, EcoRI—17 and 50 ng, AccI—22 and 66 ng, and NdeI—23 and 68 ng each in a total volume of 10 μl. T4 DNA ligase (3 units—Pharmacia Biotech, Piscataway, N.J.) was added to T4 DNA ligase buffer (Promega Corp., Madison, Wis.) and ligation occurred for 16 hours at 14° C. Transformed *E. coli* XL-2 Blue Ultracompetent cells from individual plated white colonies (approximately 500 per trial) were placed on nylon membranes, treated with alkali to expose and denature DNA, and hybridized with the oligonucleotide probe labeled with digoxygenin dUMP (procedures according to manufacturer's specifications, Boehringer-Mannheim, Indianapolis, Ind.). Colonies (1 or 2 per 500) in which the digoxygenin labeled probe demonstrated positive chemiluminescence when examined by X-ray film were chosen for further screening by DNA sequencing. The start codon, ATG, was found in one XbaI colony (X158). The start (ATG) and the stop (TAA) codon were found in one EcoRI colony (E138). Double stranded DNA from these selected colonies were sequenced using the automated ABI Prism Dye Terminator Cycle Sequencing procedure by the University of Wisconsin Biotechnology Department, Madison, Wis. to obtain the final sequence of the *Clostridium subterminale* SB4 gene. The DNA sequence was translated into the amino acid sequence according to the genetic code. Amino acid sequences obtained from N-terminal and C-terminal amino acid analysis of the protein and the cyanogen bromide derived peptides were in perfect agreement with the translated DNA sequence. The molecular weight of the translated sequence of amino acids (47,025) agreed within experimental error with the molecular weight of Clostridial lysine 2,3-aminomutase protein obtained by electrospray mass spectrometry (47,173).

EXAMPLE 2

Incorporation of *Clostridia subterminale* SB4 Lysine 2,3-aminomutase Gene Into *E. coli*

One of the *E. coli* colonies containing the pUC19 plasmid with the nucleotide sequence encoding the entire *Clostridial* lysine 2,3-aminomutase gene from the genomic library (E138) was used to prepare an expression vector. The *Clostridial* lysine 2,3-aminomutase gene was inserted into two commercially available plasmid expression vectors. The plasmid vector, pET-23a(+) (Novagen, Inc., Madison, Wis.) derived from pBR322 contains the T7 promoter as well as the ribosome binding site of the phage T7 major capsid protein upstream from the multi-cloning site. The gene for *Clostridial* lysine 2,3-aminomutase was inserted into the multi-cloning site. This expression system when cloned into a cell line which produces an IPTG (isopropyl-β-thiogalactopyranoside)—inducible T7 RNA polymerase has been reported to yield very high levels of many heterologous gene products (Studier et al., Gene Expression Technology in Methods in Enzymology 185:60 (1991). The plasmid vector, pKK223-3 (Amersham Pharmacia Biotech, Piscataway, N.J.) also derived from pBR322 contains a strong tac promoter upstream from the multiple cloning site and a strong rrnB ribosomal terminator downstream. In lac $I^q$ *E. coli* cells, the tac promoter is inducible with IPTG, although uninduced cells will show a low level of expression of the cloned gene. Both plasmids confer ampicillin resistance to *E. coli* cells.

In order to splice the lysine 2,3-aminomutase gene into the above vectors so that the start codon is correctly spaced from the respective ribosome binding site of the vector, PCR was used to generate inserts which after appropriate restriction digestion could be cloned directly into the multicloning site of each vector. The following primers for PCR were used: for pET-23a(+): (SEQ ID NO: 27) (+) strand 5'-TACACATATGATAAATAGAAGATATG-3', (SEQ ID NO: 28) (−) strand 5'-TAGACTCGAGTTATTCTTGAACGTGTCTC-3'; for pKK223-3, (SEQ ID NO: 29) (+) strand 5'-TACAGAATTCATGATAAATAGAAGATATG-3', (SEQ ID NO: 30) (−) strand 5'-TAGAAAGCTTTTATTCTTGAACGTGTCTC-3'. The DNA template used was the pUC19 plasmid with the nucleotide sequence encoding the entire *Clostridial* lysine 2,3-aminomutase gene from the genomic library (E138). pUC19 plasmid DNA was isolated by the Qiagen Plasmid mini kit (Qiagen, Inc., Santa Clarita, Calif.). PCR was conducted as described previously. The PCR reaction mixture (100 µl total volume) contained: pUC19 plasmid DNA—(400 ng); cloned Pfu DNA polymerase reaction buffer (Stratagene, La Jolla, Calif.); dNTPs—0.2 mM each; oligonucleotide primers—1 µM each; cloned Pfu DNA polymerase (Stratagene, La Jolla, Calif.)—5 units. All samples were overlayered with 100 µl mineral oil and subjected to 35 cycles of 1 min. at 94° C., 30 sec. at 37° C., 15 sec. at 50° C., and 3 min. at 72° C. After thermocycling, DNA formed during the PCR process was further purified by agarose electrophoresis (2% agarose, Promega Corp., Madison, Wis.) in TAE buffer (0.04 M Tris-acetate pH 8.0+1 mM EDTA). Following identification and excision of the appropriately sized (~1.2 kbase) ethidium bromide stained band, DNA was extracted from the agarose using the GenElute Minus EtBr spin column (Supelco, Bellefonte, Pa.), concentrated by precipitation with ethanol, and resuspended in TE pH 8.0 buffer. The purified PCR product was blunt-end ligated to pCR-Script Amp cloning vector (#211188 Stratagene, La Jolla, Calif.) using 0.3 pmoles insert to 0.005 pmoles vector according to manufacturer's specifications. The ligated DNA was used to transform XL1—Blue MRF' *E. coli* cells (Stratagene, La Jolla, Calif.) which were subsequently plated on LB+carbenicillin+IPTG+X-Gal plates (as previously described) and cultured overnight. White colonies were chosen and subcloned in LB+carbenicillin (100 µg/ml) media for plasmid purification.

Plasmid DNA was purified using Qiagen Plasmid mini kit (Qiagen, Inc., Santa Clarita, Calif.) and subjected to restriction digestion. For the pET-23a(+) insert, 10 µg of plasmid DNA was cut with NdeI (Promega Corp. Madison, Wis.)—50 units and Xho I (Promega Corp.)—50 units in a total volume of 100 µl for 1 hr. at 37° C.; for pKK223-3 insert, 10 µg of plasmid DNA was cut with EcoRI (New England Biolabs, Beverly, Mass.)—100 units and HindIII (New England Biolabs)—100 units in a total volume of 100 µl for 90 min. at 37° C. The insert DNA was separated from the plasmid DNA by agarose gel electrophoresis (2% agarose in TAE buffer), purified and concentrated as previously described. The expression vectors, pET-23a(+)—10 µg and pKK223-3—10 µg were similarly cut with NdeI—Xho I and EcoRI-HindIII respectively (as previously described). Additionally the restriction cut vectors were dephosphorylated at the 5' end with calf-intestine alkaline phosphatase (Promega Corp, Madison, Wis.)- 1 unit for 30 min. at 37° C., purified by agarose gel electrophoresis and concentrated by ethanol precipitation (as previously described). The pET-23a(+) insert and the pET-23a(+) cut vector were ligated with T4 DNA ligase (Promega Corp.). To 3 ng of insert were added 10 ng of cut vector in T4 DNA ligase buffer (Promega Corp.)+T4 DNA ligase (Promega Corp.)—3 units in a total volume of 10 µl and incubated for 16 hr. at 14° C. The pKK223-3 insert and the pKK223-3 cut vector were ligated as previously described. Competent *E. coli* cells (*Epicurian coli* XL2-Blue MRF', Stratagene, La Jolla, Calif.) were transformed with 2 µl ligation mix and plated on LB+carbenicillin (100 µg/ml) plates. Individual colonies were subcultured in LB+carbenicillin (100 µg/ml) medium and plasmid DNA isolated using the Qiagen Plasmid DNA mini kit. The insert was sequenced in entirety including both regions of the start and stop codon by the automated ABI Prism Dye Terminator Cycle Sequencing procedure (Perkin-Elmer, Norwalk, Conn.) by the UW Biotech Dept (Madison, Wis.) to confirm the correctness of the construct.

For protein expression, the pET-23a(+)—gene insert expression vector was transformed into competent BL21 (DE3) *E. coli* cells (Novagen, Madison, Wis.). This cell line is a λDE3 lysogen carrying the gene for T7 RNA polymerase under control of IPTG. For transformation, 20 µl of competent cells were treated with 0.1 µg of plasmid DNA. After transformation, 10 µl of cells were plated on LB+carbenicillin (100 µg/ml)+plates and grown overnight at 37° C. Individual colonies were subcultured in LB+carbenicillin (100 µg/ml) overnight at 37° C. and ±1 mM IPTG for 3 additional hours. For protein expression, the pKK223-3—gene insert expression vector was used with the *Epicurian coli* XL2-Blue MRF' (Stratagene, La Jolla, Calif.) without transfer to another cell line or placed in *E. coli* JM109 cells. In the latter case, 100 µl of competent JM109 cells (Stratagene, La Jolla, Calif.) were treated with 5 ng of plasmid DNA and the cells transformed, plated, and subcultured as previously described.

Evaluation of the codon usage for the Clostridial lysine 2,3-aminomutase gene indicated that the most frequently used codon for arginine (AGA) is one of the most infrequently used codons in *E. coli*. There are 29 AGA codons for 29 total arginines with two regions containing two or three repeat AGA near the start codon. From the studies of Kane, Current Opinion in Biotech. 6:494 (1995) and Brinkmann, et al., Gene 85:109 (1989), the expression of heterologous genes containing a high frequency of rare codons (particularly AGG and AGA) in *E. coli* is difficult or impossible due to low cellular concentrations of the respective tRNA. Brinkmann et al. suggest that the presence of rare AGA codon usage can be relieved by overexpression of the *E. coli* dnaY gene, which supplies this minor arginine tRNA. The sequence of the *E. coli* dnaY gene was published by Garcia et al., Cell 45:453 (1986). The primary products of this gene are RNAs of 180 and 190 nucleotides which are processed in vivo to form the mature arginine tRNA of 77 nucleotides.

Cotransfection of *E. coli* BL21 (DE3) cells with both vectors (pET23a(+) vector and pAlter-EX2 vector containing the dnaY gene) was not required for expression of the *Clostridial* lysine 2,3-aminomutase gene in *E. coli*. However, lysine 2,3-aminomutase activity of *E. coli* cellular extracts without pAlter-Ex2/dnaY were approximately 80% less than cellular extracts with this construct. The specific activity of the purified enzyme isolated from cells without pAlter-Ex2/dnaY was approximately half of that of the enzyme isolated from cells containing the dnaY gene. The yield of purified enzyme from equivalent amounts of cells was also decreased by 65% when dnaY was absent. Furthermore, cell growth in the absence of the vector containing the dnaY gene was significantly decreased. The doubling time of cultured *E. coli* cells containing the pET 23a(+) vector during expression of the lysine 2,3-aminomutase gene was approximately four times the doubling time of the same *E. coli* cells with the additional pAlter-Ex2 vector containing the dnaY gene. Therefore, for long-term stability and maximal expression, *E. coli* cells containing both expression vectors were prepared. The dnaY gene was isolated from *E. coli* chromosomal DNA by PCR. Primers were prepared which produced a 327 bp insert containing BamHI and EcoRI restriction sites necessary for cloning into pAlter-Ex2 plasmid vector (Promega Corp.). This vector has a p15a origin of replication which allows it to be maintained with colE1 vectors such as pET-23a(+) and pKK223-3. Also the presence of this vector confers tetracycline resistance to *E. coli*. The PCR primers used for pAlter-Ex2 were:

```
(+) strand-                              (SEQ ID NO:31)
5'-TATAGGATCCGACCGTATAATTCACGCGATTACACC-3', -) strand-                               (SEQ ID NO:32)
5'-TAGAGAATTCGATTCAGTCAGGCGTCCCATTATC-3'.
```

Chromosomal DNA from *E. coli* JM109 cells (Stratagene, La Jolla, Calif.) was prepared and purified utilizing the Qiagen Genomic Tip 500/G #13343 (Qiagen, Inc., Santa Clarita, Calif.). After ethanol precipitation, the genomic DNA was resuspended in TE (pH 8.0) buffer. The PCR reaction mixture (100 µl total volume) contained: *E. coli* chromosomal DNA—2.5 µg; cloned Pfu DNA polymerase reaction buffer (Stratagene, La Jolla, Calif.); dNTPs—0.2 mM each; oligonucleotide primers—1 µM each; cloned Pfu DNA polymerase (Stratagene, La Jolla, Calif.)—5 units. All samples were overlayered with 100 µl mineral oil and subjected to 35 cycles of 1 min. at 94° C., 30 sec. at 37° C., 15 sec. at 50° C., and 3 min. at 72° C. After thermocycling, DNA formed during the PCR process was further purified by agarose electrophoresis (2% agarose, Promega Corp., Madison, Wis.) in TAE buffer (0.04 M Tris-acetate pH 8.0+1 mM EDTA). Following identification and excision of the appropriately sized (~320 base pairs) ethidium bromide stained band, DNA was extracted from the agarose using the GenElute Minus EtBr spin column (Supelco, Bellefonte, Pa.) concentrated by precipitation with ethanol, and resuspended in TE pH 8.0 buffer.

The purified PCR product was blunt-end ligated to pCR-Script Amp cloning vector (Stratagene, La Jolla, Calif.) using 0.3 pmoles insert to 0.005 pmoles vector according to manufacturer's specifications. The ligated DNA was used to transform XL1-Blue MRF' *E. coli* cells (Stratagene, La Jolla, Calif.) which were subsequently plated on LB+carbenicillin+IPTG+X-Gal plates (as previously described) and cultured overnight. White colonies were chosen and subcloned in LB+carbenicillin (100 µg/ml) media for plasmid purification. Plasmid DNA was purified using Qiagen Plasmid mini kit (Qiagen, Inc., Santa Clarita, Calif.) and subjected to restriction digestion. For the pAlter-Ex2 insert, 1 µg of plasmid DNA was cut with BamHI (Promega Corp., Madison, Wis.)—10 units and EcoRI (Promega Corp.)—10 units in a total volume of 100 µl for 1 hr. at 37° C. The insert DNA was separated from the plasmid DNA by agarose gel electrophoresis (3% agarose in TAE buffer) and purified and concentrated as previously described. The expression vector, pAlter-Ex2—10 µg was similarly cut with BamHI and EcoRI (as previously described). Additionally the restriction cut vector was dephosphorylated at the 5' end with calf-intestine alkaline phosphatase (Promega Corp., Madison, Wis.)—10 units for 1 hr. at 37° C., purified by agarose gel electrophoresis and concentrated by ethanol precipitation (as previously described). The dnaY insert and the pAlter-Ex2 cut vector were ligated with T4 DNA ligase (Promega Corp.). To 1.68 ng of insert were added 10 ng of cut vector in T4 DNA ligase buffer (Promega Corp.)+T4 DNA ligase (Promega Corp.)—3 units in a total volume of 10 µl and incubated for 16 hr. at 14° C. Competent BL21(DE3) cells (Novagen, Madison, Wis.) were transformed with 1 µl of ligation mix and plated on LB+tetracycline (12.5 µg/ml). Individual colonies were subcultured in LB+tetracycline (10 µg/ml) medium and plasmid DNA isolated using the Qiagen Plasmid DNA mini kit. The insert was sequenced completely by the dideoxy NTP method previously described to confirm the correctness of the construct and found to agree with the expected sequence.

BL21(DE3) cells with the pAlter-Ex2 vector (dnaY gene) were cotransfected with pET-23a(+) (lysine 2,3-aminomutase gene). Competent BL21(DE3) cells containing the pAlter-Ex2 dnaY gene insert were prepared as follows: *E. coli* cells were grown overnight in LB+tetracycline (10 µg/ml). These cells were used to innoculate a fresh culture of LB+tetracycline to give a starting absorbance at 600 nm of 0.1. The cells were cultured at 37° C. with shaking until reaching an absorbance of 0.6. Forty ml of this culture were transferred to a centrifuge tube and centrifuged: at 2000×g for 10 min. at 4° C. To the cell pellet was added 10 ml of ice cold 0.1 M $MgCl_2$. The cell pellet was gently resuspended and incubated on ice for 20 min. followed by another centrifugation at 2000×g for 10 min. at 4° C. To the cell pellet was added 2.5 ml of ice cold 0.1 M $CaCl_2$. The cell pellet was gently resuspended and incubated on ice for an additional 40 min.

The above competent BL21(DE3) cells containing the p-Alter-EX2 vector (dnaY gene) were then cotransformed separately with pET23a(+) plasmid DNA (lysine 2,3-aminomutase gene). To 20 µl of competent cells on ice was added 0.1 µg of pET23a(+) plasmid DNA. The sample was incubated on ice for 30 min. followed by a 45 sec. heat shock at 42° C. and cooling on ice for 2 additional min. SOC medium (80 µl) was added and the cells incubated at 37° C. with shaking at 220 rpm for 1 hr. The cells were plated on LB+carbenicillin (100 µg/ml)+tetracycline (12.5 µg/ml) and cultured overnight. Individual colonies were subcultured in LB+carbenicillin (100 µg/ml)+tetracycline (10 µg/ml) overnight at 37° C.

EXAMPLE 3

Expression of *Clostridia subterminale* SB4 Lysine 2,3-aminomutase Gene in *E. coli*

Expression of the cloned gene *Clostridial* lysine 2,3-aminomutase gene in *E. coli* was ascertained by sodium dodecyl sulfate (SDS) polyacrylamide gel electrophoresis (PAGE). A 1 ml aliquot of final cell stocks [*E. coli* BL21(DE3) cells with pET-23a(+) (lysine 2,3-aminomutase gene)±p-Alter-EX2 vector (dnaY gene)] or [*E. coli* JM109 or *Epicurian coli* XL2-Blue MRF' with pKK223-3 (lysine 2,3-aminomutase gene)]±IPTG was centrifuged at 14,000×g for 10 min. at 4° C. to remove cell culture media. The cell pellet was resuspended in 0.5 ml of 10 mM of 4-(2-hydroxyethyl)-1-piperazine ethanesulfonic acid (Hepes) pH 7.5 buffer containing 0.6 mM $CaCl_2$ and 50 units deoxyribonuclease I (#D-4527, Sigma Chemical, St. Louis, Mo.). Following cell breakage by sonication using the micro-tip of the Sonic Dismembrator (setting 3 for three 15 sec intervals) (Model #550, Fisher Scientific, Pittsburgh. Pa.), 30 μl of sonicated cells were added to 100 μl of SDS PAGE sample buffer (0.06 M Tris-HCl pH 6.8 buffer containing 10% (v/v) glycerol, 0.7 M β-mercaptoethanol, 0.025 M bromophenol blue). The cell extract was heated at 95° C. for 5 min. prior to loading (5-20 μl/lane) on a mini polyacrylamide gel (Ready Gel #161-1106, Bio-Rad Laboratories, Hercules, Calif.), run at 150 volts (Ready Gel Cell #165-3125, Bio-Rad Laboratories, Hercules, Calif.) at constant voltage until the tracking dye was at the bottom of the gel, and stained with Coomassie Blue R-250 stain. Control cell extracts were prepared containing *E. coli* BL21 (DE3) cells with pET-23a(+) without the gene for lysine 2,3-aminomutase. Analysis of the stained SDS PAGE gel revealed one intensely stained band corresponding to a molecular weight of 47 kDa migrating between 40 and 50 kDa standard proteins (Benchmark Protein Ladder #10747-012, Life Technologies, Gaithersburg, Md.) in all samples containing pET 23a(+) or pKK223-3 expression vectors+*Clostridial* lysine 2,3-aminomutase gene. This band migrated with the same $R_f$ as purified *Clostridial* lysine 2,3-aminomutase. Only a weakly stained band was present in control cell extracts with the above expression vectors without the lysine 2,3-aminomutase gene.

A requirement for an anaerobic environment when measuring lysine 2,3-aminomutase activity (ie., formation of L-β-lysine from L-α-lysine) was previously demonstrated for the Clostridial enzyme [Moss and Frey, J. Biol. Chem. 265:18112 (1990); Petrovich et al., J. Biol. Chem. 226:7656 (1991)]. Therefore all subsequent steps including cell culture, cell extract preparation, and enzyme assay were done in the absence of oxygen. The following procedure demonstrates the formation of L-β-lysine from L-α-lysine in vivo in *E. coli* cells. BL21(DE3) cells containing the pET23a(+) expression vector for the *Clostridial* lysine 2,3-aminomutase gene with the expression vector for *E. coli* dnaY gene were cultured anaerobically at 37° C. in 100 ml of M9 medium (0.68 gm $Na_2HPO_4$, 0.3 gm $KH_2PO_4$, 0.05 gm NaCl, 0.1 gm $NH_4Cl$) containing $CaCl_2$ (0.1 mM), $MgSO_4$ (1 mM), $ZnSO_4$ (10 μM), Fe(II)$SO_4$ (50 μM), D-(+)-glucose (0.2% w/v), ampicillin (100 μg/ml)±tetracycline (10 μg/ml) in 150 ml sealed bottles made anaerobic by sparging with nitrogen gas and the addition of 1 mM sodium dithionite and 4 mM sodium thioglycolate (Sigma Chemical Co., St. Louis, Mo.). After cells reached a density of approximately 0.5 OD units at 600 nm, L-α-lysine (50 mM) was added and the cells cultured an additional 16 hrs. at 37° C. anaerobically. Cells were harvested by centrifugation at 6,000×g for 10 min. and resuspended in 0.5 ml of distilled water. Following sonication using the micro-tip of the Sonic Dismembrator (setting 3 for three 15 sec. intervals) (Model #550—Fisher Scientific, Pittsburgh. Pa.), the lysed cells were centrifuged at 14,000×g for 20 min. at room temperature. The supernatant was used to measure formation of L-β-lysine from L-α-lysine resulting from the expression of the *Clostridial* lysine 2,3-aminomutase gene in *E. coli*. Control cells which contained pET 23a(+) plasmid without the *Clostridial* lysine 2,3-aminomutase gene were also cultured and harvested as previously described.

The presence of L-β-lysine in *E. coli* cell extract was detected by treating the extract with phenylisothiocyanate (Pierce Chemical Co., Rockford, Ill.) which derivatizes amino acids to their respective phenylthiocarbamyl derivatives. These compounds are readily separated and detected by high pressure liquid chromatography (HPLC). The procedure is based on the method of Heinrikson and Meredith, Anal. Biochem. 136:65 (1984): 10 μl of cell extract (see above) were treated with 100 μl of coupling buffer (acetonitrile: pyridine:triethylamine:water 10:5:2:3 v/v/v) and evaporated to dryness using a Speed-Vac (Savant Instruments, Inc., Hicksville, N.Y.). The sample was redissolved in 100 μl coupling buffer and 5 ml of phenylisothiocyanate was added and mixed. After 5 min. at room temperature, the sample was again dried using the Speed-Vac. The dried sample was redissolved in distilled water (200 μl) and centrifuged at 14,000×g for 10 min. to remove undissolved material. The sample was injected into a Waters HPLC (Millipore Corporation, Waters Chromatography Division, Milford, Mass.) equipped with a Vydac $C_8$ reverse phase column (Vydac 208TP54, 5 microns, 4.6×250 mm, The Separations Group, Hesperia, Calif.). The derivatized L-α-lysine and L-β-lysine were separated using a linear gradient composed of buffer A (0.05 M ammonium acetate in water) and buffer B (0.1 M ammonium acetate in acetonitrile:methanol:water (46:10:44 v/v/v) at a flow rate of 1 ml/min. at room temperature and monitored at a wavelength of 254 nm. The initial conditions were 30% buffer B for 2 min. followed by a linear gradient to 60% buffer B in 24 min. The retention times for phenylthiocarbamyl derivatives of L-α-lysine was 25.7±0.3 min. and for L-β-lysine was 22.9±0.4 min. L-β-lysine (up to 35% of total lysine) was observed in all cell extracts of *E. coli* cells containing the pET 23a(+) plasmid vector with the *Clostridial* lysine 2,3-aminomutase gene and absent in control cells which were treated identically but did not contain the plasmid with the *Clostridial* lysine 2,3-aminomutase gene.

In vitro formation of β-lysine by *E. coli* cell extracts was also measured utilizing the standard assay procedure (Ballinger et al., Biochemistry 31:10782 (1992). The conversion of radiolabeled C-14 L-α-lysine to radiolabeled C-14 L-β-lysine was observed in the following manner:

Aerobically grown *E. coli* cells (1 ml) containing the pET 23a(+) plasmid vector with the *Clostridial* lysine 2,3-aminomutase gene and the p-Alter-EX2 plasmid vector with the *E. coli* dnaY gene were used to seed a glass fermentor (Virtis Laboratory Fermentor #233395, Virtis Corporation, Gardiner, N.Y.) containing 15 liters of 2×YT media (240 gm Difco Bactotryptone, 150 gm Bacto yeast extract, 2.5 gm sodium chloride, Difco Laboratories, Detroit, Mich.) and supplemented with 50 μM Fe(II)$SO_4$, 50 μM $ZnSO_4$, 50 μM Na$_2$S, 4 mM sodium thioglycolate, 100 μg/ml ampicillin, and 10 μg/ml tetracycline. The sealed flask was made anaerobic by gentle bubbling of nitrogen gas for 3 hours prior to cell inoculation. Anaerobicity was monitored by the presence of a small quantity of methylene blue (10 mg) which remains colorless in the absence of oxygen. After approximately 14 hours anaerobic culture at 37° C. when the cell density had reached 0.05 OD (optical density) at 600 nm, 0.2% (w/v) D-(+) glucose was added. The culture was allowed to continue to 0.7 OD at 600 nm when 1 mM isopropyl-β-thiogalactopyranoside (IPTG) (Fisher Scientific, Pittsburgh, Pa.) was added to induce further expression of the *Clostridial* lysine 2,3-aminomutase gene. After 4 hours, the culture was cooled to 24° C. and allowed to continue for an additional 12 hours before cell harvesting. Cells were harvested by concentration using tangential flow filtration (Pellicon System, Millipore Corporation, Bedford, Mass.) followed by centrifugation at 5,000×g for 20 min. The cell pellets were snap frozen and stored in liquid nitrogen until used.

All subsequent operations were conducted in an anaerobic glove box (Coy Laboratory Products, Inc. Ann Arbor, Mich.). Cells (approximately 1-2 gms) were placed in 3 ml of 0.03 M sodium EPPS buffer (N-[2-hydroxyethylpiperazine-N'-[3-propanesulfonic acid]) pH 8 containing 0.1 mM L-α-lysine, 10 μM pyridoxal-5-phosphate, and 1 mM dithiothreitol (Sigma Chemical Co., St. Louis, Mo.). The cells were broken by sonication (Sonic Dismembrator #550, Fisher Scientific, Pittsburgh, Pa.) using the microtip at a setting of 3 for five 20 sec. bursts with cooling on ice. The broken cells were centrifuged at 80,000×gav for 30 min.

The supernatant was used to measure L-β-lysine formation according to the procedure of Ballinger et al. Biochemistry 31:10782 (1992). The procedure is based on the observation that radiolabeled L-α-lysine can be separated from radiolabeled L-β-lysine by paper electrophoresis in formic acid solution based on the difference in the pKa of the carboxyl group of each amino acid. The cell extract was incubated in 0.04 M EPPS pH 8 buffer containing 1 mM ferrous ammonium citrate, 0.5 mM pyridoxal 5-phosphate, and 20 mM dihydrolipoic acid for 4 hr. at 37° C. After the reductive incubation, the sample was diluted into 0.18 M EPPS pH 8 buffer containing 3 mM sodium dithionite, 18 μM S-adenosylmethionine, 44 mM C-14 labeled (#NEC280E-NEN Life Science Products, Boston, Mass.) and unlabeled L-α-lysine and incubated 4 min. at 37° C. The reaction was stopped by the addition of 0.2 M formic acid. The mixture was spotted onto chromatography paper (Whatman #3001917, Whatman, LTD, Maidstone, England), the amino acids separated by electrophoresis and radioactivity measured according to the published procedure. The cell extract exhibited lysine 2,3-aminomutase activity (4-5 units/mg protein). The specific activity of purified lysine 2,3-aminomutase from *Clostridium subterminale* SB4 cells has been reported as 30-40 units/mg (Lieder et.al., Biochemistry 37:2578 (1998)). Thus lysine 2,3-aminomutase represents approximately 10-15% of total cellular protein in this expression system.

The recombinant produced lysine 2,3-aminomutase was purified according to the procedure of Moss and Frey, J. Biol. Chem. 265:18112 (1990) as modified by Petrovich et al., J. Biol. Chem. 226:7656 (1991), as previously discussed. The purified recombinant produced lysine 2,3-aminomutase had equivalent enzyme activity (34.5±1.6 μmoles lysine min$^1$ mg$^{-1}$ protein) to purified naturally produced *Clostridial* enzyme (Lieder et al., Biochemistry 37:2578 (1998)).

EXAMPLE 4

Reactions of Lysine 2,3-aminomutase with α-Amino Acids Other Than L-Lysine

Although lysine 2,3-aminomutase is selective for L-lysine as its substrate, it also catalyzes the 2,3-aminomutation of other L-α-amino acids. A simple and definitive assay for such reaction is the EPR spectrum of a mixture of lysine 2,3-aminomutase with its coenzymes and an L-α-amino acid.

Figure 1B:
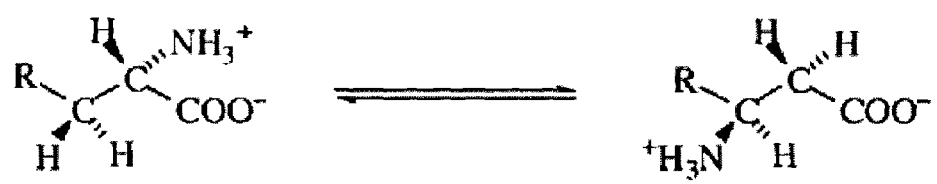
FIG. 1B is an equation showing the interconversion of L-lysine and L-β-lysine.
Figure 2:
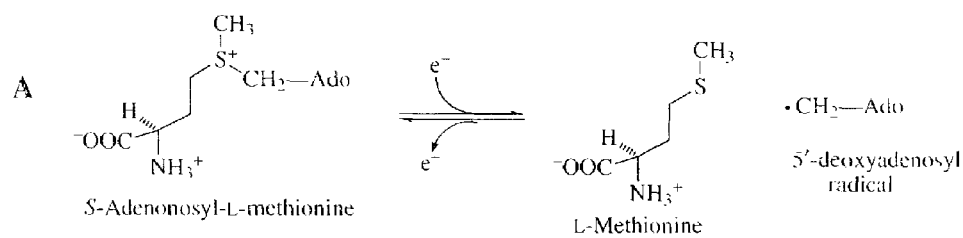
FIG. 2 is the mechanism of action of lysine 2,3-aminomutase with L-lysine as the substrate. All of the chemical processes shown here take place within the active site of lysine 2,3-aminomutase. A) Reversible cleavage of S-adenosyl-L-methionine requires the reversible insertion of an electron. B) The electron required in A originates with an iron-sulfur center [4Fe-4S] in the enzyme. C) Mechanism by which the 5'-deoxyadenosyl radical from A initiates and facilitates the 2,3-aminomutation of substrates, in this case, L-lysine.
Figure 2:
Figure 2:
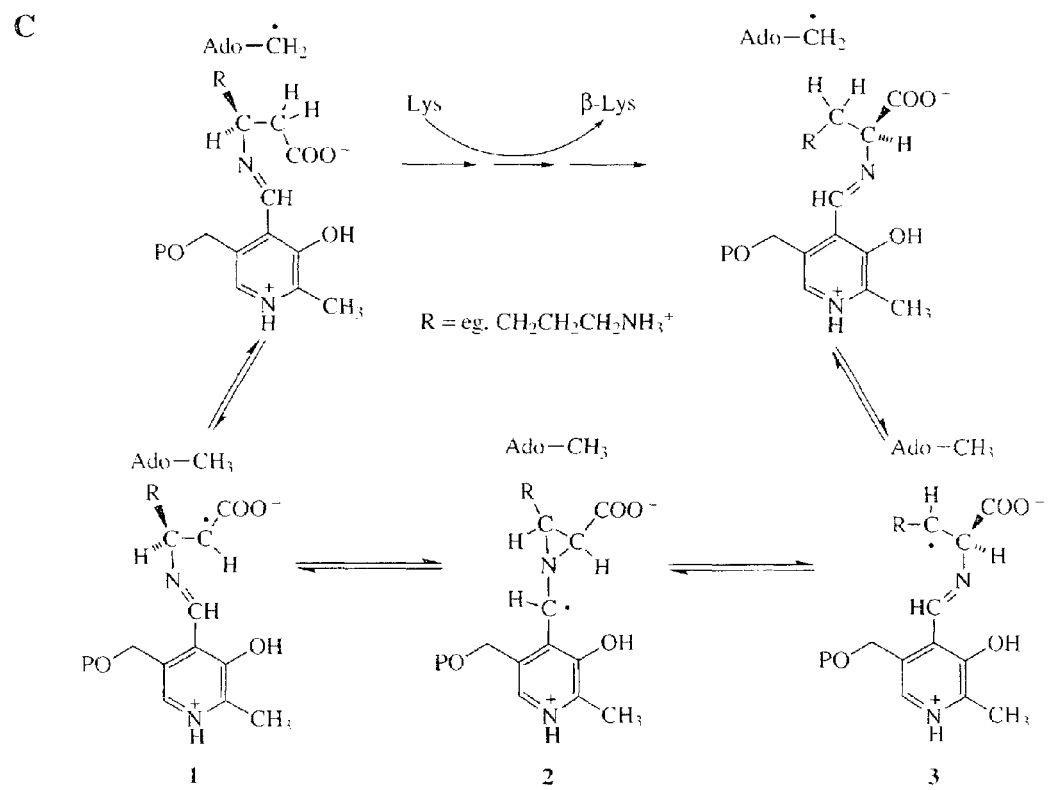

The EPR spectrum of the mixture of L-lysine with lysine 2,3-aminomutase and its coenzymes uniquely defines the structure of the product-related free radical bound to the enzyme as its external aldimine with PLP. The spectral envelope is determined by five structural features in the substrate: 1) the L-configuration at the optically active carbon-2, shown as $C_\alpha$ in FIG. 1A; 2) a hydrogen atom bonded to $C_\alpha$; 3) a carboxyl group bonded to $C_\alpha$; 4) a nitrogen atom bonded to $C_\beta$; and 5) a hydrogen atom bonded to $C_\beta$. Little or no magnetic interactions can be detected between the unpaired electron and atoms in the R-substituent in equation shown in FIG. 1B and FIG. 2C. The conformation of the radical is determined by the dihedral angles relating the axis of the π-radical orbital to the bonds $C_\alpha$—H, $C_\beta$—H, and $C_\beta$—N, and these angles determine the nuclear hyperfine splitting in the spectrum and, thereby, the shape of the spectral envelope. The resulting EPR spectrum is diagnostic of a product-related free radical at the active site of lysine 2,3-aminomutase.

Figure 3:
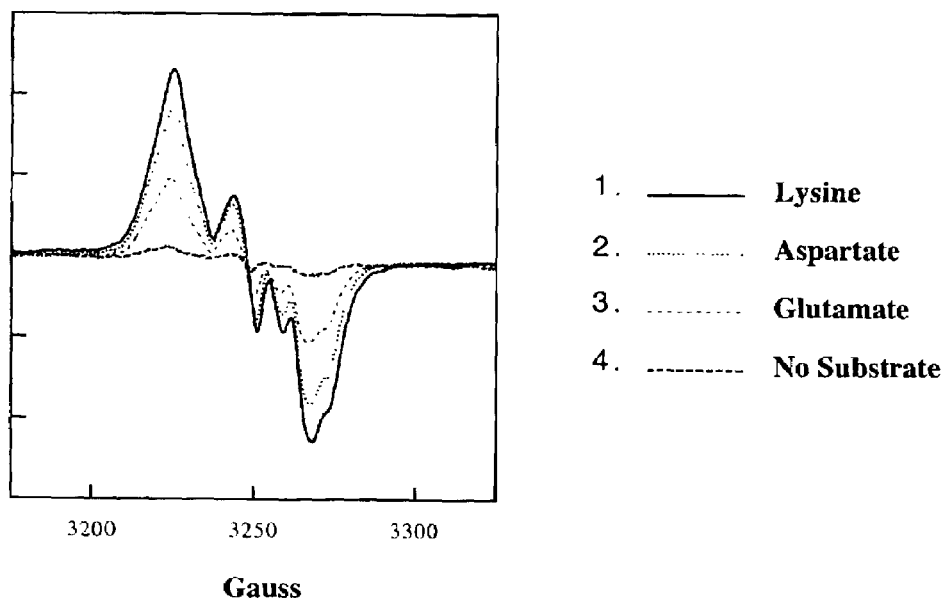
FIG. 3 is electron paramagnetic resonance (EPR) spectroscopy of *Clostridium subterminale* SB4 lysine-2,3-aminomutase in the presence of L-lysine (1), L-aspartate (2), L-glutamate (3), or no substrate (4). Reductively incubated recombinant-produced purified lysine-2,3-aminomutase (18) (75 μM-hexamer) was quickly mixed at 24° C. and frozen (total time<15 sec) at −150° C. with the following components: A) Tris(hydroxymethyl)aminomethane sulfate (Tris-sulfate) 240 mM pH 8.0; B) S-(5'-adenosyl)-L-methionine 1.4 mM; C) sodium hydrosulfite 2.0 mM; D) L-lysine, L-aspartate, or L-glutamate 120 mM. Concentrations listed are final concentrations after mixing. Following freezing, samples were evaluated at 77° K by EPR using a Varian model E3 spectrometer with the following settings: Field center—3250 Gauss; Scan width—200 Gauss; Microwave frequency—9.1 GHz; Microwave power—5 milli Watts; Modulation frequency—100 kHz; Modulation amplitude—1.6 Gauss; Time constant—0.3 sec.; Scan time—240 sec; Gain—125,000.

FIG. 3 shows the EPR spectra of a series of samples containing lysine 2,3-aminomutase and its coenzymes mixed with L-lysine, L-aspartate, or L-glutamate and then frozen at 77 K for EPR analysis. Spectrum 1 is that of free radical 3 in FIG. 2C, which is of the product related radical form of L-β-lysine bound to the active site of lysine aminomutase in the form of its external aldimine with PLP. Spectra 2 and 3 are those elicited with L-aspartate and L-glutamate, respectively, in place of L-lysine. The spectra observed with L-aspartate and L-glutamate are less intense but otherwise essentially indistinguishable from that with L-lysine. Therefore, we conclude that the EPR spectra 2 and 3 in FIG. 2 correspond to free radicals at the active site that are structurally similar to that of 3 in FIG. 2C, with the substitution of R=CH$_2$COOH in spectrum 2 and CH$_2$CH$_2$COOH in spectrum 3 in place of CH$_2$CH$_2$CH$_2$NH$_3^+$. The structures are of product-related radicals derived from L-aspartate and L-glutamate. (Note that the chemical linkages in β-aspartate and α-aspartate are the same but may differ in stereochemistry at the optical centers.)

Figure 4:
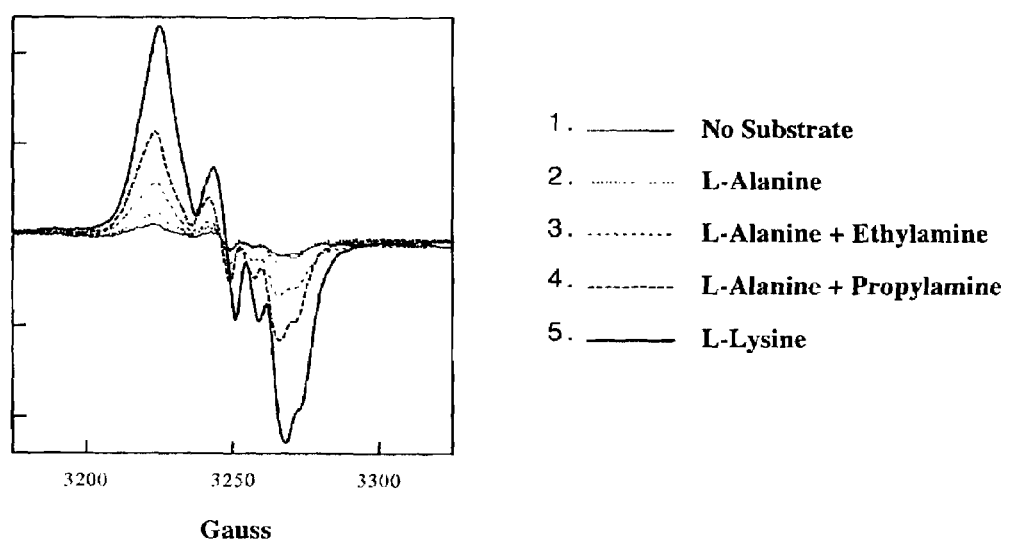
FIG. 4 is electron paramagnetic resonance (EPR) spectroscopy of *Clostridium subterminale* SB4 lysine-2,3-aminomutase in the presence of L-alanine (2), L-alanine+ethylamine (3) L-alanine+propylamine (4), L-lysine (5) and no substrate (1). Conditions as given in FIG. 3 except L-lysine or L-alanine 120 mM; ± ethylamine or propylamine each 0.19 M or no substrate (5).

FIG. 4 shows the EPR spectra of a series of solutions containing lysine 2,3-aminomutase and its coenzymes mixed with L-alanine in spectrum 2, L-alanine plus ethylamine in spectrum 3, L-alanine plus propylamine in spectrum 4, and L-lysine in spectrum 5. Spectrum 5 is that of free radical 3 in FIG. 2C, the product related radical form of L-β-lysine bound to the active site of lysine aminomutase in the form of its external aldimine with PLP. Spectra 2, 3 and 4 are elicited with L-alanine in place of L-lysine and are less intense but otherwise essentially indistinguishable from that with L-lysine. We conclude that the EPR spectra 2, 3 and 4 in FIG. 4 correspond to free radicals at the active site that are structurally similar to that of 3 in FIG. 2C, with the substitution of R=H. (Note that β-alanine has no optical center.)

Figure 5:
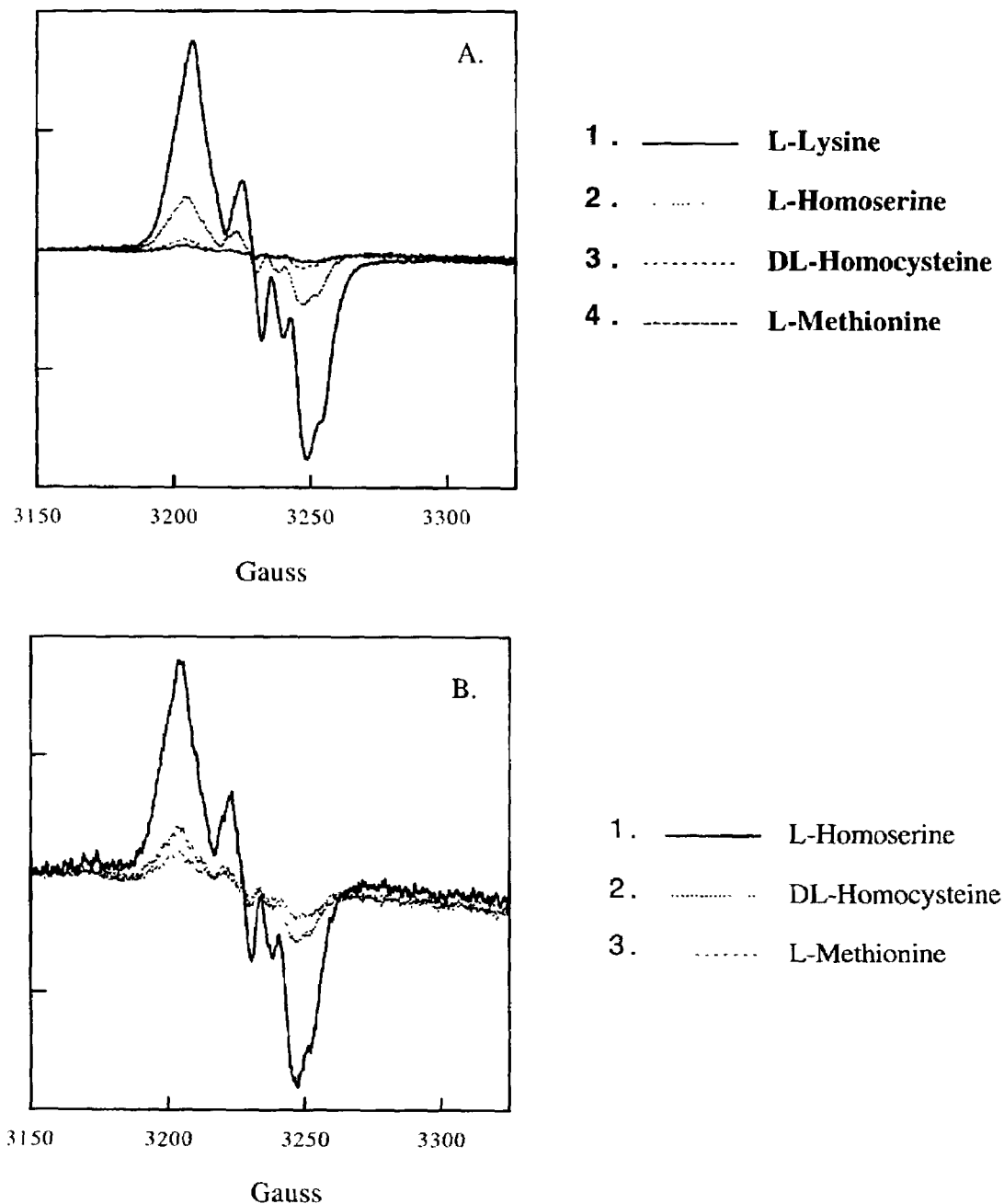
FIG. 5 is electron paramagnetic resonance spectroscopy of *Clostridium subterminale* SB4 lysine-2,3-aminomutase in the presence of L-lysine (1), L-homoserine (2), DL-homocysteine (3), or L-methionine (4). Reductively incubated recombinant-produced purified lysine-2.3-aminomutase (18) (51.4 μM-hexamer) was quickly mixed at 24° C. and frozen (total time<15 sec) at −150° C. with the following components: A) Tris(hydroxymethyl)aminomethane sulfate (Tris-sulfate) 185 mM pH 8.0; B) S-(5'-adenosyl)-L-methionine 1.1 mM; C) sodium hydrosulfite 1.5 mM; D) L-lysine 92 mM, L-homoserine 92 mM, or DL-homocysteine 92 mM, or L-methionine 65 mM. Concentrations listed are final concentrations after mixing. Following freezing, samples were evaluated at 77° K by EPR using a Varian model E3 spectrometer with the following settings: Field center—3250 Gauss; Scan width—200 Gauss; Microwave frequency—9.1 GHz; Microwave power—5 milli Watts; Modulation frequency—100 kHz; Modulation amplitude—1.6 Gauss; Time constant—0.3 sec.; Scan time—240 sec; Gain—250,000.

FIG. 5A shows the EPR spectra of a series of solutions containing lysine 2,3-aminomutase and its coenzymes mixed with L-lysine (spectrum 1), L-homoserine (spectrum 2), DL-homocysteine (spectrum 3), or L-methionine (spectrum 4). Spectrum 1 is that of free radical 3 in FIG. 2C, the product related radical form of L-β-lysine bound to the active site of lysine aminomutase in the form of its external aldimine with PLP. Spectra 2 and 3 are those elicited with L-homoserine and DL-homocysteine, respectively, in place of L-lysine. Spectrum 4 is elicited with L-methionine. The spectra observed with L-homoserine and DL-homocysteine are less intense but otherwise essentially indistinguishable from that with L-lysine. The spectra with L-homoserine, DL-homocysteine, and L-methionine are expanded in FIG. 5B to show the line-shape of the weak spectrum for L-methionine. We conclude that the EPR spectra 2 and 3 in FIG. 5A correspond to free radicals at the active site that are structurally similar to that of 3 in FIG. 2C, with the substitution of R=$CH_2OH$ in spectrum 2 and $CH_2SH$ in spectrum 3. The EPR spectrum with L-methionine is weak but also consistent with expectations for the analogous radical, with the substitution of R=$CH_2$—S—$CH_3$.

The EPR results show that lysine 2,3-aminomutase carries out the same aminomutase rearrangements of L-glutamate, L-aspartate, L-alanine, L-homoserine, L-methionine and L-homocysteine to form product-related β-amino acid radicals as it does with L-lysine as the substrate. The radicals are formed within a few seconds.

EXAMPLE 5

Reaction of Lysine 2,3-aminomutase with L-alanine to produce β-alanine

Reductively incubated recombinant-produced purified *Clostridium subterminale* SB4 lysine-2,3-aminomutase (10 μM-hexamer) was mixed with the following components: 1) EPPS buffer 36 mM pH 8.0, Na salt; 2) S-(5'-adenosyl)-L-methionine 390 μM; 3) sodium hydrosulfite 3.6 mM; 4) L-alanine 380 mM; 5) ethylamine 0.20 M pH 8.0. At appropriate time intervals at 37° C., 60 μl of reaction mix was added to 20 μl of 2N perchloric acid to stop the reaction. Until acid quenched, all operations were conducted in an anaerobic glove box. Samples were centrifuged at 14,000×g for 10 min. The supernatants were reacted with phenyisothiocyanate (PITC) [Anal. Biochem. 136, 65-74 (1984)]. 5 μl of supernatant was added 10 μl of PITC in 100 μl of coupling buffer and the sample incubated at room temperature for 5 min prior to removal of solvent by vacuum centrifugation and resuspension of sample in 300 μl distilled water. The PITC derivative of L-alanine was separated fom the β-alanine derivative by HPLC chromatography using a C18 reverse phase column (Beckman Ultrasphere 5μ, 4.6 mm×25 cm, #235329), flow rate 1 ml/min, room temperature, sample injection volume 5-25 μl. The eluting compounds were detected by spectrophotometry at a wavelength of 254 nm The amino acids were resolved with a complex linear gradient composed of buffer A: 0.05 M ammonium acetate in water and buffer B: 0.1M ammonium acetate in 44% water, 46% acetonitrile, 10% methanol. The gradient established was 0-10% Buffer B in 35 min, then 10-30% Buffer B in 35 min. The PITC derivative of L-alanine eluted at a retention time of 35.0 min whereas the PITC derivative of β-alanine eluted at 26.6 min.

Figure 6:
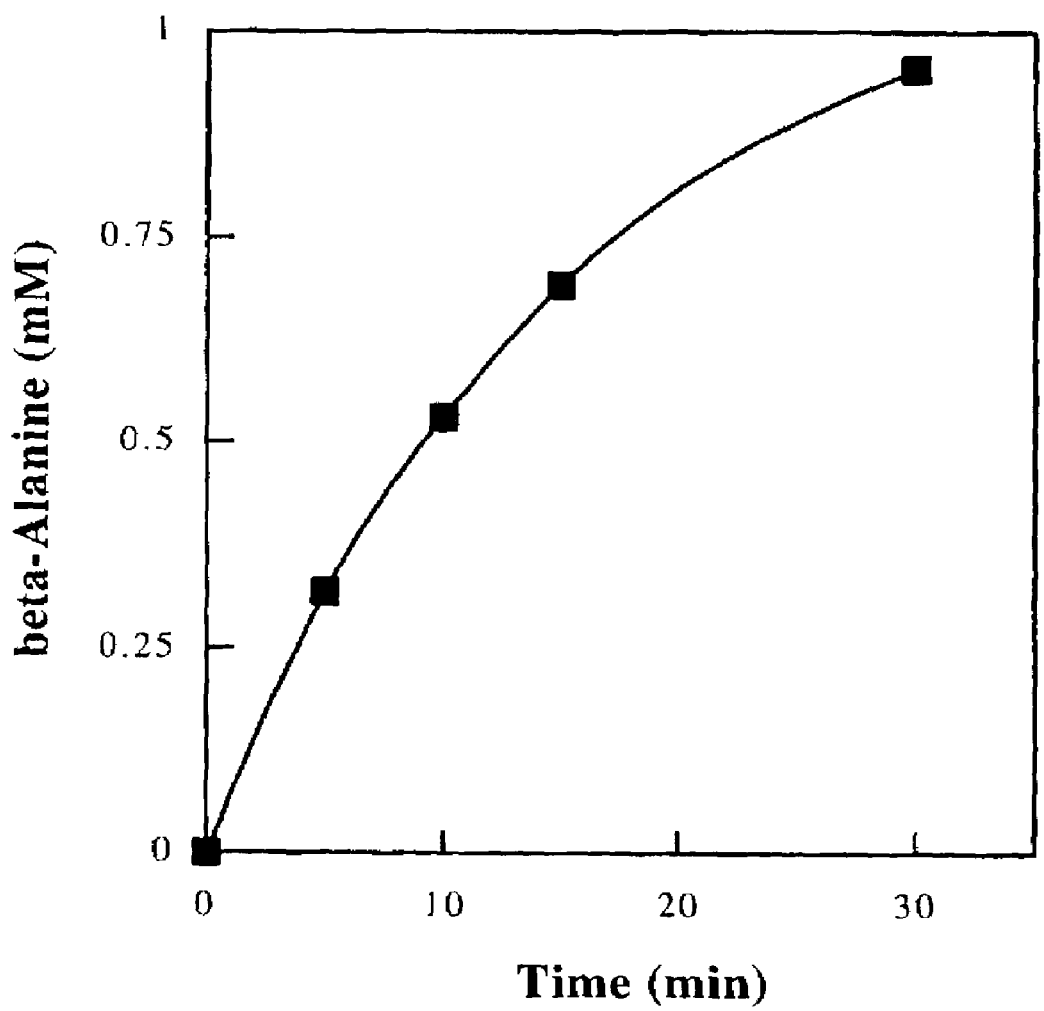
FIG. 6 is time course of the appearance of the HPLC peak of β-alanine by *Clostridium subterminale* SB4 lysine 2,3-aminomutase. Reductively incubated recombinant-produced purified lysine-2,3-aminomutase (18) (10 μM-hexamer) was mixed with the following components: A) N-[2-hydroxyethyl-piperazine-N'-[3-propanesulfonic acid] (EPPS) 36 mM pH 8.0, Na salt; B) S-(5'-adenosyl)-L-methionine 390 μM; C) sodium hydrosulfite 3.6 mM; D) L-alanine 380 mM; E) ethylamine 0.20 M pH 8.0. At various time intervals at 37° C., 60 μl of reaction mix was added to 20 μl of 2 N perchloric acid to stop the reaction. Samples were centrifuged at 14,000×g for 10 mm. The supernatants were treated with phenylisothiocyanate (PITC) according to the method of Heinrikson and Meredith (28). The PITC derivative of L-alanine was separated from the β-alanine derivative by HPLC chromatography (28) using a C18 reverse phase column (Beckman Ultrasphere 5μ, 4.6 mm×25 cm, #235329), flow rate 1 ml/min, room temperature. The amino acids were resolved with a complex linear gradient composed of buffer A: 0.05 M ammonium acetate in water and buffer B: 0.1M ammonium acetate in 44% water, 46% acetonitrile, 10% methanol. The gradient established was 0-10% Buffer B in 35 min, then 10-30% Buffer B in 35 min. The PITC derivative of L-alanine elutes at a retention time of 35.0 min whereas the PITC derivative of β-alanine elutes at 26.6 min.
Figure 7:
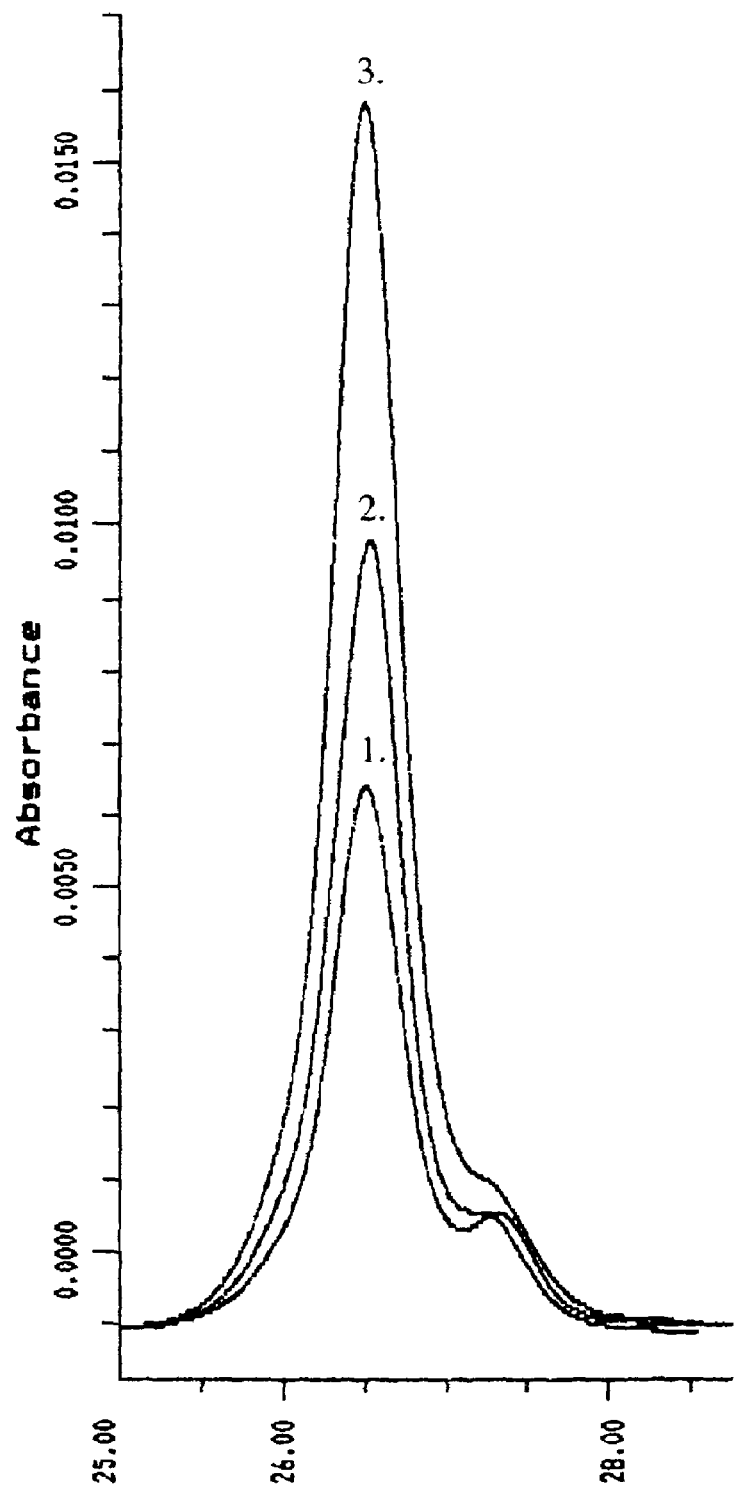
FIG. 7 is a co-elution of enzymatic product of *Clostridium subterminale* SB4 lysine 2,3-aminomutase reaction with L-alanine and authentic β-alanine standard. Reaction conditions as given in FIG. 6. A PITC derivative of a standard solution of β-alanine (Sigma, St. Louis, Mo., Product #A-7752) was added to the PITC sample from the 90 minute time point (FIG. 6) and co-chromatographed using conditions described in FIG. 6. Enzymatic product (1), product+0.9 nmoles β-alanine (2), product+2.7 nmoles β-alanine.

In a reaction of L-alanine as a substrate for Clostridial lysine 2,3-aminomutase, β-alanine was produced from L-alanine. The β-alanine was detected as its PITC derivative and assayed as a function of time during the reaction over a period of two hours. The progressive appearance of PITC-β-alanine is illustrated in FIG. 6. The enzymatic product co-eluted with authentic PITC-β-alanine, as proven by repeated supplementation (spiking) with authentic material (FIG. 7).

Figure 8:
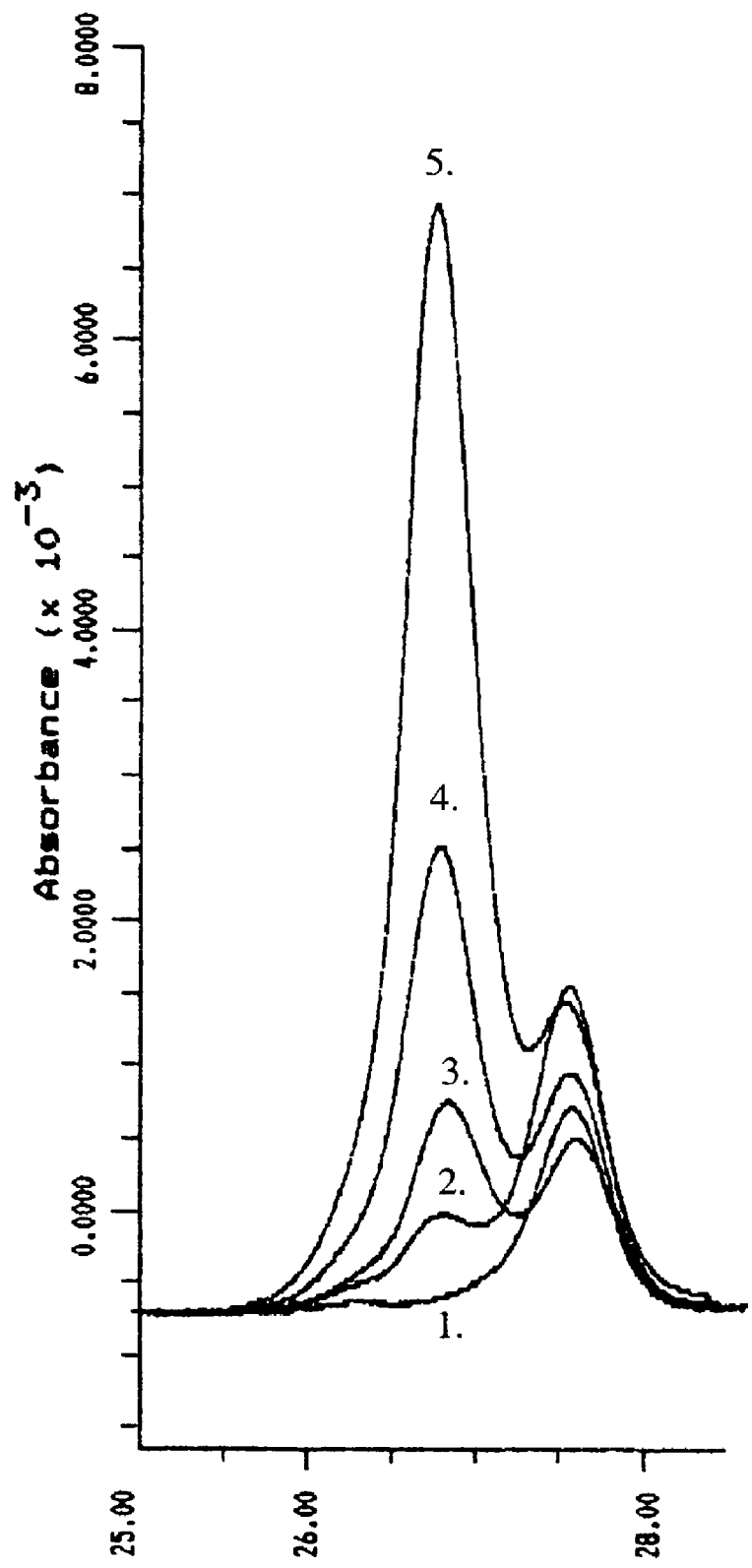
FIG. 8 is the effect of varying concentrations of L-alanine on the production of β-alanine by *Clostridium subterminale* SB4 lysine 2,3-aminomutase. Experimental conditions as given in FIG. 6 except for the concentration of L-alanine. The concentrations of L-alanine used: 0.05 M (2), 0.11 M (3), 0.20 M (4), and 0.38 M (5). The zero reaction time HPLC elution profile for 0.05 M L-alanine (1) is included. The enzyme was reacted with L-alanine for 90 min at 37° C. prior to stopping with perchloric acid and PITC derivatization.
Figure 9:
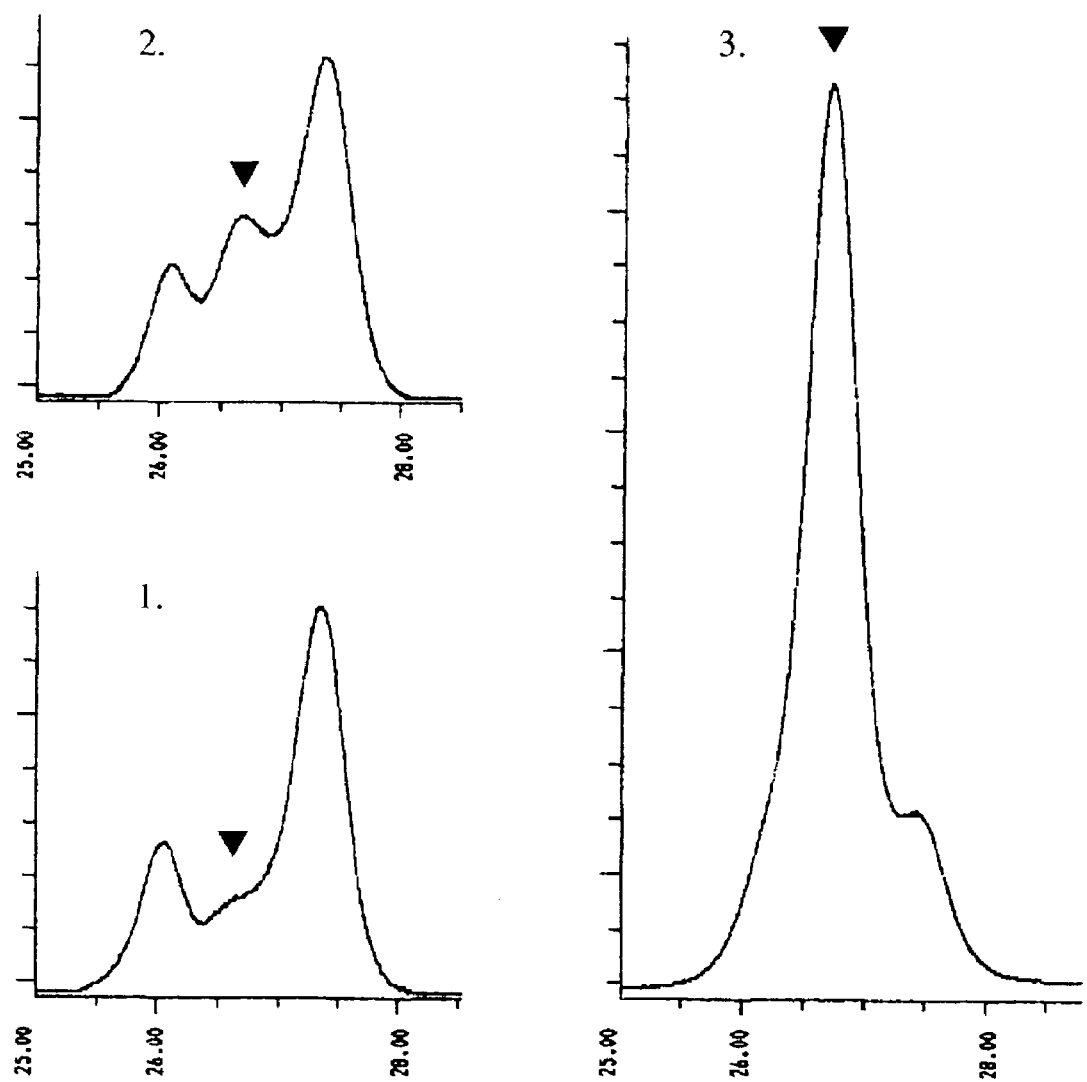
FIG. 9 is the potentiating effect of ethyl and propylamines on the generation of β-alanine from L-alanine by *Clostridium subterminale* SB4 lysine 2,3-aminomutase. Experimental conditions as given in FIG. 6 except for the following: L-alanine 0.38 M (1), L-alanine 0.38 M+propylamine 0.20M (2), and L-alanine 0.38 M+ethylamine 0.2 M (3). The enzyme was reacted with L-alanine for 90 min at 37° C. prior to stopping with perchloric acid and PITC derivatization. Arrow indicates position of β-alanine. Neighboring peaks are derived from solvent components of unknown nature. The ordinate scale is 2.3× for 1 and 2.

In another experiment conducted at varying concentrations of L-alanine (0.05 M to 0.38 M), the reactions were allowed to proceed for 90 min at 37 ° C. The β-alanine formed at each concentration of L-alanine was then measured as a function of the concentration of L-alanine. The results are shown in FIG. 8. The results show that lysine 2,3-aminomutase acts on L-alanine by producing increased β-alanine with increased substrate (L-alanine) concentration. Furthermore, the reaction was potentiated by the presence of ethylamine at 0.2 M (FIG. 9). Ethylamine fills the active site binding pocket normally occupied by the aminopropyl group of the side chain of L-lysine. Propylamine (0.2M) (FIG. 9) also potentiates the reaction less effectively than ethylamine. In the absence of ethylamine or propylamine, lysine 2,3-aminomutase still catalyzes the conversion of L-alanine to β-alanine at a low rate estimated to be about ¹⁄₂₀th the rate with 0.2 M ethylamine (FIG. 9).

EXAMPLE 6

Activity of Lysine 2,3-aminomutase Gene in *E. coli*

Lysine 2,3-aminomutase activity was measured with the *Escherichia coli* 2,3-aminomutase (P39280 protein) as described for alanine 2,3-aminomutase (see Example 5) with the following exceptions: P39280 protein, (25.4 μM-subunit); S-(5'-adenosyl)-L-methionine 90 μM; sodium hydrosulfite 2.3 mM; L-lysine 44 mM. The reaction was conducted at 37° C. for 60 min. The HPLC gradient established was 0-10% Buffer B in 35 min, 10-30% Buffer B in 35 min, 30-55% Buffer B in 35 min, and 55-100% Buffer B in 20 min. The PITC derivative of L-lysine eluted at a retention time of 101 min whereas the PITC derivative of β-lysine eluted at 95.6 min.

The P39280-protein from *E. coli* is a distant homologue of lysine 2,3-aminomutase from *Cl. subterminale*. The aligned amino acid sequences show approximately 30% identities. As discussed above, P39280-protein from *E. coli* does display 2,3-aminomutase activity toward L-lysine as a substrate.

The P39280-protein from *E. coli* is a lysine 2,3-aminomutase, and it is one of the least similar in amino acid sequence to lysine 2,3-aminomutase from *Cl. subterminale* among the known homologues. Therefore, it may be concluded that all of the homologues of lysine 2,3-aminomutase from *Cl. subterminale* are also lysine 2,3-aminomutases.

All references cited above are hereby incorporated by reference.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

What is claimed is:

1. A method of producing a β-amino acid comprising:
   (a) culturing a host cell comprising an expression vector that encodes a lysine 2,3-aminomutase in the presence of L-alanine, wherein the cultured host cell expresses lysine 2,3-aminomutase, and catalyzing the conversion of the L-alanine to a corresponding β-amino acid by utilizing the lysine 2,3-aminomutase as the catalyst, wherein the lysine 2,3-aminomutase has the amino acid sequence selected from the group consisting of SEQ ID NO: 2 and a variant thereof consisting of one amino acid substitution; and
   (b) isolating the β-amino acid from the cultured host cells.

2. A method of producing a β-amino acid comprising:(a) incubating L-alanine in a solution containing purified lysine 2,3-aminomutase, said solution containing all cofactors required for lysine 2,3 -aminomutase activity; and catalyzing the conversion of the L-alanine to a corresponding β-amino acid by utilizing the lysine 2,3-aminomutase as the catalyst, wherein the lysine 2,3-aminomutase has the amino acid sequence selected from the group consisting of SEQ ID NO: 2 and a variant thereof consisting of one amino acid substitution; and
   b) isolating the corresponding β-amino acid from the incubation solution.

3. The method of claim 2, wherein (a) further comprises:
   (i) immobilizing lysine 2,3-aminomutase on a suitable support; and
   (ii) activating the lysine 2,3-aminomutase with cofactors required for lysine 2,3-aminomutase activity; and
   (iii) contacting the L-alanine with the immobilized lysine 2,3-aminomutase to produce the corresponding β-amino acid.

4. The method of claim 1, wherein the vector that encodes lysine 2,3-aminomutase has the nucleic acid sequence of SEQ ID NO: 1.

5. The method of claim 2, wherein the cofactors required for lysine 2,3-aminomutase activity comprise:
   (i) at least one of ferrous sulfate or ferric ammonium sulfate;
   (ii) pyridoxal phosphate;
   (iii) at least one of dehydrolipoic acid, glutathione or dithiothreitol;
   (iv) S-adenosylmethionine; and
   (v) sodium dithionite.

6. The method of claim 1, further comprising separating the β-amino acid from the α-amino acid.

7. The method of claim 6, wherein the separation of the β-amino acid from the α-amino acid is achieved using high performance chromatography.

8. The method of claim 1, wherein the process is a continuous process.

9. The method of claim 2, further comprising separating the β-amino acid from the α-amino acid.

10. The method of claim 2, wherein the separation of the β-amino acid from the α-amino acid is achieved using high performance chromatography.

11. The method of claim 2, wherein the process is a continuous process.

* * * * *

SEQUENCE LISTING

<160> NUMBER OF SEQ ID NOS: 35

<210> SEQ ID NO 1
<211> LENGTH: 1251
<212> TYPE: DNA

<213> ORGANISM: Clostridium subterminale
<220> FEATURE:
<221> NAME/KEY: CDS
<222> LOCATION: (1)..(1248)

<400> SEQUENCE: 1

| | | | | | | | | | | | | | | | | |
|---|---|---|---|---|---|---|---|---|---|---|---|---|---|---|---|---|
| atg | ata | aat | aga | aga | tat | gaa | tta | ttt | aaa | gat | gtt | agc | gat | gca | gac | 48 |
| Met | Ile | Asn | Arg | Arg | Tyr | Glu | Leu | Phe | Lys | Asp | Val | Ser | Asp | Ala | Asp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tgg | aat | gac | tgg | aga | tgg | caa | gta | aga | aac | aga | ata | gaa | act | gtt | gaa | 96 |
| Trp | Asn | Asp | Trp | Arg | Trp | Gln | Val | Arg | Asn | Arg | Ile | Glu | Thr | Val | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| gaa | cta | aag | aaa | tac | ata | cca | tta | aca | aaa | gaa | gaa | gaa | gaa | gga | gta | 144 |
| Glu | Leu | Lys | Lys | Tyr | Ile | Pro | Leu | Thr | Lys | Glu | Glu | Glu | Glu | Gly | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gct | caa | tgt | gta | aaa | tca | tta | aga | atg | gct | att | act | cca | tat | tat | cta | 192 |
| Ala | Gln | Cys | Val | Lys | Ser | Leu | Arg | Met | Ala | Ile | Thr | Pro | Tyr | Tyr | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| tca | tta | atc | gat | cct | aac | gat | cct | aat | gat | cca | gta | aga | aaa | caa | gct | 240 |
| Ser | Leu | Ile | Asp | Pro | Asn | Asp | Pro | Asn | Asp | Pro | Val | Arg | Lys | Gln | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| att | cca | aca | gca | tta | gag | ctt | aac | aaa | gct | gct | gca | gat | ctt | gaa | gac | 288 |
| Ile | Pro | Thr | Ala | Leu | Glu | Leu | Asn | Lys | Ala | Ala | Ala | Asp | Leu | Glu | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| cca | tta | cat | gaa | gat | aca | gat | tca | cca | gta | cct | gga | tta | act | cac | aga | 336 |
| Pro | Leu | His | Glu | Asp | Thr | Asp | Ser | Pro | Val | Pro | Gly | Leu | Thr | His | Arg | |
| | | | 100 | | | | | 105 | | | | | 110 | | | |

| | | | | | | | | | | | | | | | | |
|---|---|---|---|---|---|---|---|---|---|---|---|---|---|---|---|---|
| tat | cca | gat | aga | gta | tta | tta | tta | ata | act | gat | atg | tgc | tca | atg | tac | 384 |
| Tyr | Pro | Asp | Arg | Val | Leu | Leu | Leu | Ile | Thr | Asp | Met | Cys | Ser | Met | Tyr | |
| | | 115 | | | | | 120 | | | | | 125 | | | | |

| | | | | | | | | | | | | | | | | |
|---|---|---|---|---|---|---|---|---|---|---|---|---|---|---|---|---|
| tgc | aga | cac | tgt | aca | aga | aga | aga | ttt | gca | gga | caa | agc | gat | gac | tct | 432 |
| Cys | Arg | His | Cys | Thr | Arg | Arg | Arg | Phe | Ala | Gly | Gln | Ser | Asp | Asp | Ser | |
| | 130 | | | | | 135 | | | | | 140 | | | | | |

| | | | | | | | | | | | | | | | | |
|---|---|---|---|---|---|---|---|---|---|---|---|---|---|---|---|---|
| atg | cca | atg | gaa | aga | ata | gat | aaa | gct | ata | gat | tat | atc | aga | aat | act | 480 |
| Met | Pro | Met | Glu | Arg | Ile | Asp | Lys | Ala | Ile | Asp | Tyr | Ile | Arg | Asn | Thr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cct | caa | gtt | aga | gac | gta | tta | tta | tca | ggt | gga | gac | gct | ctt | tta | gta | 528 |
| Pro | Gln | Val | Arg | Asp | Val | Leu | Leu | Ser | Gly | Gly | Asp | Ala | Leu | Leu | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| tct | gat | gaa | aca | tta | gaa | tac | atc | ata | gct | aaa | tta | aga | gaa | ata | cca | 576 |
| Ser | Asp | Glu | Thr | Leu | Glu | Tyr | Ile | Ile | Ala | Lys | Leu | Arg | Glu | Ile | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| cac | gtt | gaa | ata | gta | aga | ata | ggt | tca | aga | act | cca | gtt | gtt | ctt | cca | 624 |
| His | Val | Glu | Ile | Val | Arg | Ile | Gly | Ser | Arg | Thr | Pro | Val | Val | Leu | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| caa | aga | ata | act | cca | gaa | ctt | gta | aat | atg | ctt | aaa | aaa | tat | cat | cca | 672 |
| Gln | Arg | Ile | Thr | Pro | Glu | Leu | Val | Asn | Met | Leu | Lys | Lys | Tyr | His | Pro | |
| | 210 | | | | | 215 | | | | | 220 | | | | | |

| | | | | | | | | | | | | | | | | |
|---|---|---|---|---|---|---|---|---|---|---|---|---|---|---|---|---|
| gta | tgg | tta | aac | act | cac | ttt | aac | cat | cca | aat | gaa | ata | aca | gaa | gaa | 720 |
| Val | Trp | Leu | Asn | Thr | His | Phe | Asn | His | Pro | Asn | Glu | Ile | Thr | Glu | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tca | act | aga | gct | tgt | caa | tta | ctt | gct | gac | gca | gga | gta | cct | cta | gga | 768 |
| Ser | Thr | Arg | Ala | Cys | Gln | Leu | Leu | Ala | Asp | Ala | Gly | Val | Pro | Leu | Gly | |
| | | | | 245 | | | | | 250 | | | | | 255 | | |

| | | | | | | | | | | | | | | | | |
|---|---|---|---|---|---|---|---|---|---|---|---|---|---|---|---|---|
| aac | caa | tca | gtt | tta | tta | aga | gga | gtt | aac | gat | tgc | gta | cac | gta | atg | 816 |
| Asn | Gln | Ser | Val | Leu | Leu | Arg | Gly | Val | Asn | Asp | Cys | Val | His | Val | Met | |
| | | | 260 | | | | | 265 | | | | | 270 | | | |

| | | | | | | | | | | | | | | | | |
|---|---|---|---|---|---|---|---|---|---|---|---|---|---|---|---|---|
| aaa | gaa | tta | gtt | aac | aaa | tta | gta | aaa | ata | aga | gta | aga | cct | tac | tac | 864 |
| Lys | Glu | Leu | Val | Asn | Lys | Leu | Val | Lys | Ile | Arg | Val | Arg | Pro | Tyr | Tyr | |
| | | 275 | | | | | 280 | | | | | 285 | | | | |

```
atc tat caa tgt gac tta tca tta gga ctt gag cac ttc aga act cca    912
Ile Tyr Gln Cys Asp Leu Ser Leu Gly Leu Glu His Phe Arg Thr Pro
    290             295                 300 gtt tct aaa ggt atc gaa atc att gaa gga tta aga gga cat act tca    960
Val Ser Lys Gly Ile Glu Ile Ile Glu Gly Leu Arg Gly His Thr Ser
305             310                 315                 320 gga tac tgc gta cca aca ttc gtt gtt gac gct cca ggt ggt ggt gga   1008
Gly Tyr Cys Val Pro Thr Phe Val Val Asp Ala Pro Gly Gly Gly Gly
                325                 330                 335 aaa aca cca gtt atg cca aac tac gtt att tca caa agt cat gac aaa   1056
Lys Thr Pro Val Met Pro Asn Tyr Val Ile Ser Gln Ser His Asp Lys
            340                 345                 350 gta ata tta aga aac ttt gaa ggt gtt ata aca act tat tca gaa cca   1104
Val Ile Leu Arg Asn Phe Glu Gly Val Ile Thr Thr Tyr Ser Glu Pro
        355                 360                 365 ata aac tat act cca gga tgc aac tgt gat gtt tgc act ggc aag aaa   1152
Ile Asn Tyr Thr Pro Gly Cys Asn Cys Asp Val Cys Thr Gly Lys Lys
370                 375                 380 aaa gtt cat aag gtt gga gtt gct gga tta tta aac gga gaa gga atg   1200
Lys Val His Lys Val Gly Val Ala Gly Leu Leu Asn Gly Glu Gly Met
385                 390                 395                 400 gct cta gaa cca gta gga tta gag aga aat aag aga cac gtt caa gaa   1248
Ala Leu Glu Pro Val Gly Leu Glu Arg Asn Lys Arg His Val Gln Glu
                405                 410                 415 taa                                                                1251

<210> SEQ ID NO 2
<211> LENGTH: 416
<212> TYPE: PRT
<213> ORGANISM: Clostridium subterminale

<400> SEQUENCE: 2

Met Ile Asn Arg Arg Tyr Glu Leu Phe Lys Asp Val Ser Asp Ala Asp
1               5                   10                  15

Trp Asn Asp Trp Arg Trp Gln Val Arg Asn Arg Ile Glu Thr Val Glu
            20                  25                  30

Glu Leu Lys Lys Tyr Ile Pro Leu Thr Lys Glu Glu Glu Gly Val
        35                  40                  45

Ala Gln Cys Val Lys Ser Leu Arg Met Ala Ile Thr Pro Tyr Tyr Leu
    50                  55                  60

Ser Leu Ile Asp Pro Asn Asp Pro Asn Asp Pro Val Arg Lys Gln Ala
65                  70                  75                  80

Ile Pro Thr Ala Leu Glu Leu Asn Lys Ala Ala Asp Leu Glu Asp
            85                  90                  95

Pro Leu His Glu Asp Thr Asp Ser Pro Val Pro Gly Leu Thr His Arg
            100                 105                 110

Tyr Pro Asp Arg Val Leu Leu Leu Ile Thr Asp Met Cys Ser Met Tyr
        115                 120                 125

Cys Arg His Cys Thr Arg Arg Phe Ala Gly Gln Ser Asp Asp Ser
    130                 135                 140

Met Pro Met Glu Arg Ile Asp Lys Ala Ile Asp Tyr Ile Arg Asn Thr
145                 150                 155                 160

Pro Gln Val Arg Asp Val Leu Leu Ser Gly Gly Asp Ala Leu Leu Val
                165                 170                 175

Ser Asp Glu Thr Leu Glu Tyr Ile Ile Ala Lys Leu Arg Glu Ile Pro
            180                 185                 190

His Val Glu Ile Val Arg Ile Gly Ser Arg Thr Pro Val Val Leu Pro
```

```
                195                 200                 205
Gln Arg Ile Thr Pro Glu Leu Val Asn Met Leu Lys Lys Tyr His Pro
            210                 215                 220

Val Trp Leu Asn Thr His Phe Asn His Pro Asn Glu Ile Thr Glu Glu
225                 230                 235                 240

Ser Thr Arg Ala Cys Gln Leu Leu Ala Asp Ala Gly Val Pro Leu Gly
                245                 250                 255

Asn Gln Ser Val Leu Leu Arg Gly Val Asn Asp Cys Val His Val Met
            260                 265                 270

Lys Glu Leu Val Asn Lys Leu Val Lys Ile Arg Val Arg Pro Tyr Tyr
            275                 280                 285

Ile Tyr Gln Cys Asp Leu Ser Leu Gly Leu Glu His Phe Arg Thr Pro
            290                 295                 300

Val Ser Lys Gly Ile Glu Ile Ile Glu Gly Leu Arg Gly His Thr Ser
305                 310                 315                 320

Gly Tyr Cys Val Pro Thr Phe Val Asp Ala Pro Gly Gly Gly Gly
                325                 330                 335

Lys Thr Pro Val Met Pro Asn Tyr Val Ile Ser Gln Ser His Asp Lys
            340                 345                 350

Val Ile Leu Arg Asn Phe Glu Gly Val Ile Thr Thr Tyr Ser Glu Pro
            355                 360                 365

Ile Asn Tyr Thr Pro Gly Cys Asn Cys Asp Val Cys Thr Gly Lys Lys
            370                 375                 380

Lys Val His Lys Val Gly Val Ala Gly Leu Leu Asn Gly Glu Gly Met
385                 390                 395                 400

Ala Leu Glu Pro Val Gly Leu Glu Arg Asn Lys Arg His Val Gln Glu
                405                 410                 415

<210> SEQ ID NO 3
<211> LENGTH: 1029
<212> TYPE: DNA
<213> ORGANISM: Escherichia coli
<220> FEATURE:
<221> NAME/KEY: CDS
<222> LOCATION: (1)..(1026)

<400> SEQUENCE: 3 atg gcg cat att gta acc cta aat acc cca tcc aga gaa gat tgg tta      48
Met Ala His Ile Val Thr Leu Asn Thr Pro Ser Arg Glu Asp Trp Leu
  1               5                  10                  15 acg caa ctt gcc gat gtt gtg acc gat cct gat gaa ctt ctg cgt ctt      96
Thr Gln Leu Ala Asp Val Val Thr Asp Pro Asp Glu Leu Leu Arg Leu
             20                  25                  30 ttg aat ata gac gcg gag gaa aaa ctg tta gcc gga cgc agc gcc aaa     144
Leu Asn Ile Asp Ala Glu Glu Lys Leu Leu Ala Gly Arg Ser Ala Lys
         35                  40                  45 aag ctt ttt gcc ctg cgt gtg ccc cgc tca ttt atc gat cgc atg gag     192
Lys Leu Phe Ala Leu Arg Val Pro Arg Ser Phe Ile Asp Arg Met Glu
     50                  55                  60 aaa ggc aat ccg gac gat cct ctt ttg cgt cag gta ctt acc tcg caa     240
Lys Gly Asn Pro Asp Asp Pro Leu Leu Arg Gln Val Leu Thr Ser Gln
 65                  70                  75                  80 gat gag ttt gtc atc gcg ccc gga ttc tcc acc gac cca ctg gaa gaa     288
Asp Glu Phe Val Ile Ala Pro Gly Phe Ser Thr Asp Pro Leu Glu Glu
                 85                  90                  95 cag cac agc gta gtg cct ggt ttg ttg cat aaa tac cac aac cgg gcg     336
Gln His Ser Val Val Pro Gly Leu Leu His Lys Tyr His Asn Arg Ala
            100                 105                 110
```

-continued

```
ctt ttg ctg gtc aaa ggc ggc tgc gcg gta aat tgc cgc tat tgc ttc        384
Leu Leu Leu Val Lys Gly Gly Cys Ala Val Asn Cys Arg Tyr Cys Phe
        115                 120                 125 cgt cgt cac ttc ccc tat gcc gaa aat cag ggc aac aag cgt aac tgg        432
Arg Arg His Phe Pro Tyr Ala Glu Asn Gln Gly Asn Lys Arg Asn Trp
130                 135                 140 caa act gca ctt gag tat gtt gct gcg cat ccg gaa ctg gac gag atg        480
Gln Thr Ala Leu Glu Tyr Val Ala Ala His Pro Glu Leu Asp Glu Met
145                 150                 155                 160 att ttc tcc ggc ggc gat ccg ctg atg gcg aaa gat cac gag ctg gac        528
Ile Phe Ser Gly Gly Asp Pro Leu Met Ala Lys Asp His Glu Leu Asp
                165                 170                 175 tgg ttg ctc aca caa ctg gaa gcc atc ccg cat ata aaa cgt ctg cgg        576
Trp Leu Leu Thr Gln Leu Glu Ala Ile Pro His Ile Lys Arg Leu Arg
            180                 185                 190 att cac agc cgt ctg ccg att gtg atc ccg gca cgt atc acc gag gcg        624
Ile His Ser Arg Leu Pro Ile Val Ile Pro Ala Arg Ile Thr Glu Ala
        195                 200                 205 ctg gtt gaa tgc ttt gcc cgt tct acg ctg caa atc ttg ctg gtg aat        672
Leu Val Glu Cys Phe Ala Arg Ser Thr Leu Gln Ile Leu Leu Val Asn
210                 215                 220 cac atc aac cat gcc aat gag gta gat gaa aca ttc cgt cag gcg atg        720
His Ile Asn His Ala Asn Glu Val Asp Glu Thr Phe Arg Gln Ala Met
225                 230                 235                 240 gct aag ttg cgc cgg gta ggc gtt act ttg ctg aac cag agc gtt ctg        768
Ala Lys Leu Arg Arg Val Gly Val Thr Leu Leu Asn Gln Ser Val Leu
                245                 250                 255 tta cgt gat gtg aac gat aac gca caa acg ctg gca aac ctg agt aat        816
Leu Arg Asp Val Asn Asp Asn Ala Gln Thr Leu Ala Asn Leu Ser Asn
            260                 265                 270 gcg ttg ttc gat gcc ggc gta atg ccg tat tac ctg cat gtg ctc gat        864
Ala Leu Phe Asp Ala Gly Val Met Pro Tyr Tyr Leu His Val Leu Asp
        275                 280                 285 aaa gta cag ggc gcg gcg cat ttt atg gtg agt gat gac gaa gca cgg        912
Lys Val Gln Gly Ala Ala His Phe Met Val Ser Asp Asp Glu Ala Arg
    290                 295                 300 cag att atg cgt gag ttg ctg aca ctg gtg tcg gga tat ctg gtg ccg        960
Gln Ile Met Arg Glu Leu Leu Thr Leu Val Ser Gly Tyr Leu Val Pro
305                 310                 315                 320 aaa ctg gcg cga gaa att ggc ggc gaa ccc agc aaa acg ccg ctg gat       1008
Lys Leu Ala Arg Glu Ile Gly Gly Glu Pro Ser Lys Thr Pro Leu Asp
                325                 330                 335 ctc cag cta cgc cag cag taa                                           1029
Leu Gln Leu Arg Gln Gln
            340

<210> SEQ ID NO 4
<211> LENGTH: 342
<212> TYPE: PRT
<213> ORGANISM: Escherichia coli

<400> SEQUENCE: 4

Met Ala His Ile Val Thr Leu Asn Thr Pro Ser Arg Glu Asp Trp Leu
1               5                   10                  15

Thr Gln Leu Ala Asp Val Val Thr Asp Pro Asp Glu Leu Leu Arg Leu
            20                  25                  30

Leu Asn Ile Asp Ala Glu Glu Lys Leu Leu Ala Gly Arg Ser Ala Lys
        35                  40                  45

Lys Leu Phe Ala Leu Arg Val Pro Arg Ser Phe Ile Asp Arg Met Glu
```

```
                50                    55                    60
Lys Gly Asn Pro Asp Asp Pro Leu Leu Arg Gln Val Leu Thr Ser Gln
 65                      70                      75                      80

Asp Glu Phe Val Ile Ala Pro Gly Phe Ser Thr Asp Pro Leu Glu Glu
                 85                      90                      95

Gln His Ser Val Val Pro Gly Leu Leu His Lys Tyr His Asn Arg Ala
            100                     105                     110

Leu Leu Leu Val Lys Gly Gly Cys Ala Val Asn Cys Arg Tyr Cys Phe
        115                     120                     125

Arg Arg His Phe Pro Tyr Ala Glu Asn Gln Gly Asn Lys Arg Asn Trp
    130                     135                     140

Gln Thr Ala Leu Glu Tyr Val Ala Ala His Pro Glu Leu Asp Glu Met
145                     150                     155                     160

Ile Phe Ser Gly Gly Asp Pro Leu Met Ala Lys Asp His Glu Leu Asp
                165                     170                     175

Trp Leu Leu Thr Gln Leu Glu Ala Ile Pro His Ile Lys Arg Leu Arg
            180                     185                     190

Ile His Ser Arg Leu Pro Ile Val Ile Pro Ala Arg Ile Thr Glu Ala
        195                     200                     205

Leu Val Glu Cys Phe Ala Arg Ser Thr Leu Gln Ile Leu Leu Val Asn
    210                     215                     220

His Ile Asn His Ala Asn Glu Val Asp Glu Thr Phe Arg Gln Ala Met
225                     230                     235                     240

Ala Lys Leu Arg Arg Val Gly Val Thr Leu Leu Asn Gln Ser Val Leu
                245                     250                     255

Leu Arg Asp Val Asn Asp Asn Ala Gln Thr Leu Ala Asn Leu Ser Asn
            260                     265                     270

Ala Leu Phe Asp Ala Gly Val Met Pro Tyr Tyr Leu His Val Leu Asp
        275                     280                     285

Lys Val Gln Gly Ala Ala His Phe Met Val Ser Asp Asp Glu Ala Arg
    290                     295                     300

Gln Ile Met Arg Glu Leu Leu Thr Leu Val Ser Gly Tyr Leu Val Pro
305                     310                     315                     320

Lys Leu Ala Arg Glu Ile Gly Gly Glu Pro Ser Lys Thr Pro Leu Asp
                325                     330                     335

Leu Gln Leu Arg Gln Gln
            340

<210> SEQ ID NO 5
<211> LENGTH: 1017
<212> TYPE: DNA
<213> ORGANISM: Haemophilus influenzae
<220> FEATURE:
<221> NAME/KEY: CDS
<222> LOCATION: (1)..(1014)

<400> SEQUENCE: 5 atg cgt att tta ccc caa gaa ccc gtc att aga gaa gaa caa aat tgg      48
Met Arg Ile Leu Pro Gln Glu Pro Val Ile Arg Glu Glu Gln Asn Trp
 1               5                  10                  15 ctc aca att cta aaa aat gcc att tca gat cct aaa tta tta cta aaa      96
Leu Thr Ile Leu Lys Asn Ala Ile Ser Asp Pro Lys Leu Leu Leu Lys
                20                  25                  30 gcc tta aat tta cca gaa gat gat ttt gag caa tcc att gct gcg cgg     144
Ala Leu Asn Leu Pro Glu Asp Asp Phe Glu Gln Ser Ile Ala Ala Arg
            35                  40                  45
```

```
aaa ctt ttt tcg ctc cgc gtg cca caa cct ttc att gat aaa ata gaa      192
Lys Leu Phe Ser Leu Arg Val Pro Gln Pro Phe Ile Asp Lys Ile Glu
     50                  55                  60 aaa ggt aat ccg caa gat ccc ctt ttc ttg caa gtg atg tgt tct gat      240
Lys Gly Asn Pro Gln Asp Pro Leu Phe Leu Gln Val Met Cys Ser Asp
 65                  70                  75                  80 tta gag ttt gtg caa gcg gag gga ttt agt acg gat ccc tta gaa gaa      288
Leu Glu Phe Val Gln Ala Glu Gly Phe Ser Thr Asp Pro Leu Glu Glu
                 85                  90                  95 aaa aat gcc aat gcg gtg cca aat att ctt cat aaa tat aga aat cgc      336
Lys Asn Ala Asn Ala Val Pro Asn Ile Leu His Lys Tyr Arg Asn Arg
            100                 105                 110 ttg ctc ttt atg gca aaa ggc ggt tgt gcg gtg aat tgt cgt tat tgc      384
Leu Leu Phe Met Ala Lys Gly Gly Cys Ala Val Asn Cys Arg Tyr Cys
        115                 120                 125 ttt cgc cga cat ttt cct tac gat gaa aac cca gga aat aaa aaa agc      432
Phe Arg Arg His Phe Pro Tyr Asp Glu Asn Pro Gly Asn Lys Lys Ser
130                 135                 140 tgg caa ctg gcg tta gat tac att gcg gca cat tct gaa ata gaa gaa      480
Trp Gln Leu Ala Leu Asp Tyr Ile Ala Ala His Ser Glu Ile Glu Glu
145                 150                 155                 160 gtg att ttt tca ggt ggc gat cct tta atg gcg aaa gat cac gaa tta      528
Val Ile Phe Ser Gly Gly Asp Pro Leu Met Ala Lys Asp His Glu Leu
                165                 170                 175 gcg tgg tta ata aaa cat ttg gaa aat ata ccg cac tta caa cgt ttg      576
Ala Trp Leu Ile Lys His Leu Glu Asn Ile Pro His Leu Gln Arg Leu
            180                 185                 190 cgt att cac acc cgt ttg cct gtt gtg att ccg caa cgg att act gat      624
Arg Ile His Thr Arg Leu Pro Val Val Ile Pro Gln Arg Ile Thr Asp
        195                 200                 205 gaa ttt tgc act tta tta gca gaa act cgt ttg caa aca gtt atg gtg      672
Glu Phe Cys Thr Leu Leu Ala Glu Thr Arg Leu Gln Thr Val Met Val
210                 215                 220 aca cac att aat cac ccg aat gaa att gat caa att ttt gct cat gcg      720
Thr His Ile Asn His Pro Asn Glu Ile Asp Gln Ile Phe Ala His Ala
225                 230                 235                 240 atg caa aaa tta aac gcc gtg aat gtc acg ctt ttg aat caa tct gtt      768
Met Gln Lys Leu Asn Ala Val Asn Val Thr Leu Leu Asn Gln Ser Val
                245                 250                 255 ttg cta aaa ggc gtg aat gat gat gcg caa att cta aaa ata ttg agc      816
Leu Leu Lys Gly Val Asn Asp Asp Ala Gln Ile Leu Lys Ile Leu Ser
            260                 265                 270 gat aaa ctt ttt caa aca ggc att ttg cct tat tac ttg cat ttg ctg      864
Asp Lys Leu Phe Gln Thr Gly Ile Leu Pro Tyr Tyr Leu His Leu Leu
        275                 280                 285 gat aaa gtt caa ggg gcg agc cat ttt ttg att agc gat att gaa gct      912
Asp Lys Val Gln Gly Ala Ser His Phe Leu Ile Ser Asp Ile Glu Ala
290                 295                 300 atg caa atc tat aaa acc ttg caa tct ctg act tct ggc tat ctt gtt      960
Met Gln Ile Tyr Lys Thr Leu Gln Ser Leu Thr Ser Gly Tyr Leu Val
305                 310                 315                 320 cct aaa ctt gca cga gaa att gcg ggc gag cca aat aag act tta tac     1008
Pro Lys Leu Ala Arg Glu Ile Ala Gly Glu Pro Asn Lys Thr Leu Tyr
                325                 330                 335 gca gaa taa                                                         1017
Ala Glu

<210> SEQ ID NO 6
<211> LENGTH: 338
<212> TYPE: PRT
```

<213> ORGANISM: Haemophilus influenzae

<400> SEQUENCE: 6

```
Met Arg Ile Leu Pro Gln Glu Pro Val Ile Arg Glu Gln Asn Trp
 1               5                  10                  15
Leu Thr Ile Leu Lys Asn Ala Ile Ser Asp Pro Lys Leu Leu Leu Lys
                20                  25                  30
Ala Leu Asn Leu Pro Glu Asp Asp Phe Glu Gln Ser Ile Ala Ala Arg
                35                  40                  45
Lys Leu Phe Ser Leu Arg Val Pro Gln Pro Phe Ile Asp Lys Ile Glu
            50                  55                  60
Lys Gly Asn Pro Gln Asp Pro Leu Phe Leu Gln Val Met Cys Ser Asp
 65                 70                  75                  80
Leu Glu Phe Val Gln Ala Glu Gly Phe Ser Thr Asp Pro Leu Glu Glu
                85                  90                  95
Lys Asn Ala Asn Ala Val Pro Asn Ile Leu His Lys Tyr Arg Asn Arg
                100                 105                 110
Leu Leu Phe Met Ala Lys Gly Gly Cys Ala Val Asn Cys Arg Tyr Cys
            115                 120                 125
Phe Arg Arg His Phe Pro Tyr Asp Glu Asn Pro Gly Asn Lys Lys Ser
            130                 135                 140
Trp Gln Leu Ala Leu Asp Tyr Ile Ala Ala His Ser Glu Ile Glu Glu
145                 150                 155                 160
Val Ile Phe Ser Gly Gly Asp Pro Leu Met Ala Lys Asp His Glu Leu
                165                 170                 175
Ala Trp Leu Ile Lys His Leu Glu Asn Ile Pro His Leu Gln Arg Leu
                180                 185                 190
Arg Ile His Thr Arg Leu Pro Val Val Ile Pro Gln Arg Ile Thr Asp
            195                 200                 205
Glu Phe Cys Thr Leu Leu Ala Glu Thr Arg Leu Gln Thr Val Met Val
            210                 215                 220
Thr His Ile Asn His Pro Asn Glu Ile Asp Gln Ile Phe Ala His Ala
225                 230                 235                 240
Met Gln Lys Leu Asn Ala Val Asn Val Thr Leu Leu Asn Gln Ser Val
                245                 250                 255
Leu Leu Lys Gly Val Asn Asp Asp Ala Gln Ile Leu Lys Ile Leu Ser
            260                 265                 270
Asp Lys Leu Phe Gln Thr Gly Ile Leu Pro Tyr Tyr Leu His Leu Leu
            275                 280                 285
Asp Lys Val Gln Gly Ala Ser His Phe Leu Ile Ser Asp Ile Glu Ala
            290                 295                 300
Met Gln Ile Tyr Lys Thr Leu Gln Ser Leu Thr Ser Gly Tyr Leu Val
305                 310                 315                 320
Pro Lys Leu Ala Arg Glu Ile Ala Gly Glu Pro Asn Lys Thr Leu Tyr
                325                 330                 335
Ala Glu
```

<210> SEQ ID NO 7
<211> LENGTH: 1251
<212> TYPE: DNA
<213> ORGANISM: Porphyromonas gingivalis
<220> FEATURE:
<221> NAME/KEY: CDS
<222> LOCATION: (1)..(1248)

<400> SEQUENCE: 7

```
                                            -continued atg gca gaa agt cgt aga aag tat tat ttc cct gat gtc acc gat gag      48
Met Ala Glu Ser Arg Arg Lys Tyr Tyr Phe Pro Asp Val Thr Asp Glu
  1               5                  10                  15 caa tgg aac gac tgg cat tgg cag gtc ctc aat cga att gag acg ctc      96
Gln Trp Asn Asp Trp His Trp Gln Val Leu Asn Arg Ile Glu Thr Leu
             20                  25                  30 gac cag ctg aaa aag tac gtt aca ctc acc gct gaa gaa gaa gag gga     144
Asp Gln Leu Lys Lys Tyr Val Thr Leu Thr Ala Glu Glu Glu Glu Gly
         35                  40                  45 gta aaa gaa tcg ctc aaa gta ctc cga atg gct atc aca cct tat tat     192
Val Lys Glu Ser Leu Lys Val Leu Arg Met Ala Ile Thr Pro Tyr Tyr
 50                  55                  60 ttg agt ttg ata gac ccc gag aat cct aat tgt ccg att cgt aaa caa     240
Leu Ser Leu Ile Asp Pro Glu Asn Pro Asn Cys Pro Ile Arg Lys Gln
 65                  70                  75                  80 gcc att cct act cat cag gaa ctg gta cgt gct cct gaa gat cag gta     288
Ala Ile Pro Thr His Gln Glu Leu Val Arg Ala Pro Glu Asp Gln Val
                 85                  90                  95 gac cca ctt agt gaa gat gaa gat tcg ccc gta ccc gga ctg act cat     336
Asp Pro Leu Ser Glu Asp Glu Asp Ser Pro Val Pro Gly Leu Thr His
            100                 105                 110 cgt tat ccg gat cgt gta ttg ttc ctt atc acg gac aaa tgt tcg atg     384
Arg Tyr Pro Asp Arg Val Leu Phe Leu Ile Thr Asp Lys Cys Ser Met
        115                 120                 125 tac tgt cgt cat tgt act cgc cgt cgc ttc gca gga cag aaa gat gct     432
Tyr Cys Arg His Cys Thr Arg Arg Arg Phe Ala Gly Gln Lys Asp Ala
    130                 135                 140 tct tct cct tct gag cgc atc gat cga tgc att gac tat ata gcc aat     480
Ser Ser Pro Ser Glu Arg Ile Asp Arg Cys Ile Asp Tyr Ile Ala Asn
145                 150                 155                 160 aca ccg aca gtc cgc gat gtt ttg cta tcg gga ggc gat gcc ctc ctt     528
Thr Pro Thr Val Arg Asp Val Leu Leu Ser Gly Gly Asp Ala Leu Leu
                165                 170                 175 gtc agc gac gaa cgc ttg gaa tac ata ttg aag cgt ctg cgc gaa ata     576
Val Ser Asp Glu Arg Leu Glu Tyr Ile Leu Lys Arg Leu Arg Glu Ile
            180                 185                 190 cct cat gtg gag att gtt cgt ata gga agc cgt acg ccg gta gtc ctt     624
Pro His Val Glu Ile Val Arg Ile Gly Ser Arg Thr Pro Val Val Leu
        195                 200                 205 cct cag cgt ata acg cct caa ttg gtg gat atg ctc aaa aaa tat cat     672
Pro Gln Arg Ile Thr Pro Gln Leu Val Asp Met Leu Lys Lys Tyr His
    210                 215                 220 ccg gtg tgg ctg aac act cac ttc aac cac ccg aat gaa gtt acc gaa     720
Pro Val Trp Leu Asn Thr His Phe Asn His Pro Asn Glu Val Thr Glu
225                 230                 235                 240 gaa gca gta gag gct tgt gaa aga atg gcc aat gcc ggt att ccg ttg     768
Glu Ala Val Glu Ala Cys Glu Arg Met Ala Asn Ala Gly Ile Pro Leu
                245                 250                 255 ggt aac caa acg gtt tta ttg cgt gga atc aat gat tgt aca cat gtg     816
Gly Asn Gln Thr Val Leu Leu Arg Gly Ile Asn Asp Cys Thr His Val
            260                 265                 270 atg aag aga ttg gta cat ttg ctg gta aag atg cgt gtg cgt cct tac     864
Met Lys Arg Leu Val His Leu Leu Val Lys Met Arg Val Arg Pro Tyr
        275                 280                 285 tat ata tat gta tgc gat ctt tcg ctt gga ata ggt cat ttc cgc acg     912
Tyr Ile Tyr Val Cys Asp Leu Ser Leu Gly Ile Gly His Phe Arg Thr
    290                 295                 300 ccg gta tct aaa gga atc gaa att atc gaa aat ttg cgc gga cac acc     960
Pro Val Ser Lys Gly Ile Glu Ile Ile Glu Asn Leu Arg Gly His Thr
```

-continued

```
                305                 310                 315                 320
tcg ggc tat gct gtt cct acc ttt gtg gta gat gct ccg ggg ggt ggt          1008
Ser Gly Tyr Ala Val Pro Thr Phe Val Val Asp Ala Pro Gly Gly Gly
                    325                 330                 335 ggt aag ata cct gta atg ccg aac tat gtt gta tct cag tcc cca cga          1056
Gly Lys Ile Pro Val Met Pro Asn Tyr Val Val Ser Gln Ser Pro Arg
        340                 345                 350 cat gtg gtt ctt cgc aat tat gaa ggt gtt atc aca acc tat acg gag          1104
His Val Val Leu Arg Asn Tyr Glu Gly Val Ile Thr Thr Tyr Thr Glu
            355                 360                 365 ccg gag aat tat cat gag gag tgt gat tgt gag gac tgt cga gcc ggt          1152
Pro Glu Asn Tyr His Glu Glu Cys Asp Cys Glu Asp Cys Arg Ala Gly
        370                 375                 380 aag cat aaa gag ggt gta gct gca ctt tcc gga ggt cag cag ttg gct          1200
Lys His Lys Glu Gly Val Ala Ala Leu Ser Gly Gly Gln Gln Leu Ala
385                 390                 395                 400 atc gag cct tcc gac tta gct cgc aaa aaa cgc aag ttt gat aag aac          1248
Ile Glu Pro Ser Asp Leu Ala Arg Lys Lys Arg Lys Phe Asp Lys Asn
                405                 410                 415 tga                                                                       1251
```

<210> SEQ ID NO 8
<211> LENGTH: 416
<212> TYPE: PRT
<213> ORGANISM: Porphyromonas gingivalis

<400> SEQUENCE: 8

```
Met Ala Glu Ser Arg Arg Lys Tyr Tyr Phe Pro Asp Val Thr Asp Glu
1               5                   10                  15

Gln Trp Asn Asp Trp His Trp Gln Val Leu Asn Arg Ile Glu Thr Leu
            20                  25                  30

Asp Gln Leu Lys Lys Tyr Val Thr Leu Thr Ala Glu Glu Glu Glu Gly
        35                  40                  45

Val Lys Glu Ser Leu Lys Val Leu Arg Met Ala Ile Thr Pro Tyr Tyr
    50                  55                  60

Leu Ser Leu Ile Asp Pro Glu Asn Pro Asn Cys Pro Ile Arg Lys Gln
65                  70                  75                  80

Ala Ile Pro Thr His Gln Glu Leu Val Arg Ala Pro Glu Asp Gln Val
                85                  90                  95

Asp Pro Leu Ser Glu Asp Glu Ser Pro Val Pro Gly Leu Thr His
            100                 105                 110

Arg Tyr Pro Asp Arg Val Leu Phe Leu Ile Thr Asp Lys Cys Ser Met
        115                 120                 125

Tyr Cys Arg His Cys Thr Arg Arg Phe Ala Gly Gln Lys Asp Ala
    130                 135                 140

Ser Ser Pro Ser Glu Arg Ile Asp Arg Cys Ile Asp Tyr Ile Ala Asn
145                 150                 155                 160

Thr Pro Thr Val Arg Asp Val Leu Leu Ser Gly Gly Asp Ala Leu Leu
                165                 170                 175

Val Ser Asp Glu Arg Leu Glu Tyr Ile Leu Lys Arg Leu Arg Glu Ile
            180                 185                 190

Pro His Val Glu Ile Val Arg Ile Gly Ser Arg Thr Pro Val Val Leu
        195                 200                 205

Pro Gln Arg Ile Thr Pro Gln Leu Val Asp Met Leu Lys Lys Tyr His
    210                 215                 220

Pro Val Trp Leu Asn Thr His Phe Asn His Pro Asn Glu Val Thr Glu
```

-continued

```
                    225                 230                 235                 240

Glu Ala Val Glu Ala Cys Glu Arg Met Ala Asn Ala Gly Ile Pro Leu
                        245                 250                 255

Gly Asn Gln Thr Val Leu Leu Arg Gly Ile Asn Asp Cys Thr His Val
                    260                 265                 270

Met Lys Arg Leu Val His Leu Val Lys Met Arg Val Arg Pro Tyr
                275                 280                 285

Tyr Ile Tyr Val Cys Asp Leu Ser Leu Gly Ile Gly His Phe Arg Thr
                290                 295                 300

Pro Val Ser Lys Gly Ile Glu Ile Ile Glu Asn Leu Arg Gly His Thr
        305                 310                 315                 320

Ser Gly Tyr Ala Val Pro Thr Phe Val Val Asp Ala Pro Gly Gly Gly
                        325                 330                 335

Gly Lys Ile Pro Val Met Pro Asn Tyr Val Val Ser Gln Ser Pro Arg
                        340                 345                 350

His Val Leu Arg Asn Tyr Glu Gly Val Ile Thr Thr Tyr Thr Glu
                    355                 360                 365

Pro Glu Asn Tyr His Glu Glu Cys Asp Cys Glu Asp Cys Arg Ala Gly
        370                 375                 380

Lys His Lys Glu Gly Val Ala Ala Leu Ser Gly Gly Gln Gln Leu Ala
        385                 390                 395                 400

Ile Glu Pro Ser Asp Leu Ala Arg Lys Lys Arg Lys Phe Asp Lys Asn
                        405                 410                 415

<210> SEQ ID NO 9
<211> LENGTH: 1416
<212> TYPE: DNA
<213> ORGANISM: Bacillus subtilis
<220> FEATURE:
<221> NAME/KEY: CDS
<222> LOCATION: (1)..(1413)

<400> SEQUENCE: 9 atg aaa aac aaa tgg tat aaa ccg aaa cgg cat tgg aag gag atc gag        48
Met Lys Asn Lys Trp Tyr Lys Pro Lys Arg His Trp Lys Glu Ile Glu
  1               5                  10                  15 tta tgg aag gac gtt ccg gaa gag aaa tgg aac gat tgg ctt tgg cag        96
Leu Trp Lys Asp Val Pro Glu Glu Lys Trp Asn Asp Trp Leu Trp Gln
             20                  25                  30 ctg aca cac act gta aga acg tta gat gat tta aag aaa gtc att aat       144
Leu Thr His Thr Val Arg Thr Leu Asp Asp Leu Lys Lys Val Ile Asn
         35                  40                  45 ctg acc gag gat gaa gag gaa ggc gtc aga att tct acc aaa acg atc       192
Leu Thr Glu Asp Glu Glu Glu Gly Val Arg Ile Ser Thr Lys Thr Ile
     50                  55                  60 ccc tta aat att aca cct tac tat gct tct tta atg gac ccc gac aat       240
Pro Leu Asn Ile Thr Pro Tyr Tyr Ala Ser Leu Met Asp Pro Asp Asn
 65                  70                  75                  80 ccg aga tgc ccg gta cgc atg cag tct gtg ccg ctt tct gaa gaa atg       288
Pro Arg Cys Pro Val Arg Met Gln Ser Val Pro Leu Ser Glu Glu Met
                 85                  90                  95 cac aaa aca aaa tac gat ctg gaa gac ccg ctt cat gag gat gaa gat       336
His Lys Thr Lys Tyr Asp Leu Glu Asp Pro Leu His Glu Asp Glu Asp
            100                 105                 110 tca ccg gta ccc ggt ctg aca cac cgc tat ccc gac cgt gtg ctg ttt       384
Ser Pro Val Pro Gly Leu Thr His Arg Tyr Pro Asp Arg Val Leu Phe
        115                 120                 125 ctt gtc acg aat caa tgt tcc atg tac tgc cgc tac tgc aca aga agg       432
```

```
                Leu Val Thr Asn Gln Cys Ser Met Tyr Cys Arg Tyr Cys Thr Arg Arg
                    130                 135                 140 cgc ttt tcc gga caa atc gga atg ggc gtc ccc aaa aaa cag ctt gat         480
Arg Phe Ser Gly Gln Ile Gly Met Gly Val Pro Lys Lys Gln Leu Asp
145                 150                 155                 160 gct gca att gct tat atc cgg gaa aca ccc gaa atc cgc gat tgt tta         528
Ala Ala Ile Ala Tyr Ile Arg Glu Thr Pro Glu Ile Arg Asp Cys Leu
                    165                 170                 175 att tca ggc ggt gat ggg ctg ctc atc aac gac caa att tta gaa tat         576
Ile Ser Gly Gly Asp Gly Leu Leu Ile Asn Asp Gln Ile Leu Glu Tyr
                180                 185                 190 att tta aaa gag ctg cgc agc att ccg cat ctg gaa gtc atc aga atc         624
Ile Leu Lys Glu Leu Arg Ser Ile Pro His Leu Glu Val Ile Arg Ile
        195                 200                 205 gga aca aga gct ccc gtc gtc ttt ccg cag cgc att acc gat cat ctg         672
Gly Thr Arg Ala Pro Val Val Phe Pro Gln Arg Ile Thr Asp His Leu
    210                 215                 220 tgc gag ata ttg aaa aaa tat cat ccg gtc tgg ctg aac acc cat ttt         720
Cys Glu Ile Leu Lys Lys Tyr His Pro Val Trp Leu Asn Thr His Phe
225                 230                 235                 240 aac aca agc atc gaa atg aca gaa gaa tcc gtt gag gca tgt gaa aag         768
Asn Thr Ser Ile Glu Met Thr Glu Glu Ser Val Glu Ala Cys Glu Lys
                    245                 250                 255 ctg gtg aac gcg gga gtc ccg gtc gga aat cag gct gtc gta tta gca         816
Leu Val Asn Ala Gly Val Pro Val Gly Asn Gln Ala Val Val Leu Ala
                260                 265                 270 ggt att aat gat tcg gtt cca att atg aaa aag ctc atg cat gac ttg         864
Gly Ile Asn Asp Ser Val Pro Ile Met Lys Lys Leu Met His Asp Leu
            275                 280                 285 gta aaa atc aga gtc cgt cct tat tat att tac caa tgt gat ctg tca         912
Val Lys Ile Arg Val Arg Pro Tyr Tyr Ile Tyr Gln Cys Asp Leu Ser
        290                 295                 300 gaa gga ata ggg cat ttc aga gct cct gtt tcc aaa ggt ttg gag atc         960
Glu Gly Ile Gly His Phe Arg Ala Pro Val Ser Lys Gly Leu Glu Ile
305                 310                 315                 320 att gaa ggg ctg aga ggt cat acc tca ggc tat gcg gtt cct acc ttt         1008
Ile Glu Gly Leu Arg Gly His Thr Ser Gly Tyr Ala Val Pro Thr Phe
                    325                 330                 335 gtc gtt gac gca cca ggc gga gga ggt aaa atc gcc ctg cag cca aac         1056
Val Val Asp Ala Pro Gly Gly Gly Gly Lys Ile Ala Leu Gln Pro Asn
                340                 345                 350 tat gtc ctg tca caa agt cct gac aaa gtg atc tta aga aat ttt gaa         1104
Tyr Val Leu Ser Gln Ser Pro Asp Lys Val Ile Leu Arg Asn Phe Glu
            355                 360                 365 ggt gtg att acg tca tat ccg gaa cca gag aat tat atc ccc aat cag         1152
Gly Val Ile Thr Ser Tyr Pro Glu Pro Glu Asn Tyr Ile Pro Asn Gln
        370                 375                 380 gca gac gcc tat ttt gag tcc gtt ttc cct gaa acc gct gac aaa aag         1200
Ala Asp Ala Tyr Phe Glu Ser Val Phe Pro Glu Thr Ala Asp Lys Lys
385                 390                 395                 400 gag ccg atc ggg ctg agt gcc att ttt gct gac aaa gaa gtt tcg ttt         1248
Glu Pro Ile Gly Leu Ser Ala Ile Phe Ala Asp Lys Glu Val Ser Phe
                    405                 410                 415 aca cct gaa aat gta gac aga atc aaa agg aga gag gca tac atc gca         1296
Thr Pro Glu Asn Val Asp Arg Ile Lys Arg Arg Glu Ala Tyr Ile Ala
                420                 425                 430 aat ccg gag cat gaa aca tta aaa gat cgg cgt gag aaa aga gat cag         1344
Asn Pro Glu His Glu Thr Leu Lys Asp Arg Arg Glu Lys Arg Asp Gln
            435                 440                 445
```

```
ctc aaa gaa aag aaa ttt ttg gcg cag cag aaa aaa cag aaa gag act    1392
Leu Lys Glu Lys Lys Phe Leu Ala Gln Gln Lys Lys Gln Lys Glu Thr
    450                 455                 460 gaa tgc gga ggg gat tct tca tga                                    1416
Glu Cys Gly Gly Asp Ser Ser
465                 470
```

<210> SEQ ID NO 10
<211> LENGTH: 471
<212> TYPE: PRT
<213> ORGANISM: Bacillus subtilis

<400> SEQUENCE: 10

```
Met Lys Asn Lys Trp Tyr Lys Pro Lys Arg His Trp Lys Glu Ile Glu
1               5                   10                  15

Leu Trp Lys Asp Val Pro Glu Glu Lys Trp Asn Asp Trp Leu Trp Gln
            20                  25                  30

Leu Thr His Thr Val Arg Thr Leu Asp Asp Leu Lys Lys Val Ile Asn
        35                  40                  45

Leu Thr Glu Asp Glu Glu Gly Val Arg Ile Ser Thr Lys Thr Ile
    50                  55                  60

Pro Leu Asn Ile Thr Pro Tyr Tyr Ala Ser Leu Met Asp Pro Asp Asn
65                  70                  75                  80

Pro Arg Cys Pro Val Arg Met Gln Ser Val Pro Leu Ser Glu Glu Met
                85                  90                  95

His Lys Thr Lys Tyr Asp Leu Glu Asp Pro Leu His Glu Asp Glu Asp
            100                 105                 110

Ser Pro Val Pro Gly Leu Thr His Arg Tyr Pro Asp Arg Val Leu Phe
        115                 120                 125

Leu Val Thr Asn Gln Cys Ser Met Tyr Cys Arg Tyr Cys Thr Arg Arg
    130                 135                 140

Arg Phe Ser Gly Gln Ile Gly Met Gly Val Pro Lys Lys Gln Leu Asp
145                 150                 155                 160

Ala Ala Ile Ala Tyr Ile Arg Glu Thr Pro Glu Ile Arg Asp Cys Leu
                165                 170                 175

Ile Ser Gly Gly Asp Gly Leu Leu Ile Asn Asp Gln Ile Leu Glu Tyr
            180                 185                 190

Ile Leu Lys Glu Leu Arg Ser Ile Pro His Leu Glu Val Ile Arg Ile
        195                 200                 205

Gly Thr Arg Ala Pro Val Val Phe Pro Gln Arg Ile Thr Asp His Leu
    210                 215                 220

Cys Glu Ile Leu Lys Lys Tyr His Pro Val Trp Leu Asn Thr His Phe
225                 230                 235                 240

Asn Thr Ser Ile Glu Met Thr Glu Glu Ser Val Glu Ala Cys Glu Lys
                245                 250                 255

Leu Val Asn Ala Gly Val Pro Val Gly Asn Gln Ala Val Val Leu Ala
            260                 265                 270

Gly Ile Asn Asp Ser Val Pro Ile Met Lys Lys Leu Met His Asp Leu
        275                 280                 285

Val Lys Ile Arg Val Arg Pro Tyr Tyr Ile Tyr Gln Cys Asp Leu Ser
    290                 295                 300

Glu Gly Ile Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335
```

```
Val Val Asp Ala Pro Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
    370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
                405                 410                 415

Thr Pro Glu Asn Val Asp Arg Ile Lys Arg Arg Glu Ala Tyr Ile Ala
                420                 425                 430

Asn Pro Glu His Glu Thr Leu Lys Asp Arg Arg Glu Lys Arg Asp Gln
            435                 440                 445

Leu Lys Glu Lys Lys Phe Leu Ala Gln Gln Lys Lys Gln Lys Glu Thr
450                 455                 460

Glu Cys Gly Gly Asp Ser Ser
465                 470

<210> SEQ ID NO 11
<211> LENGTH: 1188
<212> TYPE: DNA
<213> ORGANISM: Deinococcus radiodurans
<220> FEATURE:
<221> NAME/KEY: CDS
<222> LOCATION: (1)..(1188)

<400> SEQUENCE: 11
```

| | | | | | | | | | | | | | | | | |
|---|---|---|---|---|---|---|---|---|---|---|---|---|---|---|---|---|
| tgg | caa | ggc | gta | ccc | gac | gag | cag | tgg | tac | gac | tgg | aaa | tgg | cag | ctc | 48 |
| Trp | Gln | Gly | Val | Pro | Asp | Glu | Gln | Trp | Tyr | Asp | Trp | Lys | Trp | Gln | Leu | |
| 1 | | | | 5 | | | | | 10 | | | | | 15 | | |
| aag | aac | cgc | atc | aac | agt | gtg | gag | gag | ttg | cag | gaa | gtc | ctg | acc | ctc | 96 |
| Lys | Asn | Arg | Ile | Asn | Ser | Val | Glu | Glu | Leu | Gln | Glu | Val | Leu | Thr | Leu | |
| | | | 20 | | | | | 25 | | | | | 30 | | | |
| acc | gag | tcc | gag | tac | cgg | ggt | gcg | tcc | gcc | gag | ggc | att | ttc | cgc | ctc | 144 |
| Thr | Glu | Ser | Glu | Tyr | Arg | Gly | Ala | Ser | Ala | Glu | Gly | Ile | Phe | Arg | Leu | |
| | | 35 | | | | | 40 | | | | | 45 | | | | |
| gac | atc | acg | ccg | tat | ttc | gcg | tcc | ctc | atg | gac | ccc | gaa | gac | ccc | acc | 192 |
| Asp | Ile | Thr | Pro | Tyr | Phe | Ala | Ser | Leu | Met | Asp | Pro | Glu | Asp | Pro | Thr | |
| | 50 | | | | | 55 | | | | | 60 | | | | | |
| tgc | ccg | gtg | cgc | cgt | cag | gtg | att | ccc | acc | gag | gag | gag | ctc | cag | ccg | 240 |
| Cys | Pro | Val | Arg | Arg | Gln | Val | Ile | Pro | Thr | Glu | Glu | Glu | Leu | Gln | Pro | |
| 65 | | | | 70 | | | | | 75 | | | | | 80 | | |
| ttc | acc | tcc | atg | atg | gaa | gac | tct | ctc | gcg | gag | gat | aag | cac | tcg | ccc | 288 |
| Phe | Thr | Ser | Met | Met | Glu | Asp | Ser | Leu | Ala | Glu | Asp | Lys | His | Ser | Pro | |
| | | | | 85 | | | | | 90 | | | | | 95 | | |
| gtg | ccg | ggg | ctg | gtg | cac | cgc | tac | ccc | gac | cgc | gtg | ctg | atg | ctg | gtc | 336 |
| Val | Pro | Gly | Leu | Val | His | Arg | Tyr | Pro | Asp | Arg | Val | Leu | Met | Leu | Val | |
| | | | 100 | | | | | 105 | | | | | 110 | | | |
| acg | acc | cag | tgc | gcg | agc | tac | tgc | cgc | tac | tgc | acc | cga | agc | cgc | atc | 384 |
| Thr | Thr | Gln | Cys | Ala | Ser | Tyr | Cys | Arg | Tyr | Cys | Thr | Arg | Ser | Arg | Ile | |
| | | 115 | | | | | 120 | | | | | 125 | | | | |
| gtg | ggc | gac | ccc | acc | gag | acg | ttc | aat | ccc | gcc | gag | tat | gag | gcg | cag | 432 |
| Val | Gly | Asp | Pro | Thr | Glu | Thr | Phe | Asn | Pro | Ala | Glu | Tyr | Glu | Ala | Gln | |
| | 130 | | | | | 135 | | | | | 140 | | | | | |
| ctc | aac | tac | ctg | cgc | aac | acc | ccg | cag | gtg | cgc | gac | gtg | ctg | ctt | tcc | 480 |
| Leu | Asn | Tyr | Leu | Arg | Asn | Thr | Pro | Gln | Val | Arg | Asp | Val | Leu | Leu | Ser | |
| 145 | | | | 150 | | | | | 155 | | | | | 160 | | |
| ggc | ggc | gac | ccg | ctc | aca | ctc | gcg | ccg | aag | gtg | ctg | ggg | cgc | ctg | ctt | 528 |

```
Gly Gly Asp Pro Leu Thr Leu Ala Pro Lys Val Leu Gly Arg Leu Leu
            165                 170                 175 tcc gaa ctt cgt aaa atc gag cac atc gaa atc atc cgc atc ggc acc    576
Ser Glu Leu Arg Lys Ile Glu His Ile Glu Ile Ile Arg Ile Gly Thr
            180                 185                 190 cgc gtg ccc gtg ttc atg ccc atg cgc gtg acc cag gaa ctg tgc gac    624
Arg Val Pro Val Phe Met Pro Met Arg Val Thr Gln Glu Leu Cys Asp
            195                 200                 205 acg ctc gcc gaa cac cat ccg ctg tgg atg aac att cac gtc aac cac    672
Thr Leu Ala Glu His His Pro Leu Trp Met Asn Ile His Val Asn His
    210                 215                 220 ccc aag gaa atc acc ccc gaa gtg gcc gag gcg tgt gac cgt ctg acc    720
Pro Lys Glu Ile Thr Pro Glu Val Ala Glu Ala Cys Asp Arg Leu Thr
225                 230                 235                 240 cgc gcg ggc gtg ccg ctc ggc aac cag agc gtg ctg ctg cgc ggc gtg    768
Arg Ala Gly Val Pro Leu Gly Asn Gln Ser Val Leu Leu Arg Gly Val
                245                 250                 255 aac gac cac ccg gtc atc atg caa aag ctg ctg cgc gag ctc gtc aaa    816
Asn Asp His Pro Val Ile Met Gln Lys Leu Leu Arg Glu Leu Val Lys
            260                 265                 270 att cgg gtg cgc ccc tac tac atc tac cag tgc gac ctc gtg cac ggc    864
Ile Arg Val Arg Pro Tyr Tyr Ile Tyr Gln Cys Asp Leu Val His Gly
            275                 280                 285 gct ggg cac ctg cgc acc acg gtc agt aag ggt ctg gaa atc atg gaa    912
Ala Gly His Leu Arg Thr Thr Val Ser Lys Gly Leu Glu Ile Met Glu
    290                 295                 300 tcg ctg cgc ggc cac acc tcc ggc tac agc gtg ccg acc tac gtg gtg    960
Ser Leu Arg Gly His Thr Ser Gly Tyr Ser Val Pro Thr Tyr Val Val
305                 310                 315                 320 gac gcg ccc ggc ggc ggc aag att ccg gtg gcg ccc aac tac gtg         1008
Asp Ala Pro Gly Gly Gly Lys Ile Pro Val Ala Pro Asn Tyr Val
                325                 330                 335 ctc tcg cac agc cct gag aag ctg att ctg cgc aac ttc gag ggc tac    1056
Leu Ser His Ser Pro Glu Lys Leu Ile Leu Arg Asn Phe Glu Gly Tyr
            340                 345                 350 atc gcc gcc tac tcg gag ccc acc gat tac acc ggc ccc gac atg gcg    1104
Ile Ala Ala Tyr Ser Glu Pro Thr Asp Tyr Thr Gly Pro Asp Met Ala
            355                 360                 365 att cct gac gac tgg att cgc aag gaa ccc ggc cag acc ggc atc ttc    1152
Ile Pro Asp Asp Trp Ile Arg Lys Glu Pro Gly Gln Thr Gly Ile Phe
    370                 375                 380 ggc ctg atg gaa ggc gag cgc att tcc atc gag ccg                    1188
Gly Leu Met Glu Gly Glu Arg Ile Ser Ile Glu Pro
385                 390                 395

<210> SEQ ID NO 12
<211> LENGTH: 396
<212> TYPE: PRT
<213> ORGANISM: Deinococcus radiodurans

<400> SEQUENCE: 12

Trp Gln Gly Val Pro Asp Glu Gln Trp Tyr Asp Trp Lys Trp Gln Leu
 1               5                  10                  15

Lys Asn Arg Ile Asn Ser Val Glu Glu Leu Gln Glu Val Leu Thr Leu
            20                  25                  30

Thr Glu Ser Glu Tyr Arg Gly Ala Ser Ala Glu Gly Ile Phe Arg Leu
        35                  40                  45

Asp Ile Thr Pro Tyr Phe Ala Ser Leu Met Asp Pro Glu Asp Pro Thr
    50                  55                  60
```

```
Cys Pro Val Arg Arg Gln Val Ile Pro Thr Glu Glu Leu Gln Pro
 65                  70                  75                  80

Phe Thr Ser Met Met Glu Asp Ser Leu Ala Glu Asp Lys His Ser Pro
                 85                  90                  95

Val Pro Gly Leu Val His Arg Tyr Pro Asp Arg Val Leu Met Leu Val
            100                 105                 110

Thr Thr Gln Cys Ala Ser Tyr Cys Arg Tyr Cys Thr Arg Ser Arg Ile
            115                 120                 125

Val Gly Asp Pro Thr Glu Thr Phe Asn Pro Ala Glu Tyr Glu Ala Gln
            130                 135                 140

Leu Asn Tyr Leu Arg Asn Thr Pro Gln Val Arg Asp Val Leu Leu Ser
145                 150                 155                 160

Gly Gly Asp Pro Leu Thr Leu Ala Pro Lys Val Leu Gly Arg Leu Leu
                165                 170                 175

Ser Glu Leu Arg Lys Ile Glu His Ile Glu Ile Ile Arg Ile Gly Thr
            180                 185                 190

Arg Val Pro Val Phe Met Pro Met Arg Val Thr Gln Glu Leu Cys Asp
            195                 200                 205

Thr Leu Ala Glu His His Pro Leu Trp Met Asn Ile His Val Asn His
210                 215                 220

Pro Lys Glu Ile Thr Pro Glu Val Ala Glu Ala Cys Asp Arg Leu Thr
225                 230                 235                 240

Arg Ala Gly Val Pro Leu Gly Asn Gln Ser Val Leu Leu Arg Gly Val
                245                 250                 255

Asn Asp His Pro Val Ile Met Gln Lys Leu Leu Arg Glu Leu Val Lys
            260                 265                 270

Ile Arg Val Arg Pro Tyr Tyr Ile Tyr Gln Cys Asp Leu Val His Gly
            275                 280                 285

Ala Gly His Leu Arg Thr Thr Val Ser Lys Gly Leu Glu Ile Met Glu
            290                 295                 300

Ser Leu Arg Gly His Thr Ser Gly Tyr Ser Val Pro Thr Tyr Val Val
305                 310                 315                 320

Asp Ala Pro Gly Gly Gly Lys Ile Pro Val Ala Pro Asn Tyr Val
                325                 330                 335

Leu Ser His Ser Pro Glu Lys Leu Ile Leu Arg Asn Phe Glu Gly Tyr
            340                 345                 350

Ile Ala Ala Tyr Ser Glu Pro Thr Asp Tyr Thr Gly Pro Asp Met Ala
            355                 360                 365

Ile Pro Asp Asp Trp Ile Arg Lys Glu Pro Gly Gln Thr Gly Ile Phe
370                 375                 380

Gly Leu Met Glu Gly Glu Arg Ile Ser Ile Glu Pro
385                 390                 395
```

<210> SEQ ID NO 13  
<211> LENGTH: 1113  
<212> TYPE: DNA  
<213> ORGANISM: Aquifex aeolicus  
<220> FEATURE:  
<221> NAME/KEY: CDS  
<222> LOCATION: (1)..(1110)

<400> SEQUENCE: 13

```
atg cgt cgc ttt ttt gag aat gta ccg gaa aac ctc tgg agg agc tac      48
Met Arg Arg Phe Phe Glu Asn Val Pro Glu Asn Leu Trp Arg Ser Tyr
  1               5                  10                  15 gag tgg cag ata caa aac agg ata aaa act ctt aag gag ata aaa aag      96
```

-continued

```
Glu Trp Gln Ile Gln Asn Arg Ile Lys Thr Leu Lys Glu Ile Lys Lys
        20                  25                  30 tac tta aaa ctc ctt ccc gag gag gaa gaa gga att aaa aga act caa      144
Tyr Leu Lys Leu Leu Pro Glu Glu Glu Glu Gly Ile Lys Arg Thr Gln
        35                  40                  45 ggg ctt tat ccc ttt gcg ata aca cct tac tac ctc tct tta ata aat      192
Gly Leu Tyr Pro Phe Ala Ile Thr Pro Tyr Tyr Leu Ser Leu Ile Asn
        50                  55                  60 cca gag gac ccg aag gat cct ata aga ctt cag gca atc ccc cgc gtt      240
Pro Glu Asp Pro Lys Asp Pro Ile Arg Leu Gln Ala Ile Pro Arg Val
65                  70                  75                  80 gta gaa gtt gat gaa aag gtt cag tct gcg gga gaa cca gac gct ctg      288
Val Glu Val Asp Glu Lys Val Gln Ser Ala Gly Glu Pro Asp Ala Leu
                85                  90                  95 aaa gaa gaa gga gat att ccg ggt ctt aca cac agg tat ccc gac agg      336
Lys Glu Glu Gly Asp Ile Pro Gly Leu Thr His Arg Tyr Pro Asp Arg
            100                 105                 110 gtt ctt tta aac gtc act acc ttt tgt gcg gtt tac tgc agg cac tgt      384
Val Leu Leu Asn Val Thr Thr Phe Cys Ala Val Tyr Cys Arg His Cys
            115                 120                 125 atg aga aag agg ata ttc tct cag ggt gag agg gca agg act aaa gag      432
Met Arg Lys Arg Ile Phe Ser Gln Gly Glu Arg Ala Arg Thr Lys Glu
130                 135                 140 gaa ata gac acg atg att gat tac ata aag aga cac gaa gag ata agg      480
Glu Ile Asp Thr Met Ile Asp Tyr Ile Lys Arg His Glu Glu Ile Arg
145                 150                 155                 160 gat gtc tta att tca ggt ggt gag cca ctt tcc ctt tcc ttg gaa aaa      528
Asp Val Leu Ile Ser Gly Gly Glu Pro Leu Ser Leu Ser Leu Glu Lys
                165                 170                 175 ctt gaa tac tta ctc tca agg tta agg gaa ata aaa cac gtg gaa att      576
Leu Glu Tyr Leu Leu Ser Arg Leu Arg Glu Ile Lys His Val Glu Ile
            180                 185                 190 ata cgc ttt ggg acg agg ctt ccc gtt ctt gca ccc cag agg ttc ttt      624
Ile Arg Phe Gly Thr Arg Leu Pro Val Leu Ala Pro Gln Arg Phe Phe
            195                 200                 205 aac gat aaa ctt ctg gac ata ctg gaa aaa tac tcc ccc ata tgg ata      672
Asn Asp Lys Leu Leu Asp Ile Leu Glu Lys Tyr Ser Pro Ile Trp Ile
210                 215                 220 aac act cac ttc aac cat ccg aat gag ata acc gag tac gcg gaa gaa      720
Asn Thr His Phe Asn His Pro Asn Glu Ile Thr Glu Tyr Ala Glu Glu
225                 230                 235                 240 gcg gtg gac agg ctc ctg aga agg ggc att ccc gtg aac aac cag aca      768
Ala Val Asp Arg Leu Leu Arg Arg Gly Ile Pro Val Asn Asn Gln Thr
                245                 250                 255 gtc cta ctt aaa ggc gta aac gac gac cct gaa gtt atg cta aaa ctc      816
Val Leu Leu Lys Gly Val Asn Asp Asp Pro Glu Val Met Leu Lys Leu
            260                 265                 270 ttt aga aaa ctt tta agg ata aag gta aag ccc cag tac ctc ttt cac      864
Phe Arg Lys Leu Leu Arg Ile Lys Val Lys Pro Gln Tyr Leu Phe His
            275                 280                 285 tgc gac ccg ata aag gga gcg gtt cac ttt agg act acg ata gac aaa      912
Cys Asp Pro Ile Lys Gly Ala Val His Phe Arg Thr Thr Ile Asp Lys
290                 295                 300 gga ctt gaa ata atg aga tat ttg agg gga agg ctg agc ggt ttc ggg      960
Gly Leu Glu Ile Met Arg Tyr Leu Arg Gly Arg Leu Ser Gly Phe Gly
305                 310                 315                 320 ata ccc act tac gcg gtg gac ctc ccg gga ggg aaa ggt aag gtt cct     1008
Ile Pro Thr Tyr Ala Val Asp Leu Pro Gly Gly Lys Gly Lys Val Pro
                325                 330                 335
```

```
ctt ctt ccc aac tac gta aag aaa agg aaa ggt aat aag ttc tgg ttt      1056
Leu Leu Pro Asn Tyr Val Lys Lys Arg Lys Gly Asn Lys Phe Trp Phe
        340                 345                 350 gaa agt ttc acg ggt gag gtc gta gaa tac gaa gta acg gaa gta tgg      1104
Glu Ser Phe Thr Gly Glu Val Val Glu Tyr Glu Val Thr Glu Val Trp
        355                 360                 365 gaa cct tga                                                          1113
Glu Pro
    370

<210> SEQ ID NO 14
<211> LENGTH: 370
<212> TYPE: PRT
<213> ORGANISM: Aquifex aeolicus

<400> SEQUENCE: 14

Met Arg Arg Phe Phe Glu Asn Val Pro Glu Asn Leu Trp Arg Ser Tyr
  1               5                  10                  15

Glu Trp Gln Ile Gln Asn Arg Ile Lys Thr Leu Lys Glu Ile Lys Lys
             20                  25                  30

Tyr Leu Lys Leu Leu Pro Glu Glu Glu Gly Ile Lys Arg Thr Gln
         35                  40                  45

Gly Leu Tyr Pro Phe Ala Ile Thr Pro Tyr Tyr Leu Ser Leu Ile Asn
     50                  55                  60

Pro Glu Asp Pro Lys Asp Pro Ile Arg Leu Gln Ala Ile Pro Arg Val
 65                  70                  75                  80

Val Glu Val Asp Glu Lys Val Gln Ser Ala Gly Glu Pro Asp Ala Leu
                 85                  90                  95

Lys Glu Glu Gly Asp Ile Pro Gly Leu Thr His Arg Tyr Pro Asp Arg
            100                 105                 110

Val Leu Leu Asn Val Thr Thr Phe Cys Ala Val Tyr Cys Arg His Cys
        115                 120                 125

Met Arg Lys Arg Ile Phe Ser Gln Gly Glu Arg Ala Arg Thr Lys Glu
    130                 135                 140

Glu Ile Asp Thr Met Ile Asp Tyr Ile Lys Arg His Glu Glu Ile Arg
145                 150                 155                 160

Asp Val Leu Ile Ser Gly Gly Glu Pro Leu Ser Leu Ser Leu Glu Lys
                165                 170                 175

Leu Glu Tyr Leu Leu Ser Arg Leu Arg Glu Ile Lys His Val Glu Ile
            180                 185                 190

Ile Arg Phe Gly Thr Arg Leu Pro Val Leu Ala Pro Gln Arg Phe Phe
        195                 200                 205

Asn Asp Lys Leu Leu Asp Ile Leu Glu Lys Tyr Ser Pro Ile Trp Ile
    210                 215                 220

Asn Thr His Phe Asn His Pro Asn Glu Ile Thr Glu Tyr Ala Glu Glu
225                 230                 235                 240

Ala Val Asp Arg Leu Leu Arg Arg Gly Ile Pro Val Asn Asn Gln Thr
                245                 250                 255

Val Leu Leu Lys Gly Val Asn Asp Asp Pro Glu Val Met Leu Lys Leu
            260                 265                 270

Phe Arg Lys Leu Leu Arg Ile Lys Val Lys Pro Gln Tyr Leu Phe His
        275                 280                 285

Cys Asp Pro Ile Lys Gly Ala Val His Phe Arg Thr Thr Ile Asp Lys
    290                 295                 300

Gly Leu Glu Ile Met Arg Tyr Leu Arg Gly Arg Leu Ser Gly Phe Gly
305                 310                 315                 320
```

```
Ile Pro Thr Tyr Ala Val Asp Leu Pro Gly Gly Lys Gly Lys Val Pro
            325                 330                 335

Leu Leu Pro Asn Tyr Val Lys Lys Arg Lys Gly Asn Lys Phe Trp Phe
            340                 345                 350

Glu Ser Phe Thr Gly Glu Val Glu Tyr Glu Val Thr Glu Val Trp
            355                 360                 365

Glu Pro
    370

<210> SEQ ID NO 15
<211> LENGTH: 1065
<212> TYPE: DNA
<213> ORGANISM: Treponema pallidum
<220> FEATURE:
<221> NAME/KEY: CDS
<222> LOCATION: (1)..(1065)

<400> SEQUENCE: 15 atg tct atg gct gag tgt acc cgg gaa cag aga aag aga cga ggt gca      48
Met Ser Met Ala Glu Cys Thr Arg Glu Gln Arg Lys Arg Arg Gly Ala
  1               5                  10                  15 ggg cgt gct gat gag cat tgg cgg acg ttg agt cct gcc tct tgc gcg      96
Gly Arg Ala Asp Glu His Trp Arg Thr Leu Ser Pro Ala Ser Cys Ala
                 20                  25                  30 gca gat gcg ctg acg gag cat att tct cca gcg tat gcg cat tta att     144
Ala Asp Ala Leu Thr Glu His Ile Ser Pro Ala Tyr Ala His Leu Ile
             35                  40                  45 gca caa gcg cag ggc gcg gac gcg cag gcg ctg aaa cgt cag gtg tgc     192
Ala Gln Ala Gln Gly Ala Asp Ala Gln Ala Leu Lys Arg Gln Val Cys
         50                  55                  60 ttt gcg cca cag gag cgt gtg gtg cat gct tgc gag tgt gcc gac cca     240
Phe Ala Pro Gln Glu Arg Val Val His Ala Cys Glu Cys Ala Asp Pro
 65                  70                  75                  80 ttg ggt gag gac cgg tac tgc gtg aca ccc ttt ttg gtg cat cag tat     288
Leu Gly Glu Asp Arg Tyr Cys Val Thr Pro Phe Leu Val His Gln Tyr
                 85                  90                  95 gcg aat cgt gtg ttg atg ttg gca aca gga cgt tgc ttt tca cac tgt     336
Ala Asn Arg Val Leu Met Leu Ala Thr Gly Arg Cys Phe Ser His Cys
                100                 105                 110 cgc tat tgt ttt cgc cgc ggt ttc atc gcc caa cgt gca ggg tgg atc     384
Arg Tyr Cys Phe Arg Arg Gly Phe Ile Ala Gln Arg Ala Gly Trp Ile
            115                 120                 125 ccc aac gaa gag cgc gag aag att att acg tat ctt cgt gct acc cct     432
Pro Asn Glu Glu Arg Glu Lys Ile Ile Thr Tyr Leu Arg Ala Thr Pro
        130                 135                 140 tcg gtg aag gaa atc ctg gtt tca ggt ggt gat cca ctc act ggt tct     480
Ser Val Lys Glu Ile Leu Val Ser Gly Gly Asp Pro Leu Thr Gly Ser
145                 150                 155                 160 ttt gca cag gtc aca tcg ctt ttc cgc gca ctg cgc agt gta gcg ccg     528
Phe Ala Gln Val Thr Ser Leu Phe Arg Ala Leu Arg Ser Val Ala Pro
                165                 170                 175 gat ttg att att cgt ctg tgc act cgc gca gtc acc ttt gct ccg cag     576
Asp Leu Ile Ile Arg Leu Cys Thr Arg Ala Val Thr Phe Ala Pro Gln
            180                 185                 190 gcc ttt act ccc gag ctg att gcg ttt ctg cag gag atg aag ccg gtg     624
Ala Phe Thr Pro Glu Leu Ile Ala Phe Leu Gln Glu Met Lys Pro Val
        195                 200                 205 tgg ata att ccg cat att aat cac ccg gca gag ctc ggt tct acg cag     672
Trp Ile Ile Pro His Ile Asn His Pro Ala Glu Leu Gly Ser Thr Gln
    210                 215                 220
```

```
cgc gcg gtg ctc gag gcc tgc gta ggc gca ggc ctc cct gtg caa tcg      720
Arg Ala Val Leu Glu Ala Cys Val Gly Ala Gly Leu Pro Val Gln Ser
225                 230                 235                 240 cag tcg gta ctg ttg cgc ggg gtg aac gat tcg gta gag acg ctg tgc      768
Gln Ser Val Leu Leu Arg Gly Val Asn Asp Ser Val Glu Thr Leu Cys
                245                 250                 255 aca ctg ttt cac gcg ctc act tgt ctg ggg gtt aag ccg ggg tat cta      816
Thr Leu Phe His Ala Leu Thr Cys Leu Gly Val Lys Pro Gly Tyr Leu
    260                 265                 270 ttt cag ttg gat ttg gcg cct gga act ggg gat ttt cgt gtg cca ctt      864
Phe Gln Leu Asp Leu Ala Pro Gly Thr Gly Asp Phe Arg Val Pro Leu
275                 280                 285 tct gac acg cta gct ctg tgg cgc aca ttg aag gag cgc ctc tca ggg      912
Ser Asp Thr Leu Ala Leu Trp Arg Thr Leu Lys Glu Arg Leu Ser Gly
            290                 295                 300 ttg tcg ctt ccc acg ctt gcg gtg gac ttg cca ggg ggt gga gga aag      960
Leu Ser Leu Pro Thr Leu Ala Val Asp Leu Pro Gly Gly Gly Gly Lys
305                 310                 315                 320 ttt ccg ctt gtg gca ttg gcc ttg cag caa gat gtc acg tgg cat cag     1008
Phe Pro Leu Val Ala Leu Ala Leu Gln Gln Asp Val Thr Trp His Gln
                325                 330                 335 gaa cgc gag gcg ttc tcc gca cgc ggc atc gat ggc gcg tgg tac acg     1056
Glu Arg Glu Ala Phe Ser Ala Arg Gly Ile Asp Gly Ala Trp Tyr Thr
                340                 345                 350 tac ccg ttc                                                         1065
Tyr Pro Phe
        355

<210> SEQ ID NO 16
<211> LENGTH: 355
<212> TYPE: PRT
<213> ORGANISM: Treponema pallidum

<400> SEQUENCE: 16

Met Ser Met Ala Glu Cys Thr Arg Glu Gln Arg Lys Arg Arg Gly Ala
1               5                   10                  15

Gly Arg Ala Asp Glu His Trp Arg Thr Leu Ser Pro Ala Ser Cys Ala
            20                  25                  30

Ala Asp Ala Leu Thr Glu His Ile Ser Pro Ala Tyr Ala His Leu Ile
        35                  40                  45

Ala Gln Ala Gln Gly Ala Asp Ala Gln Ala Leu Lys Arg Gln Val Cys
    50                  55                  60

Phe Ala Pro Gln Glu Arg Val Val His Ala Cys Glu Cys Ala Asp Pro
65                  70                  75                  80

Leu Gly Glu Asp Arg Tyr Cys Val Thr Pro Phe Leu Val His Gln Tyr
                85                  90                  95

Ala Asn Arg Val Leu Met Leu Ala Thr Gly Arg Cys Phe Ser His Cys
            100                 105                 110

Arg Tyr Cys Phe Arg Arg Gly Phe Ile Ala Gln Arg Ala Gly Trp Ile
        115                 120                 125

Pro Asn Glu Glu Arg Glu Lys Ile Ile Thr Tyr Leu Arg Ala Thr Pro
    130                 135                 140

Ser Val Lys Glu Ile Leu Val Ser Gly Gly Asp Pro Leu Thr Gly Ser
145                 150                 155                 160

Phe Ala Gln Val Thr Ser Leu Phe Arg Ala Leu Arg Ser Val Ala Pro
                165                 170                 175

Asp Leu Ile Ile Arg Leu Cys Thr Arg Ala Val Thr Phe Ala Pro Gln
```

-continued

```
                180                 185                 190
Ala Phe Thr Pro Glu Leu Ile Ala Phe Leu Gln Glu Met Lys Pro Val
        195                 200                 205

Trp Ile Ile Pro His Ile Asn His Pro Ala Glu Leu Gly Ser Thr Gln
    210                 215                 220

Arg Ala Val Leu Glu Ala Cys Val Gly Ala Gly Leu Pro Val Gln Ser
225                 230                 235                 240

Gln Ser Val Leu Leu Arg Gly Val Asn Asp Ser Val Glu Thr Leu Cys
                245                 250                 255

Thr Leu Phe His Ala Leu Thr Cys Leu Gly Val Lys Pro Gly Tyr Leu
            260                 265                 270

Phe Gln Leu Asp Leu Ala Pro Gly Thr Gly Asp Phe Arg Val Pro Leu
        275                 280                 285

Ser Asp Thr Leu Ala Leu Trp Arg Thr Leu Lys Glu Arg Leu Ser Gly
    290                 295                 300

Leu Ser Leu Pro Thr Leu Ala Val Asp Leu Pro Gly Gly Gly Gly Lys
305                 310                 315                 320

Phe Pro Leu Val Ala Leu Ala Leu Gln Gln Asp Val Thr Trp His Gln
                325                 330                 335

Glu Arg Glu Ala Phe Ser Ala Arg Gly Ile Asp Gly Ala Trp Tyr Thr
            340                 345                 350

Tyr Pro Phe
        355

<210> SEQ ID NO 17
<211> LENGTH: 6
<212> TYPE: PRT
<213> ORGANISM: Clostridium subterminale

<400> SEQUENCE: 17

Lys Asp Val Ser Asp Ala
  1               5

<210> SEQ ID NO 18
<211> LENGTH: 17
<212> TYPE: DNA
<213> ORGANISM: Clostridium subterminale
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (12)
<223> OTHER INFORMATION: inosine

<400> SEQUENCE: 18
aargaygtnw sngaygc                                                 17

<210> SEQ ID NO 19
<211> LENGTH: 6
<212> TYPE: PRT
<213> ORGANISM: Clostridium subterminale

<400> SEQUENCE: 19

Gln Ser His Asp Lys Val
  1               5

<210> SEQ ID NO 20
<211> LENGTH: 20
<212> TYPE: DNA
```

```
<213> ORGANISM: Clostridium subterminale
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (15)
<223> OTHER INFORMATION: inosine

<400> SEQUENCE: 20
atnacyttrt crtgnswytg                                              20

<210> SEQ ID NO 21
<211> LENGTH: 48
<212> TYPE: PRT
<213> ORGANISM: Clostridium subterminale

<400> SEQUENCE: 21

Pro Asn Tyr Val Ile Ser Gln Ser His Asp Lys Val Ile Leu Arg Asn
 1               5                  10                  15

Phe Glu Gly Val Ile Thr Thr Tyr Ser Glu Pro Ile Asn Tyr Thr Pro
            20                  25                  30

Gly Cys Asn Cys Asp Val Cys Thr Gly Lys Lys Lys Val His Lys Val
        35                  40                  45

<210> SEQ ID NO 22
<211> LENGTH: 15
<212> TYPE: PRT
<213> ORGANISM: Clostridium subterminale

<400> SEQUENCE: 22

Ala Leu Glu Pro Val Gly Leu Glu Arg Asn Lys Arg His Val Gln
 1               5                  10                  15

<210> SEQ ID NO 23
<211> LENGTH: 16
<212> TYPE: PRT
<213> ORGANISM: Clostridium subterminale

<400> SEQUENCE: 23

Met Ile Asn Arg Arg Tyr Glu Leu Phe Lys Asp Val Ser Asp Ala Asp
 1               5                  10                  15

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atcctaacga tcctaatgat cc                                           22

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tggatggtta aagtgagtg                                               19
```

<210> SEQ ID NO 26
<211> LENGTH: 500
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26

```
atcctaacga tcctaatgat ccagtaagaa acaagctat tccaacagca ttagagctta      60
acaaagctgc tgcagatctt gaagacccat tacatgaaga tacagattca ccagtacctg    120
gattaactca cagatatcca gatagagtat tattattaat aactgatatg tgctcaatgt    180
actgcagaca ctgtacaaga agaagatttg caggacaaag cgatgactct atgccaatgg    240
aaagaataga taaagctata gattatatca gaaatactcc tcaagttaga gacgtattat    300
tatcaggtgg agacgctctt ttagtatctg atgaaacatt agaatacatc atagctaaat    360
taagagaaat accacacgtt gaaatagtaa gaataggttc aagaactcca gttgttcttc    420
cacaaagaat aactccagaa cttgtaaata tgcttaaaaa atatcatcca gtatggttaa    480
acactcactt taaccatcca                                                500
```

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
tacacatatg ataaatagaa gatatg                                          26
```

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
tagactcgag ttattcttga acgtgtctc                                       29
```

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
tacagaattc atgataaata gaagatatg                                       29
```

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
tagaaagctt ttattcttga acgtgtctc                                              29
```

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
tataggatcc gaccgtataa ttcacgcgat tacacc                                      36
```

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
tagagaattc gattcagtca ggcgtcccat tatc                                        34
```

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: variable amino acid
<220> FEATURE:
<221> NAME/KEY: MOD_RES
<222> LOCATION: (7)
<223> OTHER INFORMATION: variable amino acid
<220> FEATURE:
<221> NAME/KEY: MOD_RES
<222> LOCATION: (9)
<223> OTHER INFORMATION: variable amino acid

<400> SEQUENCE: 33

```
Cys Xaa Xaa Xaa Cys Arg Xaa Cys Xaa Arg
 1               5                  10
```

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ser or Thr
<220> FEATURE:
<221> NAME/KEY: MOD_RES
<222> LOCATION: (4)
<223> OTHER INFORMATION: Asp or Glu

<400> SEQUENCE: 34

```
Xaa Gly Gly Xaa
 1
```

<210> SEQ ID NO 35
<211> LENGTH: 7

```
-continued

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Pro, Ala, or Gly
<220> FEATURE:
<221> NAME/KEY: MOD_RES
<222> LOCATION: (2)
<223> OTHER INFORMATION: Gly or Ser
<220> FEATURE:
<221> NAME/KEY: MOD_RES
<222> LOCATION: (3)..(5)
<223> OTHER INFORMATION: variable amino acid
<220> FEATURE:
<221> NAME/KEY: MOD_RES
<222> LOCATION: (7)
<223> OTHER INFORMATION: Thr, Ile, Val or Phe

<400> SEQUENCE: 35

Xaa Xaa Xaa Xaa Xaa Lys Xaa
 1               5
```